(12) United States Patent
Tasaka et al.

(10) Patent No.: US 6,716,863 B2
(45) Date of Patent: Apr. 6, 2004

(54) HETEROCYCLIC COMPOUNDS THEIR PRODUCTION AND USE

(75) Inventors: Akihiro Tasaka, Suita (JP); Takenori Hitaka, Takarazuka (JP); Etsuya Matsutani, Suita (JP)

(73) Assignee: Takeda Chemical Industries, Ltd., Osaka (JP)

( * ) Notice: Subject to any disclaimer, the term of this patent is extended or adjusted under 35 U.S.C. 154(b) by 86 days.

(21) Appl. No.: 09/889,974

(22) PCT Filed: Apr. 5, 2001

(86) PCT No.: PCT/JP01/02937

§ 371 (c)(1), (2), (4) Date: Jul. 24, 2001

(87) PCT Pub. No.: WO01/77107

PCT Pub. Date: Oct. 18, 2001

(65) Prior Publication Data

US 2002/0173526 A1 Nov. 21, 2002

(30) Foreign Application Priority Data

Apr. 7, 2000 (JP) .......................................... 2000-106836

(51) Int. Cl.[7] ..................... A61K 31/422; C07D 413/12
(52) U.S. Cl. ...................................... 514/374; 548/235
(58) Field of Search ........................... 514/374; 548/235

(56) References Cited

U.S. PATENT DOCUMENTS 6,211,215 B1 * 4/2001 Momose et al. ............ 514/374

FOREIGN PATENT DOCUMENTS

WO        91/16051        10/1991
WO        98/03505        1/1998

* cited by examiner

Primary Examiner—Joseph K. McKane
Assistant Examiner—Rebecca Anderson
(74) Attorney, Agent, or Firm—Wenderoth, Lind & Ponack, L.L.P.

(57) ABSTRACT

A compound represented by the formula:

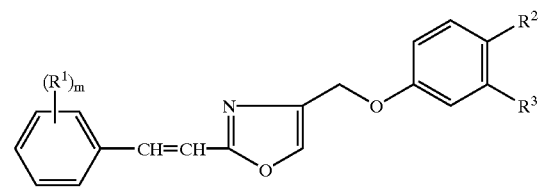

wherein m is 1 or 2, $R^1$ is a halogen or an optionally halogenated $C_{1-2}$ alkyl; one of $R^2$ and $R^3$ is a hydrogen atom and the other is a group represented by the formula:

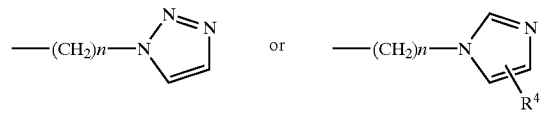

wherein n is 3 or 4; $R^4$ is a $C_{1-4}$ alkyl group substituted by 1 or 2 hydroxy groups, or a salt thereof shows tyrosine kinase-inhibiting activity.

30 Claims, No Drawings

HETEROCYCLIC COMPOUNDS THEIR PRODUCTION AND USE

This application is a 371 of PCT/01/02937 filed Apr. 5, 2001.

TECHNICAL FIELD

The present invention relates to a heterocyclic compound which is useful as a growth factor receptor tyrosine kinase (particularly HER2) inhibitor, a method for its production, and a pharmaceutical composition containing it.

BACKGROUND

Growth factor and growth factor receptor genes, known as proto-oncogenes, have play important roles in the pathology of human tumors such as breast cancer (Aronson et al., Science, Vol. 254, pp. 1146–1153, 1991). Having homology to epidermal growth factor (EGF) receptor, the HER2 (human EGF receptor-2) gene encodes transmembrane-type glycoprotein, and this receptor possesses tyrosine kinase activity (Akiyama et al., Science, Vol. 232, pp. 1644–1646, 1986). HER2 is found in human breast cancer and ovarian cancer (Slamon et al., Science, Vol. 244, pp. 707–712, 1989) and is also found in prostate cancer (Lyne et al., Proceedings of the American Association for Cancer Research, Vol. 37, p. 243, 1996) and gastric cancer (Yonemura et al., Cancer Research, Vol. 51, p. 1034, 1991). In addition, the substrate for HER2 tyrosine kinase is found in 90% of cases of pancreatic cancer. Transgenic mice incorporating the HER2 gene develop breast cancer as they grow (Guyre et al., Proceedings of the National Academy of Science, USA, Vol. 89, pp. 10578–10582, 1992).

An antibody against HER2 was shown to suppress in vitro proliferation of cancer cells (McKenzie et al., Oncogene, Vol. 4, pp. 543–548, 1989); in addition, a human monoclonal antibody against HER2 provided encouraging results in a clinical study in breast cancer patients (Baselga et al., Journal of Clinical Oncology, Vol. 14, pp. 737–744, 1996).

These antibodies interfere with growth factors to bind to HER2 and inhibit the activation of tyrosine kinase. Because these antibodies were thus shown to suppress the progression of cancer in breast cancer patients, drugs which directly inhibit HER2 tyrosine kinase were shown to be potentially effective as therapeutic drugs for breast cancer (Hayes, Journal of Clinical Oncology, Vol. 14, pp. 697–699, 1996).

As a compound that inhibits receptor type tyrosine kinases, including HER2, Japanese Patent Unexamined Publication No. 60571/1999 discloses a compound represented by the formula:

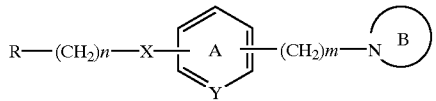

wherein R is a is an aromatic heterocyclic group which may be substituted; X is an oxygen atom, an optionally oxidized sulfur atom, —C(=O)— or —CH(OH)—; Y is CH or N; m is an integer from 0 to 10; n is an integer from 1 to 5; the cyclic group:

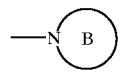

is an aromatic azole group which may be substituted; Ring A may be further substituted.

And, there is demand for the development of a compound which possesses excellent tyrosine kinase-inhibiting activity, which is of low toxicity, and which is satisfactory as a pharmaceutical.

DISCLOSURE OF INVENTION

The present inventors conducted various investigations on heterocyclic compounds possessing tyrosine kinase-inhibiting activity and succeeded in synthesizing for the first time a compound represented by the formula:

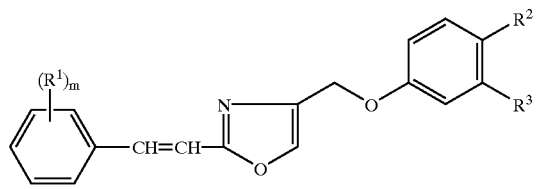

wherein m is 1 or 2;
$R^1$ is a halogen atom or an optionally halogenated $C_{1-2}$ alkyl group;
one of $R^2$ and $R^3$ is a a hydrogen atom and the other is a group represented by the formula:

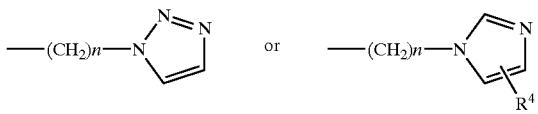

wherein n is 3 or 4; $R^4$ is a $C_{1-4}$ alkyl group substituted by 1 to 2 hydroxy groups (hereinafter also referred to as Compound (I)), which has a chemical structure unique in that phenyl of the phenylethenyl of the skeleton represented by the formula:

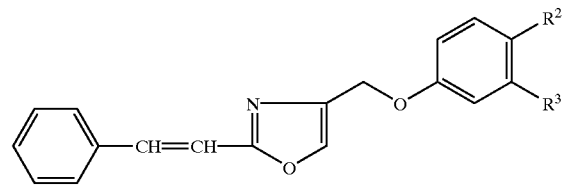

wherein the symbols have the same definitions as those shown below is substituted by a halogen or an optionally halogenated $C_{1-2}$ alkyl, or a salt thereof, and found that this Compound (I) or a salt thereof possesses an unexpectedly excellent tyrosine kinase-inhibiting activity based on its unique chemical structure. The inventors conducted further investigations based on this finding and developed the present invention.

Accordingly, the present invention relates to:
(1) A compound (I) or a salt thereof;
(2) A compound as defined in (1) above, wherein $R^1$ is fluoro or trifluoromethyl, or a salt thereof;
(3) A compound as defined in (1) above, wherein $R^2$ is a group represented by the formula:

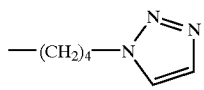

and R³ is a hydrogen atom; or
R² is a hydrogen atom and R³ is a group represented by the formula:

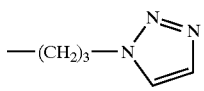

or a salt thereof;
(4) A compound as defined in (1) above, wherein R² is a group represented by the formula:

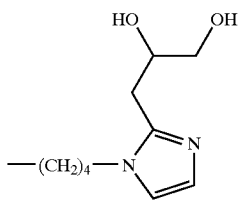

and R³ is a hydrogen atom, or a salt thereof;
(5) A compound as defined in (1) above, wherein m is 1; R¹ is 4-trifluoromethyl;
R² is a group represented by the formula:

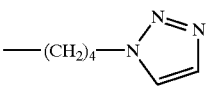

and R³ is a hydrogen atom, or a salt thereof;
(6) A compound as defined in (1) above, which is 1-(4-{4-[(2-{(E)-2-[4-(trifluoromethyl)phenyl]ethenyl}-1,3-oxazol-4-yl)methoxy]phenyl}butyl)-1H-1,2,3-triazole, 1-(3-(3-[(2-{(E)-2-[4-(trifluoromethyl)phenyl]ethenyl}-1,3-oxazol-4-yl)methoxy]phenyl}propyl)-1H-1,2,3-triazole, or 3-(1-{4-[4-({2-[(E)-2-(2,4-difluorophenyl)ethenyl]-1,3-oxazol-4-yl}methoxy)phenyl]butyl}-1H-imidazol-2-yl)-1,2-propanediol, or a salt thereof;
(7) A method for producing Compound (I)or a salt thereof comprising reacting a compound represented by the formula:

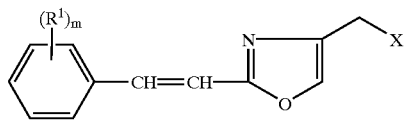

wherein, X is a leaving group; the other symbols have the same meanings as defied above, or a salt thereof, with a compound represented by the formula:

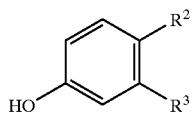

wherein the symbols have the same meanings as defied above, or a salt thereof;

(8) A pro-drug of a compound as defined in (1) above;
(9) A pharmaceutical composition containing a compound as defined in (1) above or a salt thereof or a pro-drug thereof;
(10) A pharmaceutical composition as defined in (9) above, which is a tyrosine kinase inhibitor;
(11) A pharmaceutical composition as defined in (9) above, which is an agent for preventing or treating cancer;
(12) A pharmaceutical composition as defined in (11) above, wherein the cancer is breast cancer or prostate cancer;
(13) A pharmaceutical composition as defined in (11) above, wherein the cancer is lung cancer;
(14) A pharmaceutical composition which combines a compound as defined in (1) above or a salt thereof or a pro-drug thereof and other anti-cancer agents;
(15) A pharmaceutical composition which combines a compound as defined in (1) above or a salt thereof or a pro-drug thereof and hormonal therapeutic agents;
(16) The pharmaceutical composition as defined in (15) above, wherein the hormonal therapeutic agent is a LH-RH modulator;
(17) The pharmaceutical composition as defined in (16) above, wherein the LH-RH modulator is LH-RH antagonist;
(18) The pharmaceutical composition as defined in (17) above, wherein the LH-RH antagonist is leuprorelin or a salt thereof;
(19) A method for inhibiting tyrosine-kinase which comprises administering an effective amount of a compound as defined in (1) above or a salt thereof or a pro-drug thereof to mammals;
(20) A method for preventing or treating cancer which comprises administering an effective amount of a compound as defined in (1) above or a salt thereof or a pro-drug thereof to mammals;
(21) A method for preventing or treating cancer which comprises combining [1] administering an effective amount of a compound as defined in (1) above or a salt thereof or a pro-drug thereof to mammals and [2] 1 to 3 selected from the group consisting (i) administering an effective amount of other anti-cancer agents to mammals, (ii) administering an effective amount of hormonal therapeutic agents to mammals and (iii) non-drug therapy;
(22) The method as defined in (21) above wherein non-drug therapy is surgery, hypertensive chemotherapy, genetherapy, thermotherapy, cryotherapy, laser cauterization and/or radiotherapy;
(23) A method for preventing or treating cancer which comprises administering in combination of an effective amount of a compound as defined in (1) above or a salt thereof or a pro-drug thereof and an effective amount of other anti-cancer agents to mammals;
(24) A method for preventing or treating cancer which comprises administering in combination of an effective amount of a compound as defined in (1) above or a salt thereof or a pro-drug thereof and an effective amount of hormonal therapeutic agents to mammals;
(25) The method as defined in (24) above, wherein the hormonal therapeutic agent is a LH-RH modulator;
(26) The method as defined in (25) above, wherein the LH-RH modulator is LH-RH antagonist;
(27) The method as defined in (26) above, wherein the LH-RH antagonist is leuprorelin or a salt thereof;
(28) A method for preventing or treating cancer which comprises administering an effective amount of a compound as defined in (1) above or a salt thereof or a pro-drug thereof to mammals before surgery, hypertensive chemotherapy, genetherapy, thermotherapy, cryotherapy, laser cauterization and/or radiotherapy;

(29) A method for preventing or treating cancer which comprises administering an effective amount of a compound as defined in (1) above or a salt thereof or a pro-drug thereof to mammals after surgery, hypertensive chemotherapy, genetherapy, thermotherapy, cryotherapy, laser cauterization and/or radiotherapy;

(30) A method for preventing or treating cancer which comprises administering in combination of an effective amount of a compound as defined in (1) above or a salt thereof or a pro-drug thereof and an effective amount of other anti-cancer agents to mammals before surgery, hypertensive chemotherapy, genetherapy, thermotherapy, cryotherapy, laser cauterization and/or radiotherapy;

(31) A method for preventing or treating cancer which comprises administering in combination of an effective amount of a compound as defined in (1) above or a salt thereof or a pro-drug thereof and an effective amount of other anti-cancer agents to mammals before surgery, hypertensive chemotherapy, genetherapy, thermotherapy, cryotherapy, laser cauterization and/or radiotherapy;

(32) The method as defined in (31) above, wherein the hormonal therapeutic agent is a LH-RH modulator;

(33) The method as defined in (32) above, wherein the LH-RH modulator is LH-RH antagonist;

(34) The method as defined in (33) above, wherein the LH-RH antagonist is leuprorelin or a salt thereof;

(35) A method for preventing or treating cancer which comprises administering in combination of an effective amount of a compound as defined in (1) above or a salt thereof or a pro-drug thereof and an effective amount of other anti-cancer agents to mammals after surgery, hypertensive chemotherapy, genetherapy, thermotherapy, cryotherapy, laser cauterization and/or radiotherapy;

(36) A method for preventing or treating cancer which comprises administering in combination of an effective amount of a compound as defined in (1) above or a salt thereof or a pro-drug thereof and an effective amount of other anti-cancer agents to mammals after surgery, hypertensive chemotherapy, genetherapy, thermotherapy, cryotherapy, laser cauterization and/or radiotherapy;

(37) The method as defined in (36) above, wherein the hormonal therapeutic agent is a LH-RH modulator;

(38) The method as defined in (37) above, wherein the LH-RH modulator is LH-RH antagonist;

(39) The method as defined in (38) above, wherein the LH-RH antagonist is leuprorelin or a salt thereof;

(40) Use of a compound as defined in (1) above or a salt thereof or a pro-drug thereof for preparing a tyrosine kinase inhibitor;

(41) Use of a compound as defined in (1) above or a salt thereof or a pro-drug thereof for preparing an agent for preventing or treating cancer;

(42) A compound represented by the formula:

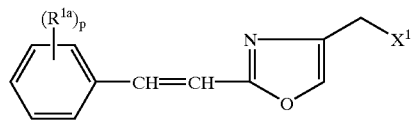

wherein $R^{1a}$ is fluoro or trifluoromethyl, $X^1$ is a leaving group, and n is 3 or 4, or a salt thereof;

(43) A compound as defined in (42) above, wherein $X^1$ is a halogen atom; and

(44) Use of a compound as defined in (42) above or a salt thereof for preparing a compound as defied in (1) above.

With respect to the formula above, the "halogen atom" represented by $R^1$ is exemplified by fluoro, chloro, bromo, and iodo. In particular, fluoro is preferred.

The "halogen" of the "optionally halogenated $C_{1-2}$ alkyl group" represented by $R^1$ is exemplified by fluoro, chloro, bromo, and iodo. In particular, fluoro is preferred.

The "$C_{1-2}$ alkyl group" of the "optionally halogenated $C_{1-2}$ alkyl group" represented by $R^1$ is exemplified by methyl and ethyl, and methyl is preferred.

Said "$C_{1-2}$ alkyl group" may have 1 to 3, preferably 2 or 3, halogens mentioned above at any possible positions; when 2 or more such halogens are present, they may be identical or different.

As specific examples of said "optionally halogenated $C_{1-2}$ alkyl group", there may be mentioned methyl, ethyl, and trifluoromethyl.

$R^1$ is preferably a halogen atom or a halogenated $C_{1-2}$ alkyl group, and fluoro and trifluoromethyl are more preferable.

When m is 2, the $R^1$ groups may be different.

The group represented by $R^2$ or $R^3$ for the formula:

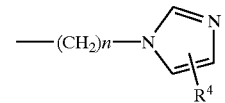

wherein $R^4$ has the same meanings as defined above, is preferably a group represented by the formula:

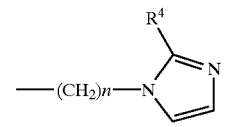

wherein $R^4$ has the same meaning as defined above.

As examples of the "$C_{1-4}$ alkyl group" of the "$C_{1-4}$ alkyl group substituted by 1 or 2 hydroxy groups" represented by $R^4$, there may be mentioned methyl, ethyl, propyl, isopropyl, butyl, isobutyl, sec-butyl, and tert-butyl. In particular, ethyl, propyl, etc. are preferred.

As examples of said "$C_{1-4}$ alkyl group substituted by 1 to 2 hydroxy groups," there may be mentioned 2-hydroxyethyl, 2,3-dihydroxypropyl, and 1,3-dihydroxypropyl. In particular, 2,3-dihydroxypropyl is preferred.

When $R^2$ is

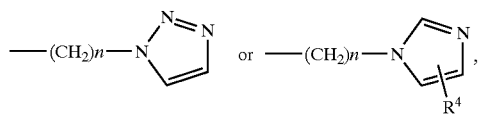

n is preferably 3.

When $R^3$ is

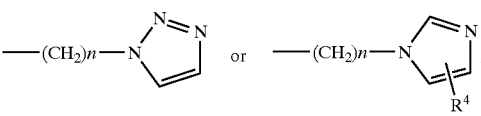

n is preferably 3. With respect to the formula above, it is preferable that $R^2$ is a group represented by the formula:

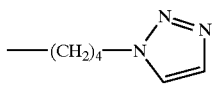

and R³ is a hydrogen atom.

It is also preferable that R² is a hydrogen atom and R³ is a group represented by the formula:

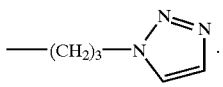

It is also preferable that R² is a group represented by the formula:

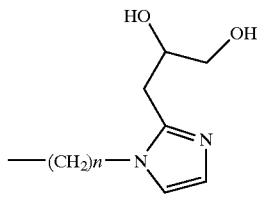

wherein n has the same meaning as defined above, and R³ is a hydrogen atom, with n being more preferably 4.

As a preferable example of Compound (I), there may be mentioned a compound represented by the formula:

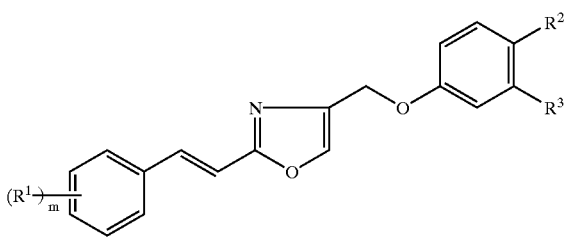

wherein the symbols have the same meaning as defined above, or a salt thereof.

Of Compound (I), a compound wherein m is 1; R¹ is 4-trifluoromethyl; R² is a group represented by the formula:

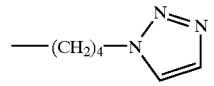

and R³ is a hydrogen atom, or a salt thereof is preferred.

As specific examples of Compound (I), there may be mentioned 1-(4-{4-[(2-{(E)-2-[4-(trifluoromethyl)phenyl] ethenyl}-1,3-oxazol-4-yl)methoxy]phenyl)butyl)-1H-1,2,3-triazole, 1-(3-{3-[(2-{(E)-2-[4-(trifluoromethyl)phenyl] ethenyl}-1,3-oxazol-4-yl)methoxy]phenyl}propyl)-1H-1,2,3-triazole, 3-(1-{4-[4-({2-[(E)-2-(2,4-difluorophenyl) ethenyl]-1,3-oxazol-4-yl}methoxy)phenyl]butyl}-1H-imidazol-2-yl)-1,2-propanediol, or salts thereof.

As the salt of Compound (I) of the present invention, pharmaceutically acceptable salts are preferred, including salts with inorganic bases, salts with organic bases, salts with inorganic acids, salts with organic acids, and salts with basic or acidic amino acids. As preferable examples of salts with inorganic bases, there may be mentioned alkali metal salts such as sodium salt and potassium salt; alkaline earth metal salts such as calcium salt and magnesium salt; aluminum salt; and ammonium salt. As preferable examples of salts with organic bases, there may be mentioned salts with trimethylamine, triethylamine, pyridine, picoline, ethanolamine, diethanolamine, triethanolamine, dicyclohexylamine, N,N'-dibenzylethylenediamine, etc. As preferable examples of salts with inorganic acids, there may be mentioned salts with hydrochloric acid, hydrobromic acid, nitric acid, sulfuric acid, phosphoric acid, etc. As preferable examples of salts with organic acids, there may be mentioned salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. As preferable examples of salts with basic amino acids, there may be mentioned salts with arginine, lysine, ornithine, etc.; as preferable examples of salts with acidic amino acids, there may be mentioned salts with aspartic acid, glutamic acid, etc.

In Compound (I), two kinds, i.e., (Z)-ethenyl configuration and (E)-ethenyl configuration, are present; these isomers are included in the scope of the present invention, whether they are present in the form of simple substances or mixtures.

Furthermore, when Compound (I) has asymmetric carbons, optical isomers exist; these isomers are included in the scope of the present invention, whether they are present in the form of simple substance or mixtures.

Compound (I) of the present invention or a salt thereof is obtained by commonly known methods, e.g., a method based on the method described in Japanese Patent Unexamined Publication No. 60571/1999, and is also obtained by, for example, the methods schematized by Reaction Formulas A through H below.

The symbols for the compounds given in the schemes for the reaction formulas below have the same definitions as those shown above. The compounds shown in the reaction formulas include salts thereof; examples of such salts include the same salts as those of Compound (I).

Reaction Formula A

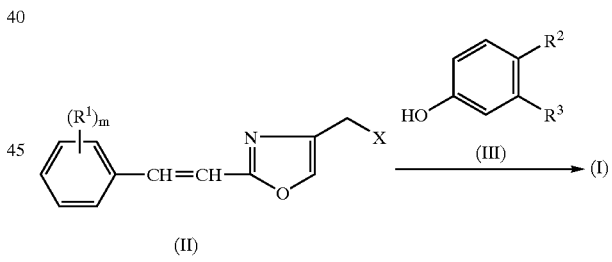

As examples of the "leaving group" represented by X, there may be mentioned halogens (e.g., chloro, bromo) or a group represented by the formula: —OSO₂R⁵ wherein R⁵ is an alkyl or an aryl optionally having a substituent.

As examples of the "alkyl" represented by R⁵, there may be mentioned $C_{1-6}$ alkyl such as methyl, ethyl, and propyl.

As examples of the "aryl" of the "aryl optionally having a substituent" represented by R⁵, there may be mentioned $C_{6-14}$ aryls such as phenyl.

The "substituent" of the "aryl optionally having a substituent" represented by R⁵ is exemplified by $C_{1-6}$ alkyls such as methyl, ethyl, and propyl.

As specific examples of said "aryl optionally having a substituent," there may be mentioned phenyls (e.g., p-tolyl) which may have a $C_{1-6}$ alkyl.

Compound (II) and Compound (III) are reacted to yield Compound (I).

This condensation reaction is usually carried out in the presence of a base between Compound (II) and Compound (III).

As examples of said "base," there may be mentioned alkali metal or alkaline earth metal hydroxides (e.g., sodium hydroxide, potassium hydroxide), alkali metal or alkaline earth metal carbonates (e.g., sodium hydrogen carbonate, sodium carbonate, potassium carbonate), amines (e.g., pyridine, triethylamine, N,N-dimethylaniline), alkali metal or alkaline earth metal hydrides (e.g., sodium hydride, potassium hydride, calcium hydride), and alkali metal or alkaline earth metal lower alkoxides (e.g., sodium methoxide, sodium ethoxide, potassium tert-butoxide).

The amount of "base" used is preferably about 1 to 5 mol per mol of Compound (II).

The amount of "Compound (III)" used is preferably about 0.5 to 5 mol per mol of Compound (II).

This reaction is advantageously carried out in the presence of a base which does not interfere with the reaction. Said solvent is not subject to limitation, as long as the reaction proceeds; as examples of this solvent, aromatic hydrocarbons, ethers, ketones, halogenated hydrocarbons, amides, sulfoxides or mixtures of two or more kinds thereof may be used.

Reaction temperature is normally −50 to +150° C., preferably about −10 to +100° C. Reaction time is normally 0.5 to 48 hours.

Compound (II) can be produced by a commonly known method or a modification thereof, e.g., Compound (IIa), wherein X is chloro, can be produced by the method shown by Reaction Formula B below, or the like.

Reaction Formula B

Compound (IV) and 1,3-dichloroacetone are subjected to a condensation/dehydration reaction to yield Compound (IIa).

If available commercially, Compound (IV) may be used as a commercial product as is, or may be produced by a commonly known method, a modification thereof, or the like.

The amount of "1,3-dichloroacetone" used is about 1 equivalent to a large excess (amount of solvent) relative to Compound (IV).

This reaction is advantageously carried out in the absence of solvent or in the presence of solvent which does not interfere with the reaction. Said solvent is not subject to limitation, as long as the reaction proceeds; as examples of this solvent, aromatic hydrocarbons, ethers, ketones, halogenated hydrocarbons or mixtures of two or more kinds thereof may be used.

Reaction temperature is normally 50 to 150° C., preferably about 60 to 120° C. Reaction time is normally 0.5 to 48 hours.

Although the product can be used for the next reaction in the form of a reaction mixture as-is, or in the form of a crude product, it can also be isolated from the reaction mixture by a conventional method.

Of Compound (III), Compound (IIIa), wherein $R^3$ is a hydrogen atom, can be produced by a commonly known method or a modification thereof, e.g., the method shown by Reaction Formula C below.

Reaction Formula C

With respect to the formula above, $P^a$ is a hydrogen atom or a protective group; $X^a$ is a leaving group.

As examples of the "protective group" represented by $P^a$, there may be mentioned alkyls (e.g., $C_{1-6}$ alkyls such as methyl and ethyl), phenyl-$C_{1-6}$ alkyls (e.g., benzyl), $C_{1-6}$ alkylcarbonyl, alkyl-substituted silyl (e.g., trimethylsilyl, tert-butyldimethylsilyl).

As examples of the "leaving group" represented by $X^a$, there may be mentioned the same examples as those of the "leaving group" represented by X above.

By condensing Compound (V) and Compound (VI) or Compound (VII) to yield Compound (VIII), which is subjected to a deprotecting reaction as necessary, Compound (IIIa) is obtained.

If available commercially, each of Compound (V), Compound (VI) and Compound (VII) may be used as a commercial product as is, or may be produced by a commonly known method, a modification thereof, or the like.

Said "condensation reaction" is normally carried out in the presence of a base in a solvent which does not interfere with the reaction.

Said "base" is exemplified by the bases described in detail with respect to Reaction Formula A above.

The amount of "base" used is preferably about 1 to 5 mol per mol of Compound (V).

The amount of Compound (VI) or Compound (VII) used is preferably about 0.5 to 5 mol per mol of Compound (V).

Said solvent is not subject to limitation, as long as the reaction proceeds; as examples of this solvent, aromatic hydrocarbons, ethers, ketones, halogenated hydrocarbons, amides, sulfoxides or mixtures of two or more kinds thereof may be used.

The reaction temperature is normally −50 to +150° C., preferably about −10 to +100° C. Reaction time is about 0.5 to 48 hours.

Although Compound (VIII) obtained can be used for the next reaction in the form of a reaction mixture as-is, or in the form of a crude product, it can also be isolated from the reaction mixture by a conventional method.

Said "deprotection reaction" can be carried out by an appropriately selected conventional method.

When $P^a$ is an alkyl, for example, Compound (VIII) is subjected to a treatment with an acid (e.g., mineral acid such as hydrobromic acid, or Lewis acid such as titanium tetrachloride).

When $P^a$ is a phenyl-$C_{1-6}$ alkyl, for example, Compound (VIII) is subjected to a hydrogenation reaction.

When $P^a$ is an alkyl-substituted silyl, for example, Compound (VIII) is reacted with a fluoride (e.g., tetrabutylammonium fluoride).

Although Compound (IIIa) obtained can be used for the next reaction in the form of a reaction mixture as-is, or in the form of a crude product, it can also be isolated from the reaction mixture by a conventional method.

Of Compound (III), Compound (IIIb), wherein $R^2$ is a hydrogen atom, can be produced by a commonly known method or a modification thereof, e.g., the method shown by Reaction Formula D below.

Reaction Formula D

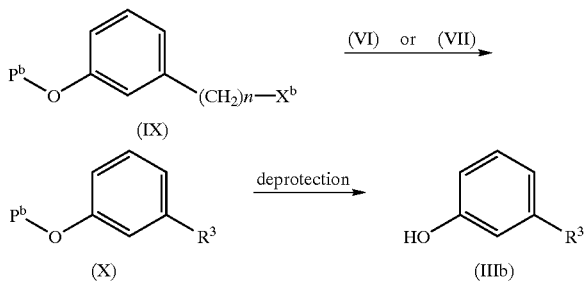

With respect to the formula above, $P^b$ is a hydrogen atom or a protective group; $X^b$ is a leaving group.

The "protective group" represented by $P^b$ is the same as the "protective group" represented by $P^a$ above.

The "leaving group" represented by $X^b$ is, for example, the same as the leaving group represented by X above.

In the same manner as the method described with respect to Reaction Formula C above, Compound (IX) and Compound (VI) or Compound (VII) are condensed to yield Compound (X), which is then subjected to a deprotection reaction as necessary to yield Compound (IIIb).

If available commercially, Compound (IX) may be used as a commercial product as is, or may be produced by a commonly known method, a modification thereof, or the like.

Of Compound (I), Compound (Ia), wherein $R^3$ is a hydrogen atom, can also be produced by the method shown by Reaction Formula E below.

Reaction Formula E

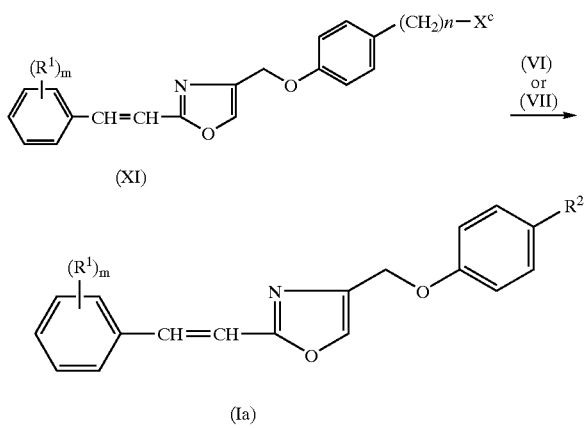

With respect to the formula above, $X^c$ is a leaving group.

The "leaving group" represented by $X^c$ is, for example, the same as the leaving group represented by X above.

Compound (XI) and Compound (VI) or Compound (VII) are reacted to yield Compound (Ia).

This condensation reaction is normally carried out in the presence of a base between Compound (XI) and Compound (VI) or Compound (VII).

Said "base" is exemplified by the base described in detail with respect to Reaction Formula A above.

The amount of "base" used is preferably about 1 to 5 mol per mol of Compound (XI).

The amount of each of Compound (VI) and Compound (VII) used is preferably about 0.5 to 5 mol per mol of Compound (XI).

This reaction is advantageously carried out in the presence of solvent that does not interfere with the reaction. Said solvent is not subject to limitation, as long as the reaction proceeds, and is exemplified by aromatic hydrocarbons, ethers, ketones, halogenated hydrocarbons, amides, sulfoxides, or mixtures of two or more kinds thereof.

The reaction temperature is normally −20 to +150° C., preferably about −10 to +100° C. The reaction time is normally 0.5 to 48 hours.

Compound (XI) can be produced by a commonly known method or a modification thereof, e.g., the method shown by Reaction Formula F below.

Reaction Formula F

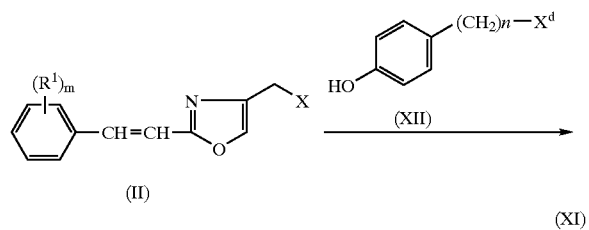

With respect to the formula above, $X^d$ is a leaving group.

The "leaving group" represented by $X^d$ is, for example, the same as the leaving group represented by X above, and is preferably a leaving group which is less reactive than X.

In the same manner as the method described with respect to Reaction Formula A above, Compound (II) and Compound (XII) are reacted to yield Compound (XI).

If available commercially, Compound (XII) may be used as a commercial product as is, or may be produced by a commonly known method, a modification thereof, or the like.

Of Compound (I), Compound (Ib), wherein $R^2$ is a hydrogen atom, can also be produced by the method shown by Reaction Formula G below.

Reaction Formula G

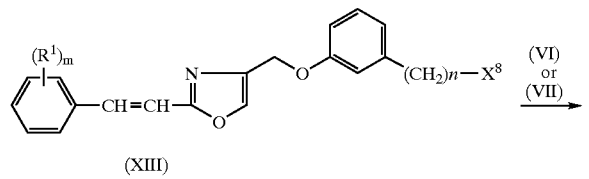

-continued (Ib)

With respect to the formula above, $X^e$ is a leaving group.

The "leaving group" represented by $X^e$ is, for example, the same as the leaving group represented by X above.

In the same manner as the method described with respect to Reaction Formula E above, Compound (XIII) and Compound (VI) or Compound (VII) are reacted to yield Compound (Ib).

Compound (XIII) can be produced by a commonly known method or a modification thereof, e.g., the method shown by Reaction Formula H below.

Reaction Formula H (II) → (XIII)

With respect to the formula above, $X^f$ is a leaving group.

The "leaving group" represented by $X^f$ is, for example, the same as the leaving group represented by X above, and is preferably a leaving group which is less reactive than X.

In the same manner as the method described with respect to Reaction Formula A above, Compound (II) and Compound (XIV) are reacted to yield Compound (XIII).

If available commercially, Compound (XIV) may be used as a commercial product as is, or may be produced by a commonly known method, a modification thereof, or the like.

As the aforementioned "aromatic hydrocarbons," for example, benzene, toluene, xylene, etc. are used.

As the aforementioned "ethers," for example, tetrahydrofuran, dioxane, etc. are used.

As the aforementioned "ketones," for example, acetone, 2-butanone, etc. are used.

As the aforementioned "halogenated hydrocarbons," for example, chloroform, dichloromethane, etc. are used.

As the aforementioned "amides," for example, N,N-dimethylformamide etc. are used.

As the aforementioned "sulfoxides," for example, dimethylsulfoxide etc. are used.

In each reaction mentioned above, if the product is obtained as a free form, it can be converted into a salt thereof by a conventional method; if the product is obtained as a salt, it can be converted into a free form thereof by a conventional method.

In the reactions mentioned above, if amino ($NH_2$), hydroxy (OH), carboxyl (COOH), or the like is contained in a substituent, the starting material may have these groups protected and the protective groups may be removed by a commonly known method after the reaction to produce the desired product. As amino-protecting groups, there may be mentioned acyls (e.g., $C_{1-6}$ alkylcarbonyls such as acetyl; benzyloxycarbonyl; $C_{1-6}$ alkoxy-carbonyls such as tert-butoxycarbonyl; phthaloyl; formyl). As examples of hydroxy-protecting groups, there may be mentioned $C_{1-6}$ alkyls (e.g., methyl, ethyl), phenyl-$C_{1-6}$ alkyls (e.g., benzyl), $C_{1-6}$ alkylcarbonyls (e.g., acetyl), benzoyl, and alkyl-substituted silyls (e.g., trimethylsilyl, tert-butyldimethylsilyl). As examples of carboxyl-protecting groups, there may be mentioned $C_{1-6}$ alkyls (e.g., methyl, ethyl), and phenyl-$C_{1-6}$ alkyls (e.g., benzyl).

Compound (I) [Including (Ia) and (Ib)] thus obtained can be isolated and purified by commonly known means for separation, e.g., concentration, concentration under reduced pressure, solvent extraction, crystallization, recrystallization, re-dissolution, and chromatography.

If Compound (I) is obtained as a free form, it can be converted into a desired salt by a commonly known method or a modification thereof; conversely, if Compound (I) is obtained as a salt, it can be converted into a free form or another desired salt by a commonly known method or a modification thereof.

Compound (I) may be a hydrate or a non-hydrate.

When Compound (I) is obtained as a mixture of optical isomers, the desired (R)-configuration or (S)-configuration can be separated by a commonly known means of optical resolution.

Compound (I) may be labeled with an isotope (e.g., $^3H$, $^{14}C$) or the like.

A compound represented by the formula:

wherein $R^{1a}$ is fluoro or trifluoromethyl, $X^1$ is a leaving group, and n is 3 or 4, or a salt thereof is a new intermediate for producing the compound (I) of the present invention or a salt thereof.

As examples of the "leaving group" represented by $X^1$, there may be mentioned the same examples as those of the "leaving group" represented by X above, and of them, halogen (e.g., chloro, bromo) is preferable.

As the salts of the compound (IIa), the same examples as those of the compound (I) can be used.

A pro-drug of the compound (I) or a salt thereof (hereinafter referred to as the compound (I)) means a compound which is converted to the compound (I) of the present invention under the physiological condition or with a reaction due to an enzyme, an gastric acid, etc. in the living body, that is, a compound which is converted to the compound (I) of the present invention with oxidation, reduction, hydrolysis, etc. according to an enzyme; a compound which is converted to the compound (I) of the present invention with gastric acid, etc.

Examples of the pro-drug of the compound (I) of the present invention include a compound wherein an hydroxy group of the compound (I) of the present invention is substituted with acyl; alkyl, phosphoric acid, boric acid, etc. (e.g. a compound wherein an hydroxy group of the compound (I) of the present invention is substituted with acetyl, palmitoyl, propanoyl, pivaloyl, succinyl, fumaryl, alanyl, dimethylaminomethylcarbonyl, etc.) etc. These pro-drug can be produced by per se known method from the compound (I) of the present invention.

The pro-drug of the compound (I) of the present invention may be a compound which is converted into the compound (I) of the present invention under the physiological conditions as described in "Pharmaceutical Research and Development", Vol. 7 (Drug Design), pages 163–198 published in 1990 by Hirokawa Publishing Co. (Tokyo, Japan).

The compound (I) of the present invention or a salt thereof or a pro-drug thereof (hereinafter referred to as the compound of the present invention) possesses tyrosine kinase-inhibiting activity and can be used to prevent or treat tyrosine kinase-dependent diseases in mammals. Tyrosine kinase-dependent diseases include diseases characterized by increased cell proliferation due to abnormal tyrosine kinase activity. Furthermore, the compound of the present invention or a salt thereof specifically inhibits HER2 tyrosine kinase and is therefore also useful as a therapeutic agent for suppressing the growth of HER2-expressing cancer, or a preventive agent for preventing the transition of hormone-dependent cancer to hormone-independent cancer.

Accordingly, the compound of the present invention can be used as a safe preventive or therapeutic agent for diseases due to abnormal cell proliferation such as various cancers (particularly breast cancer, prostate cancer, pancreatic cancer, gastric cancer, lung cancer, colon cancer, rectal cancer, esophagus cancer, duodenal cancer, cancer of the tongue, cancer of pharynx, cerebral cancer, neurilemoma, non-small cell lung cancer, small cell lung cancer, liver cancer, kidney cancer, cancer of the bile duct, cancer of the uterine body, cancer of the uterine cervix, ovarian cancer, bladder cancer, skin cancer, hemangioma, malignant lymphoma, malignant melanoma, thyroid carcancer, bone tumors, vascular fibroma, retinoblastoma, penile cancer, tumor in childhood, Kaposi's sarcoma, Kaposi's sarcoma derived from AIDS, maxillary tumor, fibrous histiocytoma, leiomyosarcoma, rhabdomyosarcoma, leukemia, etc.), atheroma arteriosclerosis, angiogenesis (e.g., angiogenesis associated with growth of solid cancer and sarcoma, angiogenesis associated with tumor metastasis, and angiogenesis associated with diabetic nephropathy), and viral diseases (HIV infection etc.).

Tyrosine kinase-dependent diseases further include cardiovascular diseases associated with abnormal tyrosine kinase activity. The compound of the present invention can therefore be used as a preventive or therapeutic agent for cardiovascular diseases such as like re-stenosis.

The compound of the present invention is useful as an anticancer agent for preventing or treating cancers, e.g., breast cancer, prostate cancer, pancreatic cancer, gastric cancer, lung cancer, colonic cancer, carcinoma of the colon and rectum. The compound of the present invention is of low toxicity and can be used as a pharmaceutical composition as-is, or in a mixture with a commonly known pharmaceutically acceptable carrier etc. in mammals (e.g., humans, horses, bovines, dogs, cats, rats, mice, rabbits, pigs, monkeys).

In addition to the compound of the present invention, said pharmaceutical composition may contain other active ingredients, e.g., the following hormone therapy agents, chemotherapy agents, immunotherapy agents, or drugs which inhibit the activity of cell growth factors and receptors thereof.

As a pharmaceutical for mammals such as humans, the compound of the present invention can be administered orally in the form of, for example, capsules (including soft capsules and microcapsules), powders, and granules, or non-orally in the form of injections, suppositories, and pellets.

Examples of the parenteral administration route include intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

The dose of the compound varies depending on the route of administration, symptoms, etc. For example, when it is administered orally as an anticancer agent to a patient (body weight 40 to 80 kg) with breast cancer or prostate cancer, its dose is, for example, 0.5 to 100 mg/kg body weight per day, preferably 1 to 50 mg/kg body weight per day, and more preferably 1 to 25 mg/kg body weight per day. This amount may be administered once or in 2 to 3 divided portions daily.

Desired compound of the present invention can be formulated with a pharmaceutically acceptable carrier and administered orally or non-orally in the form of solid preparations such as tablets, capsules, granules and powders; or liquid preparations such as syrups and injectable preparations.

As pharmaceutically acceptable carriers, there may be used various organic or inorganic carrier substances in common use for pharmaceutical preparations, including excipients, lubricants, binders, and disintegrating agents in solid preparations; solvents, dissolution aids, suspending agents, isotonizing agents, buffers, and soothing agents in liquid preparations. Such pharmaceutical additives as antiseptics, antioxidants, coloring agents, and sweetening agents can also be used as necessary.

As examples of preferable excipients, there may be mentioned, for example, lactose, sucrose, D-mannitol, starch, crystalline cellulose, and light silicic anhydride.

As examples of preferable lubricants, there may be mentioned, for example, magnesium stearate, calcium stearate, talc, and colloidal silica.

As examples of preferable binders, there may be mentioned, for example, crystalline cellulose, sucrose, D-mannitol, dextrin, hydroxypropyl cellulose, hydroxypropylmethyl cellulose, and polyvinylpyrrolidone.

As examples of preferable disintegrating agents, there may be mentioned, for example, starch, carboxymethyl cellulose, carboxymethyl cellulose calcium, crosslinked carmellose sodium, and carboxymethyl starch sodium.

As examples of preferable solvents, there may be mentioned, for example, water for injection, alcohol, propylene glycol, macrogol, sesame oil, and corn oil.

As examples of preferable dissolution aids, there may be mentioned, for example, polyethylene glycol, propylene glycol, D-mannitol, benzyl benzoate, ethanol, trisaminomethane, cholesterol, triethanolamine, sodium carbonate, and sodium citrate.

As examples of preferable suspending agents, there may be mentioned, for example, surfactants such as stearyltriethanolamine, sodium lauryl sulfate, laurylaminopropionic acid, lecithin, benzalkonium chloride, benzetonium chloride, and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose, and hydroxypropyl cellulose.

As examples of preferable isotonizing agents, there may be mentioned, for example, sodium chloride, glycerol, and D-mannitol.

As examples of preferable buffers, there may be mentioned, for example, buffer solutions of phosphates, acetates, carbonates, citrates, etc.

As examples of preferable soothing agents, there may be mentioned, for example, benzyl alcohol.

As examples of preferable antiseptics, there may be mentioned, for example, para-oxybenzoic acid esters, chlorobutanol, benzyl alcohol, phenethyl alcohol, dehydroacetic acid, and sorbic acid.

As examples of preferable antioxidants, there may be mentioned, for example, sulfites and ascorbic acid.

A pharmaceutical composition can be produced by a conventional method by containing the compound of the present invention in a ratio of normally 0.1 to 95% (w/w) to the total amount of the preparation, although the ratio varies depending on dosage form, method of administration, carrier, etc.

And, a combination of (1) administering an effective amount of a compound as claimed in claim 1 or a salt thereof or a pro-drug thereof to mammals and (2) 1 to 3 selected from the group consisting (i) administering an effective amount of other anti-cancer agents to mammals, (ii) administering an effective amount of hormonal therapeutic agents to mammals and (iii) non-drug therapy can prevent and/or treat cancer effectively. As the non-drug therapy, for example, surgery, hypertensive chemotherapy, genetherapy, thermotherapy, cryotherapy, laser cauterization, radiotherapy, etc. are exemplified and more than two kinds of these may be combined. For example, the compound of the present invention can be administered to the same subject simultaneously with hormonal therapeutic agents, anticancer agent (e.g., chemotherapeutic agents, immunotherapeutic agents, or drugs that inhibit the activity of growth factors or growth factor receptors)(after here, these are referred to as a combination drug).

Although the compound of the present invention exhibits excellent anticancer action even when used as a simple agent, its effect can be enhanced by using it in combination with one or more of the concomitant drugs mentioned above (multi-agent coadministration).As examples of said "hormonal therapeutic agents," there may be mentioned fosfestrol, diethylstylbestrol, chlorotrianisene, medtoxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimide, LH-RH agonists (e.g., goserelin acetate, buserelin, leuprorelin), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide), 5 α-reductase inhibitors (e.g., finasteride, episteride), adrenocorticohormone drugs (e.g., dexamethasone, prednisolone, betamethasone, triamcinolone), androgen synthesis inhibitors (e.g., abiraterone), and retinoid and drugs that retard retinoid metabolism (e.g., liarozole), etc., and LH-RH agonists (e.g., goserelin acetate, buserelin, leuprorelin) are preferable.

As examples of said "chemotherapeutic agents", there may be mentioned alkylating agents, antimetabolites antagonists, anticancer antibiotics, and plant-derived anticancer agents.

As examples of "alkylating agents", there may be mentioned nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, and bizelesin.

As examples of "antimetabolites", there may be mentioned mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, and ambamustine, etc.

As examples of "anticancer antibiotics", there may be mentioned actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, and idarubicin hydrochloride, etc.

As examples of "plant-derived anticancer agents", there may be mentioned etoposide, etoposide phosphate, vinblastine sulfate, vincristine sulfate, vindesine sulfate, teniposide, paclitaxel, docetaxel, and vinorelbine, etc.

As examples of said "immunotherapeutic agents (BRM)", there may be mentioned picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, and procodazole.

The "growth factor" in said "drugs that inhibit the activity of growth factors or growth factor receptors", there may be mentioned any substances that promote cell proliferation, which are normally peptides having a molecular weight of not more than 20,000 that are capable of exhibiting their activity at low concentrations by binding to a receptor, including (1) EGF (epidermal growth factor) or substances possessing substantially the same activity as it [e.g., EGF, heregulin (HER2 ligand)], (2) insulin or substances possessing substantially the same activity as it [e.g., insulin, IGF (insulin-like growth factor)-1, IGF-2], (3) FGF (fibroblast growth factor) or substances possessing substantially the same activity as it [e.g., acidic FGF, basic FGF, KGF (keratinocyte growth factor), FGF-10, etc.], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor)].

As examples of said "growth factor receptors", there may be mentioned any receptors capable of binding to the aforementioned growth factors, including EGF receptor, heregulin receptor (HER2), insulin receptor-1, insulin receptor-2, IGF receptor, FGF receptor-1 or FGF receptor-2, and the like.

As examples of said "drugs that inhibit the activity of cell growth factor", there may be mentioned Herceptin (HER2 antibody).

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan), topoisomerase II inhibitors (e.g., sobuzoxane), differentiation inducers (e.g., retinoid, vitamin D), angiogenesis inhibitors, α-blockers (e.g., tamsulosin hydrochloride), etc. can be used.

Among those mentioned above, LH-RH agonists (e.g., goserelin acetate, buserelin, leuprorelin), Herceptin (HER2 antibody), etc. are preferable.

In combination of the compound of the present invention and the combination agent of the present invention, the administration time of the compound of the present invention and the combination agent is not restricted, and the compound of the present invention or the combination agent can be administered to an administration subject simultaneously, or may be administered at different times. The dosage of the combination agent may be determined according to the administration amount clinically used, and can be appropriately selected depending on an administration subject, administration route, disease, combination and the like.

The administration mode of the compound of the present invention and the combination agent of the present invention is not particularly restricted, and it is sufficient that the compound of the present invention and the combination agent are combined in administration. Examples of such administration mode include the following methods: (1) The compound of the present invention and the combination agent are simultaneously produced to give a single preparation which is administered. (2) The compound of the present invention and the combination agent are separately produced to give two kinds of preparations which are administered simultaneously by the same administration route. (3) The compound of the present invention and the combination agent are separately produced to give two kinds of preparations which are administered by the same administration route only at the different times. (4) The compound of the present invention and the combination agent are separately produced to give two kinds of preparations which are administered simultaneously by the different administration routes. (5) The compound of the present invention and the combination agent are separately produced to give two kinds of preparations which are administered by the different administration routes only at different times (for example, the compound of the present invention and the combination agent are administered in this order, or in the reverse order). After here, These administration modes are referred to as the combination agent of the present invention.

A combination agent of the present invention has low toxicity, and for example, the compound of the present invention or (and) the above-mentioned combination drug can be mixed, according to a method known per se, with a pharmacologically allowable carrier to give pharmaceutical compositions, for example, tablets (including a sugar-coated tablet, film-coated tablet), powders, granules, capsules (including a soft capsule), solutions, injections, suppositories, sustained release agents and the like which can be safely administered orally or parenterally (e.g., local, rectum, vein, and the like). An injection can be administered by intravenous, intramuscular, subcutaneous or intraorgan route, or directly to the lesion.

As the pharmacologically allowable carrier which may be used in production of the combination agent of the present invention, the same those for the above mentioned pharmaceutical composition of the present invention can be used.

The compounding ratio of the compound of the present invention to the combination drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to 100% by weight, preferably from about 0.1 to 50% by weight, further preferably from about 0.5 to 20% by weight, based on the preparation.

The content of the combination drug in the combination agent of the present invention differs depending on the form of a preparation, and usually from about 0.01 to 100% by weight, preferably from about 0.1 to 50% by weight, further preferably from about 0.5 to 20% by weight, based on the preparation.

The content of additives such as a carrier and the like in the combination agent of the present invention differs depending on the form of a preparation, and usually from about 1 to 99.99% by weight, preferably from about 10 to 90% by weight, based on the preparation.

In the case when the compound of the present invention and the combination drug are separately prepared respectively, the same contents may be adopted.

These preparations can be produced by a method known per se usually used in a preparation process.

For example, the compound of the present invention and the combination drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-oxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and molded into an oily injection.

In the case of a preparation for oral administration, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxypropylcellulose and the like), a lubricant (e.g., talc, magnesium stearate, polyethylene glycol 6000 and the like) and the like, for example, can be added to the compound of the present invention or the combination drug, according to a method known per se, and the mixture can be compression-molded, then if desirable, the molder product can be coated by a method known per se for the purpose of masking of taste, enteric property or durability, to obtain a preparation for oral administration. As this coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose stearate succinate, Eudoragit (methacrylic acid·acrylic acid copolymer, manufactured by Rohm, DE), pigment (e.g., iron oxide red, titanium dioxide, et.) and the like can be used. The preparation for oral administration may be any of a quick release preparation and a sustained release preparation.

For example, in the case of a suppository, the compound of the present invention and the combination drug can be made into an oily or aqueous solid, semisolid or liquid suppository according to a method known per ser. As the oily substrate used in the above-mentioned composition, for example, glycerides of higher fatty acids [e.g., cacao butter, Witebsols (manufactured by Dynamite Novel, DE), etc.], intermediate grade fatty acids [e.g., Myglyols (manufactured by Dynamite Novel, DE), etc.], or vegetable oils (e.g., sesame oil, soy bean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

As the above-mentioned sustained release agent, sustained release microcapsules and the like are listed.

For obtaining a sustained release microcapsule, a method known per se can be adopted, and for example, it is preferably molded into a sustained release preparation shown in the following [2] before administration.

A compound of the present invention is preferably molded into an oral administration preparation such as a solid preparation (e.g., powder, granule, tablet, capsule) and the like, or molded into a rectum administration preparation such as a suppository. Particularly, an oral administration preparation is preferable.

The combination drug can e made into the above-mentioned drug form depending on the kind of the drug.

[1] An injection of the compound of the present invention or the combination drug, and preparation thereof, [2] a sustained release preparation or quick release preparation of the compound of the present invention or the combination drug, and preparation thereof, [3] a sublingual, buccal or intraoral quick integrating agent of the compound of the present invention or the combination drug, and preparation thereof, will be described below specifically.

[1] Injection and Preparation Thereof

An injection prepared by dissolving the compound of the present invention or the combination drug into water is preferable. This injection may be allowed to contain a benzoate and/or salicylate.

The injection is obtained by dissolving the compound of the present invention or the combination drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, organic acid salts such as tromethamol and the like, etc. are listed.

The concentration of the compound of the present invention or the combination drug in an injection is from 0.5 to 50 w/v %, preferably from about 3 to 20 w/v %. The concentration of a benzoate salt or/and salicylate salt is from 0.5 to 50 w/v %, preferably from 3 to 20 w/v %.

Into a preparation of the present invention, additives usually used in an injection, for example, a stabilizer (ascorbic acid, sodium pyrosulfite, and the like), a surfactant (Polysorbate 80, macrogol and the like), a solubilizer (glycerin, ethanol and the like), a buffer (phosphoric acid and alkali metal salt thereof, citric acid and alkali metal salt thereof, and the like), an isotonizing agent (sodium chloride, potassium chloride, and the like), a dispersing agent (hydroxypropylmethylcellulose, dextrin), a pH regulator (hydrochloric acid, sodium hydroxide and the like), a preservative (ethyl p-oxybenzoate, benzoic acid and the like), a dissolving agent (conc. glycerin, meglumine and the like), a dissolution aid (propylene glycol, sucrose and the like), a soothing agent (glucose, benzyl alcohol and the like), and the like, can be appropriately compounded. These additives are generally compounded in a proportion usually used in an injection.

It is advantageous that pH of an injection is controlled from 2 to 12, preferably from 2.5 to 8.0 by addition of a pH regulator.

An injection is obtained by dissolving the compound of the present invention or the combination drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously be heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 minutes.

Further, a preparation endowed with an antibacterial property of a solution may also be produced so that it can be used as a preparation which is divided and administered multiple-times.

[2] Sustained Release Preparation or Quick Release Preparation, and Preparation Thereof A sustained release preparation is preferable which is obtained, if desirable, by coating a nucleus containing the compound of the present invention or the combination drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose ad the like, cellulose esters such as cellulose stearate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacryalte/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacryalte copolymers, poly(methacrylic anhydride), glycidyl methacrylate copolymer, particularly, acrylic acid-based polymers such as Eudoragits (Rhom Farma) such as Eudoragit RS-100, RL-100, RS-30D, RL-30D, RL-PO, RS-PO (ethyl acryalte·methyl methacryalte·trimethyl chloride methacryalte·ammoniumethyl copolymer), Eudoragit NE-30D (methyl methacryalte ethyl acrylate copolymer), and the like, hardened oils such as hardened castor oil (e.g., Lovery wax (Freunt) and the like), waxes such as carnauba wax, fatty acid glycerin ester, paraffin and the like, polyglycerin fatty esters, and the like.

As the swellable polymer, polymers having an acidic dissociating group and showing pH dependent swell are preferable, and polymers manifesting small swelling in acidic regions such as in stomach and large swelling in neutral regions such as in small intestine and large intestine are preferable.

As such a polymer having an acidic dissociating group and showing pH dependent swell, cross-linkable polyacrylic acid copolymers such as, for example, Carbomer 934P, 940, 941, 974P, 980, 1342 and the like, polycarbophil, calcium polycarbophil (last two are manufactured by BF good rich), Hibiswako 103, 104, 105, 304 (all are manufactured by Wako Purechemical Co., Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl group or carboxyalkyl group such as hydroxypropylcellulose, hydroxypropylmethylcellulose, carboxymethylcellulose sodium and the like, methylcellulose, polyvinylpyrrolidone, polyvinyl alcohol, polyethylene glycol and the like.

The content of a water-insoluble substance in the film agent of a sustained release preparation is from about 30 to 90% (w/w), preferably from about 35 to 80% (w/w), further preferably from about 40 to 75% (w/w), the content of a swellable polymer is from about 3 to 30% (w/w), preferably from about 3 to 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to 2000 $\mu$m, further preferably, from about 500 to 1400 $\mu$m.

Preparation of the nucleus can be effected by a usual production method. For example, a suitable excipient, binding agent, integrating agent, lubricant, stabilizer and the like are mixed into a drug, and the mixture is subjected to a wet extrusion granulating method, fluidized bed granulating method or the like, to prepare a nucleus.

The content of drugs in a nucleus is from about 0.5 to 95% (w/w), preferably from about 5.0 to 80% (w/w), further preferably from about 30 to 70% (w/w).

As the excipient contained in the nucleus, for example, saccharides such as sucrose, lactose, mannitol, glucose and the like, starch, crystalline cellulose, calcium phosphate, corn starch and the like a reused. Among them, crystalline cellulose, corn starch are preferable.

As the bonder, for example, polyvinyl alcohol, hydroxypropyl cellulose, polyethylene glycol, polyvinyl pyrrolidone, Pluronic F68, gum Arabic, gelatin, starch and the like are used. As the disintegrating agent, for example, carboxymethylcelulose calcium (ECG505), crosscarmelose sodium (Ac-Di-Sol), crosslinked polyvinylpyrrolidone (Crosspovidone), lower substitution hydroxypropylcellulose (L-HPC) and the like are used. Among them, hydroxypropylcellulose, polyvinylpyrrolidone, lower substitution hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose, waxes can be used, and the average particle size thereof is preferably from about 100 $\mu$m to 1500 $\mu$m.

For separating a drug and a film agent contained in a nucleus, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl group or carboxyalkyl group are used, more preferably, hydroxypropylmethylcellulose and hydroxypropylcellulose are use. The protective agent may contain, as astabilizer, acids such as tartaric acid, citric acid, succinic acid, fumaric acid, maleic acid and the like, and lubricants such as talc and the like. When the protective agent is used, the coating amount is from about 1 to 15% (w/w), preferably from about 1 to 10% (w/w), further preferably from about 2 to 8% (w/w), based on the nucleus.

The protective agent can be coated by a usual coating method, and specifically, the protective agent can be coated, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer and hydrophilic substance in a film agent solution is appropriately selected so that the contents of these components in a coated film are the above-mentioned contents, respectively.

The coating amount of a film agent is from about 1 to 90% (w/w), preferably from about 5 to 50% (w/w), further preferably from about 5 to 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 t 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty ester, hardened castor oil, triethyl citrate, cetyl alcohol, stearyl alcohol and the like may also be added as a plasticizer.

After coating with a film agent, if necessary, an antistatic agent such as talc and the like may be mixed.

The quick release preparation may be liquid (solution, suspension, emulsion and the like) or solid (particle, pill, tablet and the like). Oral agents and parenteral agents such as an injection and the like are used, and oral agents are preferable.

The quick release preparation, usually, may contain, in addition to an active component drug, also carriers, additives and excipients conventionally used in the production field (hereinafter, sometimes abbreviated as excipient). The preparation excipient used is not particularly restricted providing it is an excipient ordinarily used as a preparation excipient. For example, as the expient for an oral solid preparation, lactose, starch, corn starch, crystalline cellulose (Acevil PH101, manufactured by Asahi Chemical Industry Co., Ltd., and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to 99.4 w/w %, preferably from about 20 to 98.5 w/w %, further preferably from about 30 to 97 w/w %, based on the total amount of the quick release preparation.

The content of a drug in the quick release preparation can be appropriately selected in the range from about 0.5 to 95%, preferably from about 1 to 60% based on the total amount of the quick release preparation.

When the quick release preparation is an oral solid preparation, it usually contains, in addition to the above-mentioned components, also an integrating agent. As this integrating agent, there are used, for example, carboxymethylcellulose calcium (ECG-505, manufactured by Gotoku Yakuhin), crosscarmelose sodium (for example, Actisol, manufactured by Asahi Chemical Industry Co., Ltd.), crosspovidone (for example, Colicone CL, manufactured by BASF), lower substitution hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially α-nized starch (PCS, manufactured by Asahi Chemical Industry Co., Ltd.), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and compounding amount of a drug used, design of releasing property, and the like, and for example, from about 0.05 to 30 w/w %, preferably from about 0.5 to 15 w/w %, based on the total amount of the quick releasing agent.

When the quick release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcelllulose, carboxylmethylcellulose, polybinylpyrrolidone, pluran, dextrin and the like), a lubricant (e.g., polyethylene glycol, magnesium stearate, talc, light anhydrous silicic acid (for example, aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene cartor oil derivatives and the like), a coloring agent (e.g., tar coloring matter, caramel, iron oxide red, titanium oxide, riboflavins), if necessary, an appetizing agent (e.g., sweetening agent, arom and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The quick releasing reparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a quick release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Pulek), and the like, then, subjecting the mixture to a wet extrusion granulation method, fluidized bed granulation method and the like.

Thus obtained quick releasing preparation and sustained releasing preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation together with preparation excipients and the like. It may also be permissible that they are made into granules or fine particles, and filled in the same capsule to be used as a preparation for oral administration.

[3] Sublingiual, Buccal or Intraoral Quick Disintegrating Agent and Preparation Thereof Sublinguial, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the combination drug and an excipient is preferable. It may contain also auxiliary agents such as a lubricant, isotonizing agent, hydrophilic carrier, water-dispersible polymer, stabilizer and the like. Further, for easy absorption and increase in in vivo use efficiency, α-cyclodextrin or α-cyclodextrin derivatives (e.g., hydroxypropyl-p-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., fine crystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, plyethylene glycol, polyvinylpyrrolicone, polycarbofil, ascorbate palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublinguial, buccal or intraoral quick disintegrating agent can be produced by mixing the compound of the present invention or the combination drug and an excipient by a method known per se. Further, is desirable, auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the combination drug and the above-mentioned water-dispersible polymer (preferably, hydroxypropylcellulose, hydroxypropylmethylcellulose), excipient and the like are dissolved in a solvent such as water and the like, and the resulted solution is cast, to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbofil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into given area.

As the preferable intraoral quick disintegrating agent, there are listed solid quick scattering dose agents composed of a network body comprising the compound of the present invention or the combination drug, and a water-soluble or water-diffusible carrier which is inert to the compound of the present invention or combination drug, are listed. This network body is obtained by sublimating a solvent from the solid composition constituted of a solution prepared by dissolving the compound of the present invention or the combination drug in a suitable solvent.

It is preferable that the composition of an intraoral quick disintegrating agent contains a matrix forming agent and a secondary component, in addition to the compound of the present invention or the combination drug.

Examples of the matrix forming agent include animal proteins or vegetable proteins such as gelatins, dextrins and, soybean, wheat and psyllium seed protein and the like; rubber substances such as gum Arabic, guar gum, agar, xathane gum and the like; polysaccharides; alginic acids; carboxymethylcelluloses; carageenans; dextrans; pectines; systhetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-asparatic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agent aids to maintain the compound of the present invention or the combination drug in the solution or suspension in diffused condition, in addition to formation of the matrix.

The composition may contain secondary components such as a preservative, antioxidant, surfactant, thickening agent, coloring agent, pH controlling agent, flavoring agent, sweetening agent, food taste masking agent and the like. As the suitable coloring agent, there are listed red, black and yellow iron oxides, and FD & C dyes such as FD & C Blue 2, FD & C Red 40 and the like manufactured by Elis and Eberald. Examples of the suitable flavoring agent include mint, raspberry, licorice, orange, lemon, grape fruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-containing compounds, adsorbent substances and microcapsulated apomorphine.

The preparation contains the compound of the present invention or the combination drug in an amount usually from about 0.1 to 50% by weight, preferably from about 0.1 to 30% by weight, and preferable are preparations (such as the above-mentioned sublingual agent, buccal and the like) which can dissolve 90% or more the compound of the present invention or the combination drug (into water) within the time range of about 1 to 60 minutes, preferably of about 1 to 16 minutes, more preferably of about 2 to 5 minutes, and intraoral quick disintegrating preparations which are disintegrated within the range of 1 to 60 seconds, preferably of 1 to 30 seconds, further preferably of 1 to 10 seconds after place in an oral cavity.

The content of the above-mentioned exipient in the whole preparation is from about 10 to 99% by weight, preferably from about 30 to 90% by weight. The content of β-cyclodextrin or β-cyclodextrin derivative in the whole preparation is from 0 to about 30% by weight. The content of the lubricant in the whole preparation is from about 0.01 to 10% by weight, preferably from about 1 to 5% by weight. The content of the isotonizing agent in the whole preparation is from about 0.1 to 90% by weight, preferably, from about 10 to 70% by weight. The content of the hydrophilic carrier agent in the whole preparation is from about 0.1 to 50% by weight, preferably, from about 10 to 30% by weight. The content of the water-dispersible polymer in the whole preparation is from about 0.1 to 30% by weight, preferably, from about 10 to 25% by weight. The content of the stabilizer in the whole preparation is from about 0.1 to 10% by weight, preferably, from about 1 to 5% by weight. The above-mentioned preparation may further contain additives such as a coloring agent, sweetening agent, preservative and the like, if necessary.

The dosage of a combination agent of the present invention differs depending on the kind of a compound (I), age, body weight, condition, drug form, administration method, administration period and the like, and for example, for one sepsis patient (adult, body weight: about 60 kg), the combination agent is administer intravenously, at a dose of about 0.01 to 1000 mg/kg/day, preferably about 0.01 to 100 mg/kg/day, more preferably about 0.1 to 100 mg/kg/day, particularly about 0.1 to 50 mg/kg/day, especially about 1.5 to 30 mg/kg/day, in terms of the compound of the present invention or the combination drug, respectively, once or several time in division a day. Of course, since the dose as described above varies depending on various conditions, amounts smaller than the above-mentioned dosage may sometimes be sufficient, further, amounts over that range sometimes have to be administered.

The amount of the combination drug can be set at any value unless side effects are problematical. The daily dosage in terms of the combination drug differs depending on the severity, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times in division a day.

In administration of a medicine of the present invention, the compound of the present invention may be administered after administration of the combination drug or the combination drug may be administered after administration of the compound of the present invention, though they may be administered simultaneously. When administered at a time interval, the interval differs depending on the effective ingredient, drug form and administration method, and for example, when the combination drug is administered first, a method in which the compound of the present invention is administered within time range of from 1 minute to 3 days, preferably from 10 minutes to 1 day, more preferably from 15 minutes to 1 hour after administration of the combination drug is exemplified. When the compound of the present invention is administered first, a method in which the combination drug is administered within time range of from 1 minute to 1 day, preferably from 10 minutes to 6 hours, more preferably from 15 minutes to 1 hour after administration of the compound of the present invention is exemplified.

In a preferable administration method, for example, the combination drug which has been formed into an oral administration preparation is administered orally at a daily dose of about 0.001 to 200 mg/kg, and 15 minutes after, the compound of the present invention which has been formed into an oral administration preparation is administered orally at a daily dose of about 0.005 to 100 mg/kg.

In addition, the pharmaceutical composition of the present invention and the combined agent of the present invention can be combined with a non-drug therapy such as (1) surgery, (2) hypertensive chemotherapy using angiotensin II etc., (3) genetherapy, (4) thermotherapy, (5) cryotherapy, (6) laser cauterization, (7) radiotherapy, etc.

For example, the pharmaceutical composition of the present invention and the combined agent of the present invention inhibits an expression of resistance, extend disease-free survival, suppresses cancer metastasis or recurrence, prolongs survival and provides other benefits when used before or after the surgery, etc., or a combination treatment comprising 2 or 3 of these therapies.

Also, treatment with the pharmaceutical composition of the present invention and the combined agent of the present invention can be combined with supportive therapies [e.g., (i) administration of antibiotics (e.g., β-lactams such as pansporin, macrolides such as clarytheromycin) to an combined expression of various infectious diseases, (ii) total parentral nutrition, administration of amino acid preparations and general vitamin preparations for improvement of malnutrition, (iii) morphine administration for pain mitigation, (iv) administration of drugs which mitigate adverse reactions such as nausea, vimoting, anorexia, diarrhea, leukopenia, thrombocytopenia, hemoglobin concentration reduction, hair loss, hepatopathy, renopathy, DIC and fever], (v) administration of drugs for inhibition of multiple drug resistance in cancer].

Preferably, the pharmaceutical composition of the present invention or the combined agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the pharmaceutical composition of the present invention or the combined agent of the present invention before the surgery, etc., for example, it can be administrated 1-time about 30 minutes to 24 hours before the surgery, etc., or in 1 to 3 cycles about 3 months to 6 months before the surgery, etc. In this way, the surgery, etc. can be conducted easily because, for example, a cancer tissue would be reduced by administering the pharmaceutical composition of the present invention or the combined agent of the present invention before the surgery, etc. As a period for administering the pharmaceutical composition of the present invention or the combined agent of the present invention after the surgery, etc., for example, it can be administrated repeatedly per a few weeks to 3 months, about 30 minutes to 24 hours after the surgery, etc. In this way, it makes an effect of the surgery, etc. increasing by administering the pharmaceutical composition of the present invention or the combined agent of the present invention after the surgery, etc. Best Mode for Carrying out of the Invention.

The present invention is hereinafter described in detail by means of, but is not limited to, the following reference examples, working examples, preparation examples and test examples.

In the Reference Examples and Examples, column chromatography was conducted with observation by TLC (thin layer chromatography). In TLC observation, the TLC plate used was the Merck Kieselgel 60$F_{254}$ plate, the developing solvent used was the solvent used as the eluent for column chromatography, and the means of detection used was an UV detector. The silica gel for the column chromatography was also Merck Kieselgel 60$F_{254}$ (70–230 mesh). NMR spectra are shown by proton NMR with tetramethylsilane as the internal standard, using VARIAN Gemini-200 (200 MHz type spectrometer); δ values are expressed in ppm.

The abbreviations used in the Reference Examples and Examples are defined as follows:

| | |
|---|---|
| s | Singlet |
| br | Broad |
| d | Doublet |
| t | Triplet |
| q | Quartet |
| dd | Double doublet |
| dt | Double triplet |
| m | Multiplet |
| J | Coupling constant |
| Hz | Hertz |
| DMF | N,N-dimethylformamide |
| THF | Tetrahydrofuran |

WORKING EXAMPLE

Reference Example 1
4-chloromethyl-2-[(E)-2-(4-methylphenyl)ethenyl]-1,3-oxazole

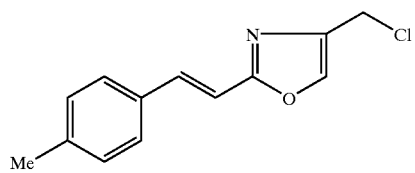

(i) (E)-3-(4-methylphenyl)-2-propenamide

To a solution of 4-methylcinnamic acid (15.19 g) in THF (100 ml), DMF (5 drops) was added; under ice cooling, oxalyl chloride (9.6 ml) was added, followed by stirring at room temperature for 2 hours. After oxalyl chloride (4.0 ml) was added, the reaction mixture was stirred at room temperature for 1 hour, after which it was concentrated to dryness. The residue was dissolved in ethyl acetate (50 ml); under ice cooling, this solution was added drop by drop to a mixture of 25% aqueous ammonia (50 ml)-ethyl acetate (20 ml). The water layer was salted out; the organic layer was extracted with ethyl acetate. The extract was dried over magnesium sulfate, after which it was concentrated under reduced pressure. The precipitate was washed with hexane and diethyl ether to yield the titled compound (11.63 g) as colorless crystals.

$^1$H-NMR (CDCl$_3$) δ: 2.37 (3H, s), 5.56 (2H, brs), 6.41 (1H, d, J=15.8), 7.18 (2H, d, J=8.0), 7.42 (2H, d, J=8.0), 7.62 (1H, d, J=15.8).

IR (KBr): 1671, 1601, 1518, 1397, 1254, 1123, 990, 816 cm$^{-1}$.

(ii) 4-chloromethyl-2-[(E)-2-(4-methylphenyl)ethenyl]-1,3-oxazole

A mixture of (E)-3-(4-methylphenyl)-2-propenamide (8.06 g) and 1,3-dichloroacetone (6.98 g) in toluene (50 ml) were refluxed for 3 hours. After cooling, the reaction mixture was diluted with ethyl acetate, washed with water and saline, and dried over magnesium sulfate, then concentrated under reduced pressure. The residue was purified by silica gel column chromatography (eluent: ethyl acetate-hexane 1:4) to yield the titled compound (8.44 g) as a white crystalline powder.

$^1$H-NMR (CDCl$_3$) δ: 2.38 (3H, s), 4.54 (2H, s), 6.87 (1H, d, J=16.2), 7.20 (2H, d, J=8.2), 7.43 (2H, d, J=8.2), 7.52 (1H, d, J=16.2), 7.62 (1H, s).

IR (KBr): 1642, 1607, 1591, 1537, 1345, 1267, 976, 943, 810 cm$^{-1}$.

Reference Example 2
4-chloromethyl-2-[(E)-2-(4-fluorophenyl)ethenyl]-1,3-oxazole

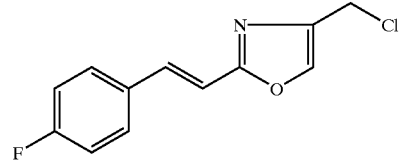

4-fluorocinnamic acid (25 g) was suspended in dichloromethane (300 ml); under ice cooling and stirring, DMF (0.5 ml) and then oxalyl chloride (15.36 ml) were added drop by drop; the same temperature was kept for 3 hours and gradually returned to room temperature. Under reduced pressure, the solvent was distilled off; the residue was dissolved in ethyl acetate (100 ml). This solution was added drop by drop to an ice-cooled mixed solution of 25% aqueous ammonia (250 ml) and ethyl acetate (52.5 ml). The reaction mixture was extracted with ethyl acetate (400 ml×2) and washed with saturated saline, after which it was dried over anhydrous magnesium sulfate. Under reduced pressure, the solvent was distilled off; the precipitated crystal was collected by filtration and dried to yield (E)-3-(4-fluorophenyl)-2-propenamide (24.4 g).

The (E)-3-(4-fluorophenyl)-2-propenamide (17.55 g) thus obtained and 1,3-dichloroacetone (12.85 g) were molten at 130° C. and stirred for 1.5 hours. After the reaction mixture was cooled to room temperature and extracted with ethyl acetate, it was washed with ice water, saturated aqueous sodium bicarbonate, and saturated saline. After drying with anhydrous sodium sulfate, the solvent was distilled off; the residue was purified by column chromatography (eluent: diethyl ether-hexane=1:9→3:17) to yield the titled compound (10.5 g) as colorless crystals.

$^1$H-NMR (CDCl$_3$) δ: 4.54 (2H, s), 6.84 (1H, d, J=16.0 Hz), 7.09 (2H, t, J=8.8 Hz), 7.47–7.55 (3H, m), 7.63 (1H, s).

IR (KBr): 3173, 3133, 3063, 3040, 1645, 1601, 1591, 1537, 1508, 1435, 1416, 1350, 1275, 1233, 1167, 1101, 999 cm$^{-1}$.

Reference Example 3
4-chloromethyl-2-[(E)-2-(4-trifluoromethylphenyl)ethenyl]-1,3-oxazole

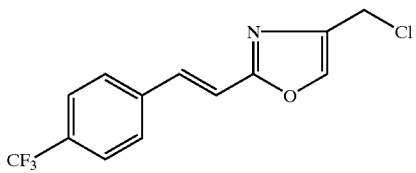

(i) (E)-3-(4-trifluoromethylphenyl)-2-propenamide

To a suspension of 4-trifluoromethylcinnamic acid (19.4 g) and DMF (6 drops) in THF (100 ml), oxalyl chloride (11.7 ml) was added drop by drop at 0° C., followed by stirring at room temperature for 2 hours. After the solvent was distilled off under reduced pressure, the residue was dissolved in ethyl acetate (60 ml) and poured into a mixture of 25% aqueous ammonia-ethyl acetate (5:1, 120 ml). After salting-out, the water layer was extracted with a mixture of ethyl acetate-THF (12:1) (650 ml) and ethyl acetate (100 ml×2) and dried over anhydrous magnesium sulfate. After the solvent was distilled off under reduced pressure, the residue was recrystallized from ethyl acetate-hexane to yield the titled compound (18.0 g) as a colorless tabular crystal.

$^1$H-NMR (CDCl$_3$) δ: 5.58 (2H, br s), 6.53 (1H, d, J=15.8 Hz), 7.63–7.72 (5H, m).

IR (KBr): 3326, 3167, 1686, 1636, 1617, 1404, 1190 cm$^{-1}$.

(ii) 4-chloromethyl-2-[(E)-2-(4-trifluoromethylphenyl)ethenyl]-1,3-oxazole

A solution of (E)-3-(4-trifluoromethylphenyl)-2-propenamide (17.9 g) and 1,3-dichloroacetone (14.8 g) in toluene (83 ml) was refluxed under heating for 9 hours using a Dean-Stark apparatus. After cooling, water was added; the reaction mixture was extracted with ethyl acetate and washed with saturated saline, after which it was dried over anhydrous magnesium sulfate. After the solvent was distilled off under reduced pressure, the residue was purified by silica gel column chromatography (eluent: hexane-methyl acetate=6:1→5:1) to yield the titled compound (15.1 g) as a colorless needle crystal.

$^1$H-NMR (CDCl$_3$) δ: 4.55 (2H, d, J=0.8 Hz), 7.00 (1H, d, J=16.2 Hz), 7.56 (1H, d, J=16.2 Hz), 7.64–7.68 (5H, m).

IR (KBr): 1350, 1325, 1170, 1136, 1113, 1071, 959, 826, 727, 708 cm$^{-1}$.

Reference Example 4
4-chloromethyl-2-[(E)-2-(2,4-difluorophenyl)ethenyl]-1,3-oxazole

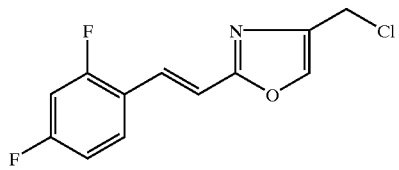

Using (E)-3-(2,4-difluorophenyl)-2-propenamide (9.16 g) and 1,3-dichloroacetone (7.62 g), the same reaction as Reference Example 1-(ii) was carried out to yield the titled compound (6.31 g) as colorless crystals.

$^1$H-NMR (CDCl$_3$) δ: 4.55 (2H, s), 6.8–7.0 (2H, m), 6.96 (1H, d, J=16.8), 7.45–7.7 (3H, m).

Reference Example 5
4-chloromethyl-2-[(E)-2-(2,6-difluorophenyl)ethenyl]-1,3-oxazole

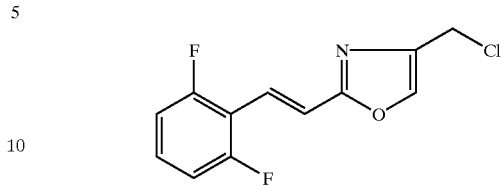

Using (E)-(2,6-difluorophenyl)-2-propenamide (9.0 g) and 1,3-dichloroacetone (7.49 g), the same reaction as Reference Example 1-(ii) was carried out to yield the titled compound (7.18 g) as a light-yellow solid.

$^1$H-NMR (CDCl$_3$) δ: 4.55 (2H, s), 6.85–7.0 (2H, m), 7.2–7.35 (2H, m), 7.55–7.7 (1H, m), 7.66 (1H, s).

Reference Example 6
3-(1H-imidazol-2-yl)-1,2-propanediol

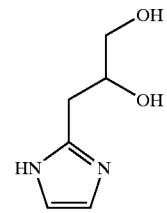

3,4-dihydroxybutyronitrile (30.33 g) was dissolved in absolute methanol (12.2 ml); under ice cooling and stirring, a 5.12 N solution of hydrogen chloride in ether (62 ml) was added under 5° C. The reaction mixture was stirred at constant temperature for 35 hours to yield a double-layered solution. The upper layer was removed, and the lower layer was dissolved in absolute methanol (45 ml). A solution of aminoacetaldehyde dimethylacetal (31.5 g) in absolute methanol (45 ml) was added under ice cooling and stirring under 20° C., followed by stirring for 27 hours. Under reduced pressure, the solvent was distilled off; to the residue, water (57 ml) and concentrated hydrochloric acid (142 ml) were added, followed by stirring at room temperature for 2 hours. Under reduced pressure, the solvent was distilled off; to the residue, an aqueous solution of potassium carbonate was added; after adjustment to pH 10, the solvent was again distilled off. The residue was extracted with ethanol (500 ml) and concentrated to dryness. After purification by silica gel column chromatography, the concentrated extract was desalinized with an ion exchange resin (Amberlyst 15) to yield the titled compound (13.16 g) as pale-brown crystals.

mp 98–100° C.

$^1$H-NMR (DMSO-d$_6$) δ: 2.60 (1H, dd, J=7.6 Hz, 14.8 Hz) 2.80 (1H, dd, J=5.0 Hz, 14.8 Hz), 3.28 (1H, dd, J=5.6 Hz, 10.2 Hz), 3.35 (1H, dd, J=5.4 Hz, 10.2 Hz), 3.72–3.85 (1H, m), 6.88 (2H, s).

IR (KBr): 3167, 3094, 2928, 2656, 1559, 1456, 1416, 1379, 1327, 1291, 1275, 1242, 1202, 1152, 1111, 1092, 1044 cm$^{-1}$.

Reference Example 7
(2R)-3-(1H-imidazol-2-yl)-1,2-propanediol

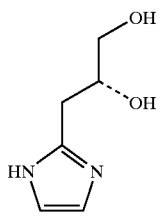

(i) (2R)-1-(benzyloxy)-3-(1-trityl-1H-imidazol-2-yl)-2-propanol

In an argon atmosphere, n-butyllithium (1.6 M solution in hexane, 6.9 ml) was added drop by drop to a solution of 1-tritylimidazole (3.10 g) in THF (80 ml) under ice cooling. After stirring at the same temperature for 30 minutes, (R)-2-[(benzyloxy)methyl]oxirane (1.52 ml) was added. After stirring under ice cooling for 1.5 hours and at room temperature for 1 hour, water was added and the reaction mixture was extracted with ethyl acetate. The extract was washed with water and saline and dried over magnesium sulfate, after which it was concentrated under reduced pressure. The residue was purified by silica gel chromatography (eluent: ethyl acetate-hexane 1:1) to yield the titled compound (1.402 g) as a pale-yellow oily substance.

$^1$H-NMR (CDCl$_3$) δ: 2.06 (2H, dd, J=2.8 Hz, 18.0 Hz) 3.08 (1H, dd, J=5.4 Hz, 9.8 Hz), 3.21 (1H, dd, J=5.4 Hz, 9.8 Hz), 3.55–3.7 (1H, m), 4.36 (2H, s), 6.73 (1H, d, J=1.4 Hz), 6.93 (1H, d, J=1.4 Hz), 7.0–7.4 (20H, m).

(ii) (2R)-1-(benzyloxy)-3-(1H-imidazol-2-yl)-2-propanol

To a solution of (2R)-1-(benzyloxy)-3-(1-trityl-1H-imidazol-2-yl)-2-propanol (1.40 g) in acetone (8 ml), 1 N hydrochloric acid (8 ml) was added, followed by stirring at 50° C. for 1 hour. Additionally, 1 N hydrochloric acid (8 ml) was added, followed by stirring at 50° C. for 2 hours. After concentration and addition of water, the reaction mixture was twice washed with diethyl ether. After neutralization with aqueous sodium bicarbonate, the water layer was extracted with ethyl acetate and washed with saline, after which it was dried over magnesium sulfate and concentrated under reduced pressure. The residue was purified by silica gel column chromatography (eluent:ethyl acetate-methanol=10:1) to yield the titled compound (424 mg) as a colorless oily substance.

$^1$H-NMR (CDCl$_3$) δ: 2.85 (1H, dd, J=7.8 Hz, 15.6 Hz), 2.99 (1H, dd, J=3.6 Hz, 15.6 Hz), 3.39 (1H, dd, J=7.0 Hz, 9.5 Hz), 3.52 (1H, dd, J=4.4 Hz, 9.5 Hz), 4.1–4.3 (1H, m), 4.55 (2H, s), 6.94 (2H, s), 7.3–7.45 (5H, m).

(iii) (2R)-3-(1H-imidazol-2-yl)-1,2-propanediol

To a solution of (2R)-1-(benzyloxy)-3-(1H-imidazol-2-yl)-2-propanol (424 mg) in methanol (10 ml), 10% palladium carbon (50% hydrated, 85 mg) was added, followed by stirring at 50–60° C. in a hydrogen atmosphere for 2 days. The catalyst was filtered off; the filtrate was concentrated to yield the titled compound (254 mg) as a white solid.

$^1$H-NMR (CDCl$_3$) δ: 2.58 (1H, dd, J=7.6 Hz, 14.6 Hz), 2.78 (1H, dd, J=5.2 Hz, 14.6 Hz), 3.17 (1H, d, J=5.2 Hz), 3.2–3.3 (1H, m), 3.7–3.85 (1H, m), 4.6–4.7 (1H, m), 4.86 (1H, d, J=4.8 Hz), 6.76 (1H, brs), 6.95 (1H, brs).

$[\alpha]_D^{22}$=+2.5° (C=1.0, methanol)

Reference Example 8
(2S)-3-(1H-imidazol-2-yl)-1,2-propanediol

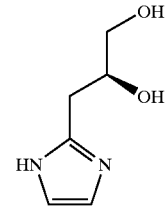

(i) (3S)-4-(benzyloxy)-3-(trimethylsilyloxy)butyronitrile

To a mixture of (2S)-2-[(benzyloxy)methyl]oxirane (6.57 g) and trimethylsilanecarbonitrile (5.0 g), potassium cyanide (26 mg) and 18-crown-6 (106 mg) were added, followed by refluxing at 135° C. in an argon atmosphere for 75 minutes. After cooling, the reaction mixture was subjected to distillation under reduced pressure to yield the titled compound (7.42 g).

$^1$H-NMR (CDCl$_3$) δ: 0.15 (9H, s), 2.52 (1H, dd, J=6.6 Hz, 16.6 Hz), 2.65 (1H, dd, J=4.6 Hz, 16.6 Hz), 3.39 (1H, dd, J=6.8 Hz, 9.6 Hz), 3.50 (1H, dd, J=4.8 Hz, 9.6 Hz), 4.01–4.14 (1H, m), 4.52 (2H, s), 7.26–7.44 (5H, m).

IR (neat): 3065, 3032, 2957, 2903, 2865, 2251, 1607, 1588, 1497, 1454, 1416, 1366, 1254, 1209, 1117, 1001 cm$^{-1}$.

(ii) (3S)-4-(benzyloxy)-3-hydroxybutyronitrile (3S)-4-(benzyloxy)-3-[(trimethylsilyl)oxy]tyronitrile (7.41 g) was dissolved in tetrahydrofuran (28.2 ml); under ice cooling and stirring, a 1 M solution of tetrabutylammonium fluoride in THF (28.2 ml) was added, followed by stirring for 1.5 hours. Under reduced pressure, the solvent was distilled off, the residue was dissolved in ether and washed with water and saturated saline. Under reduced pressure, the solvent was distilled off; the residue was purified by silica gel column chromatography to yield the titled compound (4.58 g) as a colorless oily substance.

$^1$H-NMR (DMSO-d$_6$) δ: 2.56 (1H, dd, J=6.4 Hz, 16.8 Hz) 2.70 (1H, dd, J=4.6 Hz, 16.8 Hz), 3.34 (1H, dd, J=6.2 Hz, 9.8 Hz), 3.44 (1H, dd, J=5.4 Hz, 9.8 Hz), 3.85–3.95 (1H, m), 5.52 (2H, d, J=5.2 Hz), 7.25–7.40 (5H, m).

IR (neat): 3600–3200, 3065, 3032, 2867, 2253, 1605, 1586, 1497, 1454, 1416, 1364, 1308, 1254, 1208, 1101, 1078 cm$^{-1}$.

(iii) (2S)-1-(benzyloxy)-3-(1H-imidazol-2-yl)-2-propanol

Using (3S)-4-(benzyloxy)-3-hydroxybutyronitrile (6.51 g), a 5.12 N solution of hydrogen chloride in ether (7.0 ml), and aminoacetaldehyde dimethyl acetal (3.58 g), the same reaction as Reference Example 6 was carried out to yield the titled compound (2.22 g) as a light-brown oily substance.

$^1$H-NMR (CDCl$_3$) δ: 2.84 (1H, dd, J=7.8 Hz, 15.4 Hz), 2.97 (1H, dd, J=3.6 Hz, 15.4 Hz), 3.41 (1H, dd, J=6.8 Hz, 9.4 Hz), 3.51 (1H, dd, J=4.4 Hz, 9.4 Hz), 4.11–4.23 (1H, m), 4.54 (2H, s), 6.91 (2H, s), 7.27 (5H, m).

IR (neat): 3400–3140, 3065, 3032, 2903, 2865, 1601, 1557, 1495, 1454, 1427, 1366, 1312, 1206, 1101, 1028 cm$^{-1}$.

$[\alpha]_D^{22}$=−2.30 (C=1.04, methanol)

(iv) (2S)-3-(1H-imidazol-2-yl)-1,2-propanediol (2S)-1-(benzyloxy)-3-(1H-imidazol-2-yl)-2-propanol (1.725 g) was dissolved in ethanol (30 ml); 10% palladium carbon (1.04 g) was added, followed by vigorous stirring in a hydrogen atmosphere at 60° C. and 5 atm for 24 hours. The catalyst was filtered off and the solvent was distilled off; the residue was purified by silica gel flush column chromatography to yield the titled compound (0.945 g).

The spectral data ($^1$H-NMR, IR) of this product agreed with those of the compound of Reference Example 6.

Reference Example 9

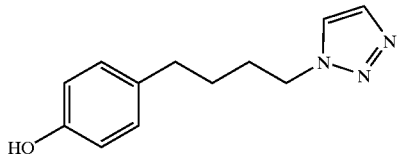

(i) 4-(4-benzyloxyphenyl)-3-buten-1-ol

In an argon atmosphere, 3-hydroxypropyltriphenylphosphonium bromide (4.02 g) was suspended in dehydrated THF (30 ml); 60% oily sodium hydride (0.4 g) was added, followed by refluxing for 3 hours. To the reaction mixture, a solution of 4-benzyloxybenzaldehyde (2.12 g) in dehydrated THF (7 ml) was added drop by drop, followed by refluxing for 67 hours. After cooling, the insoluble matter was filtered off; the filtrate was concentrated under reduced pressure. The residue was purified by column chromatography (eluent: hexane-ethyl acetate=9:1→4:1) to yield the titled compound (1.76 g) as colorless crystals.

$^1$H-NMR (CDCl$_3$) δ: 2.46 (0.8H, dq, J=1.4 Hz, 6.2 Hz) 2.61 (1.2H, dq, J=1.6 Hz, 6.4 Hz), 3.71–3.78 (2H, m), 5.06 (1.2H, s), 5.07 (1.8H, s), 5.59 (0.6H, dt, J=7.2 Hz, 11.6 Hz), 6.07 (0.4H, dt, J=7.2 Hz, 15.8 Hz), 6.45 (0.4H, d, J=15.8 Hz), 6.52 (0.6H, d, J=11.6 Hz), 6.89–6.98 (2H, m), 7.22–7.46 (7H, m).

IR (KBr): 3279, 3063, 3036, 3011, 2911, 2867, 1607, 1574, 1510, 1470, 1454, 1383, 1302, 1250, 1177, 1117, 1053, 1017 cm$^{-1}$.

(ii) 4-(4-hydroxybutyl)phenol 4-(4-benzyloxyphenyl)-3-buten-1-ol (1.70 g) was dissolved in a mixture of methanol-THF (1:1, 20 ml); 10% palladium carbon (0.17 g) was added, followed by vigorous stirring in a hydrogen atmosphere for 1.5 hours. The catalyst was filtered off; the filtrate was concentrated under reduced pressure to yield the titled compound (1.1 g) as a colorless crystalline powder.

$^1$H-NMR (CDCl$_3$) δ: 1.50–1.76 (4H, m), 2.57 (2H, t, J=7.1 Hz), 3.67 (2H, t, J=6.2 Hz), 6.74 (2H, d, J=8.4 Hz), 7.03 (2H, d, J=8.4 Hz).

IR (KBr): 3500–3100, 3025, 2940, 2859, 1615, 1597, 1514, 1456, 1362, 1240, 1173, 1107, 1055, 1024 cm$^{-1}$.

(iii) 4-[4-(benzyloxy)phenyl]-1-butanol

In an argon atmosphere, dry DMF (115 ml) was added to 4-(4-hydroxybutyl)phenol (9.43 g) and 65% oily sodium hydride (2.4 g), followed by stirring for 15 minutes. Next, under ice cooling and stirring, a solution of benzyl bromide (9.87 g) in dry dimethylformamide (29.5 ml) was added drop by drop, followed by stirring at the same temperature for 2 hours. After ice water and a 1 N solution of potassium hydrogen sulfate were added, the reaction mixture was extracted with ethyl acetate. The organic layer was washed with saturated saline, after which it was dried with anhydrous sodium sulfate. The solvent was distilled off under reduced pressure; the residue was purified by silica gel column chromatography to yield the titled compound (10.67 g) as a colorless crystalline powder.

$^1$H-NMR (DMSO-d$_6$) δ: 1.34–1.64 (4H, m), 2.50 (2H, t, J=7.0 Hz), 3.39 (2H, dt, J=5.2 Hz, 6.4 Hz), 4.34 (1H, t, J=5.2 Hz), 5.05 (2H, s), 6.90 (2H, d, J=8.6 Hz), 7.09 (2H, d, J=8.6 Hz), 7.28–7.47 (5H, m).

IR (KBr): 3500–3200, 3048, 3036, 2928, 2907, 2861, 2840, 1615, 1582, 1514, 1472, 1454, 1379, 1360, 1298, 1285, 1250, 1175, 1119, 1063, 1012 cm$^{-1}$.

(iv) 4-[4-(benzyloxy)phenyl]butyl Methanesulfonate

To a solution of 4-(4-benzyloxyphenyl)butanol (10 g) in ethyl acetate (390 ml), triethylamine (8.16 ml) and methanesulfonyl chloride (4.53 ml) were added drop by drop under ice cooling. After stirring at the ice cooling temperature for 30 minutes and at room temperature for 1 hour, the reaction mixture was washed with ice water and saturated saline. After drying with anhydrous sodium sulfate, the solvent was distilled off under reduced pressure to yield the titled compound (14 g) as an oily substance. This product was used for the next process without purification.

$^1$H-NMR (CDCl$_3$) δ: 1.64–1.86 (4H, m), 2.60 (2H, t, J=7.1 Hz), 2.98 (3H, s), 4.23 (2H, t, J=6.1 Hz), 5.05 (2H, s), 6.91 (2H, d, J=8.8 Hz), 7.09 (2H, d, J=8.8 Hz), 7.32–7.48 (5H, m).

IR (neat): 3063, 3031, 2940, 2865, 1611, 1584, 1512, 1456, 1354, 1337, 1240, 1175, 1115, 1015 cm$^{-1}$.

(v) Benzyl 4-(4-iodobutyl)phenyl Ether

Sodium iodide (29.25 g) was dissolved in acetone (195 ml); 4-[4-(benzyloxy)phenyl]butyl methanesulfonate (13 g) was added, followed by refluxing at 80° C. for 1.5 hours. After cooling, the solvent was distilled off; to the residue, ethyl acetate (750 ml) was added; the mixture was washed sequentially with water, an aqueous solution of sodium thiosulfate, and saturated saline. The organic layer was dried over anhydrous magnesium sulfate; the solvent was distilled off under reduced pressure to yield the titled compound (14.29 g) as an oily substance. This product was used for the next process without purification.

$^1$H-NMR (CDCl$_3$) δ: 1.63–1.93 (4H, m), 2.57 (2H, t, J=7.3 Hz), 3.19 (2H, t, J=6.8 Hz), 5.04 (2H, s), 6.90 (2H, d, J=8.8 Hz), 7.09 (2H, d, J=8.8 Hz), 7.30–7.47 (5H, m).

IR (neat): 3063, 3031, 2932, 2857, 1611, 1582, 1510, 1454, 1381, 1298, 1238, 1175, 1121, 1026 cm$^{-1}$.

(vi) 1-[4-(4-benzyloxyphenyl)butyl]-1H-1,2,3-triazole

Benzyl 4-(4-iodobutyl)phenyl ether (1.1 g), 1H-1,2,3-triazole (0.31 g), and potassium carbonate (0.622 g) were suspended in DMF (7.5 ml), followed by stirring at 70° C. for 26.5 hours. After cooling, the reaction mixture was extracted with ethyl acetate and washed with water and saturated saline. Under reduced pressure, the solvent was distilled off; the residue was subjected to silica gel column chromatography (eluent: hexane-ethyl acetate=4:1→2:3) to yield the titled compound (0.391 g).

$^1$H-NMR (CDCl$_3$) δ: 1.61 (2H, quintet, J=7.8 Hz), 1.93 (2H, quintet, J=7.8 Hz), 2.59 (2H, t, J=7.6 Hz), 4.39 (2H, t, J=7.1 Hz), 5.04 (2H, s), 6.90 (2H, d, J=8.8 Hz), 7.06 (2H, d, J=8.8 Hz), 7.30–7.48 (5H, m), 7.49 (1H, s), 7.69 (1H, s).

(KBr): 3106, 3034, 2940, 2861, 1611, 1582, 1512, 1454, 1387, 1298, 1244, 1177, 1113, 1080, 1040, 1028 cm$^{-1}$.

(vii) 4-[4-(1H-1,2,3-triazol-1-yl)butyl]phenol

1-[4-(4-benzyloxyphenyl)butyl]-1H-1,2,3-triazole (0.38 g) was dissolved in methanol (7.6 ml); 10% palladium carbon (0.1 g) was added, followed by vigorous stirring in a hydrogen atmosphere for 14 hours. The catalyst was filtered off; the filtrate was concentrated to dryness under reduced pressure to yield the titled compound (0.268 g) as a crystalline powder.

$^1$H-NMR (CDCl$_3$) δ: 1.60 (2H, quintet, J=7.0 Hz), 1.93 (2H, quintet, J=7.4 Hz), 2.57 (2H, t, J=7.5 Hz), 4.40 (2H, t, J=7.0 Hz), 6.79 (2H, d, J=8.6 Hz), 6.99 (2H, d, J=8.6 Hz), 7.51 (1H, s), 7.71 (1H, s).

IR (KBr): 3148, 3129, 3017, 2946, 2861, 2814, 1615, 1593, 1514, 1462, 1381, 1269, 1242, 1225, 1123, 1078 cm$^{-1}$.

Reference Example 10
4-[3-(1H-1,2,3-triazol-1-yl)propyl]phenol

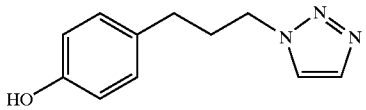

Benzyl 4-(3-iodopropyl)phenyl ether (2.47 g), 1H-1,2,3-triazole (629 mg), and potassium carbonate (1.26 g) were suspended in DMF (17.5 ml), followed by stirring at 70° C. for 18.5 hours. The reaction mixture was returned to room temperature and extracted with ethyl acetate, after which it was washed with water and saturated saline. Under reduced pressure, the solvent was distilled off; the residue was purified by silica gel column chromatography (eluent: hexane-ethyl acetate=4:1→2:3) to yield 1-[3-(4-benzyloxyphenyl)propyl]-1H-1,2,3-triazole (856 mg).

$^1$H-NMR (CDCl$_3$) δ: 2.23 (2H, quintet, J=7.2 Hz), 2.60 (2H, t, J=7.5 Hz), 4.38 (2H, t, J=7.1 Hz), 5.05 (2H, s), 6.92 (2H, d, J=8.8 Hz), 7.10 (2H, d, J=8.8 Hz), 7.30–7.48 (5H, m), 7.52 (1H, s), 7.72 (1H, s).

IR (KBr): 3100, 3030, 2960, 2926, 2860, 1613, 1585, 1514, 1454, 1383, 1298, 1250, 1215, 1177, 1115, 1082, 1044, 1028, 1019 cm$^{-1}$.

1-[3-(4-benzyloxyphenyl)propyl]-1H-1,2,3-triazole (850 mg) was dissolved in methanol (29 ml); 10% palladium carbon (0.1 g) was added, followed by vigorous stirring in a hydrogen atmosphere for 13 hours. The catalyst was filtered off; the filtrate was concentrated to dryness under reduced pressure to yield the titled compound (600 mg) as a crystalline powder.

$^1$H-NMR (CDCl$_3$) δ: 2.22 (2H, quintet, J=7.0 Hz), 2.56 (2H, t, J=7.0 Hz), 4.38 (2H, t, J=7.0 Hz), 6.87 (2H, d, J=8.6 Hz), 7.04 (2H, d, J=8.6 Hz), 7.55 (1H, s), 7.74 (1H, s).

IR (KBr): 3127, 3100, 3015, 2932, 1615, 1595, 1516, 1456, 1373, 1244, 1223, 1175, 1121, 1080, 1038 cm$^{-1}$.

Reference Example 11
3-[3-(1H-1,2,3-triazol-1-yl)propyl]phenol

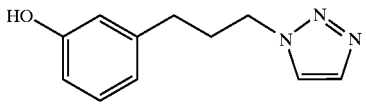

(i) 3-[3-(benzyloxy)phenyl]-1-propanol

In an argon stream, 3-benzyloxybenzaldehyde (21.3 g) and diethylphosphonoethyl acetate (23.6 g) were suspended in dry DMF (250 ml). Under ice cooling and stirring, 65% oily sodium hydride (3.88 g) was added little by little; after completion of this addition, the mixture was stirred at room temperature for 2 hours. After the solvent was distilled off, the residue was dissolved in ethyl acetate and washed with water and saturated saline, after which it was dried over anhydrous sodium sulfate. Under reduced pressure, the solvent was distilled off to yield 33.15 g of a crude product of ethyl (E)-3-[3-(benzyloxy)phenyl]-2-propenate as an oily substance. This product was dissolved in ethanol (406 ml); ethylenediamine-treated 5% palladium carbon [Pd—C (en), 2.7 g] was added, followed by vigorous stirring in a hydrogen atmosphere. Hydrogen (1.75 L) was consumed to complete hydrogenation, and the catalyst was filtered off. Under reduced pressure, the solvent was distilled off; the residue was dissolved in dehydrated THF (120 ml). This solution was added drop by drop to a mixture of lithium aluminum hydride (4.61 g) suspended in dehydrated THF (120 ml) under ice cooling. The reaction mixture was stirred under ice cooling for 1.5 hours and at room temperature for 1 hour. The reaction mixture was added to ice water and acidified, after which it was extracted with ethyl acetate, washed with water and saturated saline, after which it was dried over anhydrous sodium sulfate. Under reduced pressure, the solvent was distilled off; the residue was purified by silica gel column chromatography to yield the titled compound (14.39 g) as a colorless oily substance.

$^1$H-NMR (CDCl$_3$) δ: 1.80–1.96 (2H, m), 2.69 (2H, t, J=7.7 Hz), 3.66 (2H, t, J=6.4 Hz), 5.05 (2H, s), 6.77–6.87 (3H, m), 7.20 (1H, t, J=8.0 Hz), 7.28–7.48 (5H, m).

IR (neat): 3330, 3063, 3032, 2940, 2867, 1599, 1582, 1487, 1453, 1381, 1314, 1258, 1155, 1026 cm$^{-1}$.

(ii) 3-[3-(benzyloxy)phenyl]propyl methanesulfonate

Using 3-(3-benzyloxyphenyl)propanol (13.5 g), triethylamine (8.16 ml) and methanesulfonyl chloride(4.53 ml), the same reaction as Reference Example 9-(iv) was carried out to yield the titled compound (19.7 g) as an oily substance.

$^1$H-NMR (CDCl$_3$) δ: 2.00–2.15 (2H, m), 2.73 (2H, t, J=7.5 Hz), 2.98 (3H, s), 4.22 (2H, t, J=6.3 Hz), 5.06 (2H, s), 6.77–6.88 (3H, m), 7.22 (1H, t, J=7.7 Hz), 7.31–7.48 (5H, m).

IR (neat): 3032, 2940, 2870, 1599, 1584, 1487, 1453, 1381, 1354, 1260, 1175, 1026 cm$^{-1}$.

(iii) Benzyl 3-(3-iodopropyl)phenyl Ether

Using 3-[3-(benzyloxy)phenyl]propyl methanesulfonate (19.7 g) and sodium iodide (29.25 g), the same reaction as Reference Example 9-(v) was carried out to yield the titled compound (18.4 g) as an oily substance.

$^1$H-NMR (CDCl$_3$) δ: 2.11 (2H, quintet, J=7.3 Hz), 2.70 (2H, t, J=7.2 Hz), 3.16 (2H, t, J=6.8 Hz), 5.06 (2H, s), 6.78–6.87 (3H, m), 7.21 (1H, t, J=7.2 Hz), 7.32–7.48 (5H, m).

IR (neat): 3063, 3031, 2934, 2861, 1599, 1582, 1487, 1451, 1381, 1316, 1258, 1213, 1155, 1080, 1028 cm$^{-1}$.

(iv) 1-[3-(3-benzyloxyphenyl)propyl]-1H-1,2,3-triazole

In an argon atmosphere, 1H-1,2,3-triazole (0.9 g) was dissolved in DMF (20 ml); 65% oily sodium hydride (0.48 g) was added. After stirring for 30 minutes, a solution of benzyl 3-(3-iodopropyl)phenyl ether (3.53 g) in DMF (5 ml) was added, followed by stirring at room temperature for 19 hours. The reaction mixture was diluted with ethyl acetate and washed with water and saturated saline. Under reduced pressure, the solvent was distilled off; the residue was subjected to column chromatography to yield the titled compound (1.1 g) as colorless crystals.

mp 74–75° C.

$^1$H-NMR (CDCl$_3$) δ: 2.25 (2H, quintet, J=7.2 Hz), 2.63 (2H, t, J=7.3 Hz), 4.37 (2H, t, J=7.1 Hz), 5.05 (2H, s), 6.75–6.88 (3H, m), 7.23 (1H, t, J=8.2 Hz), 7.31–7.47 (5H, m), 7.49 (1H, d, J=1.0 Hz), 7.71 (1H, d, J=1.0 Hz).

IR (KBr): 3125, 3063, 3032, 2944, 2867, 1599, 1584, 1487, 1453, 1381, 1316, 1260, 1215, 1157, 1113, 1074, 1028 cm$^{-1}$.

(v) 3-[3-(1H-1,2,3-triazol-1-yl)propyl]phenol

To a solution of 1-[3-(3-benzyloxyphenyl)propyl]-1H-1,2,3-triazole (0.937 g) in methanol (32 ml), 10% palladium carbon (0.1 g) was added, followed by vigorous stirring in a hydrogen atmosphere at room temperature for 8 hours. The catalyst was filtered off; the filtrate was concentrated to dryness under reduced pressure to yield the titled compound (0.593 g) as colorless crystals.

mp 85–86° C.

$^1$H-NMR (CDCl$_3$) δ: 2.24 (2H, quintet, J=7.1 Hz), 2.60 (2H, t, J=7.5 Hz), 4.38 (2H, t, J=7.1 Hz), 6.68–6.79 (3H, m), 6.96 (1H, s), 7.16 (1H, t, J=8.1 Hz), 7.54 (1H, d, J=1.0 Hz), 7.73 (1H, d, J=1.0 Hz).

IR (KBr): 3129, 3077, 3054, 2949, 2863, 2722, 2614, 1599, 1588, 1483, 1458, 1362, 1337, 1281, 1221, 1157, 1121, 1080, 1038 cm$^{-1}$.

Reference Example 12

4-{4-[2-(2-hydroxyethyl)-1H-imidazol-1-yl]butyl}phenol

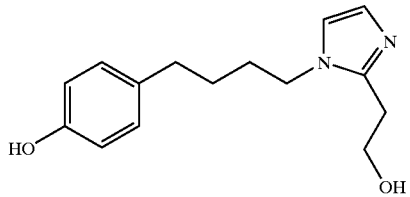

(i) 2-(1-{4-[4-(benzyloxy)phenyl]butyl}-1H-imidazol-2-yl)-1-ethanol

Benzyl 4-(4-iodobutyl)phenyl ether (14.29 g), 2-(2-hydroxyethyl)imidazole (13.1 g), and potassium carbonate (5.39 g) were stirred in DMF (390 ml) at 60° C. for 16 hours. After cooling, the insoluble matter was filtered off; the filtrate was concentrated under reduced pressure. The residue was dissolved in ethyl acetate and washed with water and saturated saline. Under reduced pressure, the solvent was distilled off; the residue was purified by column chromatography (eluent: ethyl acetate-methanol=19:1→9:1). The eluate was recrystallized from ethyl acetate-methanol to yield the titled compound (10.99 g) as colorless crystals.

mp 75–77° C.

$^1$H-NMR (CDCl$_3$) δ: 1.53–1.82 (4H, m), 2.58 (2H, t, J=7.1 Hz), 2.78 (2H, t, J=5.5 Hz), 3.81 (2H, t, J=6.9 Hz), 4.03 (2H, t, J=5.5 Hz), 5.04 (2H, s), 6.80 (1H, d, J=1.2 Hz), 6.90 (2H, d, J=8.6 Hz), 6.93 (1H, d, J=1.2 Hz), 7.05 (2H, d, J=8.6 Hz), 7.34–7.47 (5H,

IR (KBr): 3144, 3032, 2934, 2859, 1611, 1582, 1514, 1495, 1456, 1431, 1381, 1298, 1273, 1244, 1175, 1150, 1121, 1109, 1051, 1026 cm$^{-1}$.

(ii) 4-{4-[2-(2-hydroxyethyl)-1H-imidazol-1-yl]butyl}phenol

Using 2-(1-{4-[4-(benzyloxy)phenyl]butyl}-1H-imidazol-2-yl)-1-ethanol (10.67 g) and 10% palladium carbon (1.6 g), the same reaction as Reference Example 11-(v) was carried out to yield the titled compound (5.3 g).

mp 118–119° C.

$^1$H-NMR (CDCl$_3$) δ: 1.50–1.80 (4H, m), 2.55 (2H, t, J=7.0 Hz), 2.79 (2H, t, J=5.8 Hz), 3.82 (2H, t, J=7.0 Hz), 3.97 (2H, t, J=5.8 Hz), 3.85–4.40 (1H, br), 6.77 (2H, d, J=8.4 Hz), 6.80 (1H, s), 6.94 (1H, s), 6.96 (2H, d, J=8.4 Hz).

IR (KBr): 3600–2400, 1615, 1593, 1516, 1489, 1456, 1373, 1252, 1171, 1150, 1125, 1103, 1055 cm$^{-1}$.

Reference Example 13

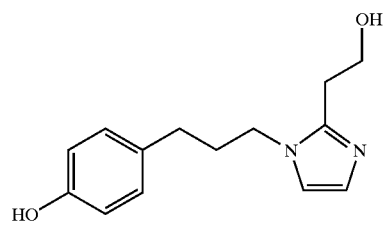

(i) 2-(1-{3-[4-(benzyloxy)phenyl]propyl}-1H-imidazol-2-yl)-1-ethanol

Using benzyl 4-(3-iodopropyl)phenyl ether (5.28 g), 2-(2-hydroxyethyl)imidazole (5.05 g) and potassium carbonate (2.07 g), the same reaction as Reference Example 12-(i) was carried out to yield the titled compound (2.78 g) as colorless crystals.

mp 80–82° C.

$^1$H-NMR (CDCl$_3$) δ: 2.03 (2H, quintet, J=7.4 Hz), 2.58 (2H, t, J=7.4 Hz), 2.74 (2H, t, J=5.6 Hz), 3.82 (2H, t, J=7.4 Hz), 4.01 (2H, t, J=5.6 Hz), 5.05 (2H, s), 6.83 (1H, s), 6.92 (2H, d, J=8.6 Hz), 6.94 (1H, s), 7.07 (2H, d, J=8.6 Hz), 7.32–7.47 (5H, m).

IR (KBr): 3500–3100, 3110, 3063, 3032, 2934, 2865, 1611, 1584, 1512, 1495, 1454, 1381, 1298, 1240, 1177, 1152, 1121, 1057, 1024 cm$^{-1}$.

(ii) 4-{3-[2-(2-hydroxyethyl)-1H-imidazol-1-yl]propyl}phenol

Using 2-(1-{3-[4-(benzyloxy)phenyl]propyl}-1H-imidazol-2-yl)-1-ethanol (2.53 g) and 10% palladium carbon (0.38 g), the same reaction as Reference Example 11-(v) was carried out to yield the titled compound (1.85 g) as colorless crystals.

mp 116–117° C.

$^1$H-NMR (CDCl$_3$+CD$_3$OD) δ: 2.03 (2H, quintet, J=7.3 Hz), 2.55 (2H, t, J=7.3 Hz), 2.75 (2H, t, J=6.2 Hz), 3.83 (2H, t, J=7.3 Hz), 3.91 (2H, t, J=6.2 Hz), 6.77 (2H, d, J=8.6 Hz), 6.84 (1H, d, J=1.2 Hz), 6.93 (1H, d, J=1.2 Hz), 6.97 (2H, d, J=8.6 Hz).

IR (KBr): 3500–3100, 3119, 2934, 2861, 1615, 1593, 1516, 1495, 1454, 1373, 1252, 1173, 1152, 1123, 1053 cm$^{-1}$.

Reference Example 14

3-{3-[2-(2-hydroxyethyl)-1H-imidazol-1-yl]propyl}phenol

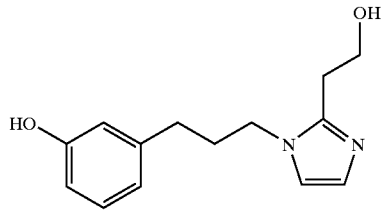

(i) 2-(1-{3-[3-(benzyloxy)phenyl]propyl}-1H-imidazol-2-yl)-1-ethanol

Using benzyl 3-(3-iodopropyl)phenyl ether (3.53 g), 2-(2-hydroxyethyl)imidazole (1.46 g) and 65% oily sodium hydride (0.48 g), the same reaction as Reference Example 11-(iv) was carried out to yield the titled compound (2.66 g) as a colorless oily substance.

$^1$H-NMR (CDCl$_3$) δ: 2.05 (2H, quintet, J=7.3 Hz), 2.61 (2H, t, J=7.5 Hz), 2.73 (2H, t, J=5.5 Hz), 3.81 (2H, t, J=7.3 Hz), 4.02 (2H, t, J=5.5 Hz), 5.06 (2H, s), 6.73–6.88 (3H, m), 6.82 (1H, d, J=1.2 Hz), 6.95 (1H, d, J=1.2 Hz), 7.23 (1H, t, J=8.2 Hz), 7.31–7.48 (5H, m).

IR (neat): 3500–3100, 3067, 3034, 2938, 2867, 1599, 1584, 1524, 1491, 1453, 1381, 1316, 1260, 1155, 1119, 1053, 1026 cm$^{-1}$.

(ii) 3-{3-[2-(2-hydroxyethyl)-1H-imidazol-1-yl]propyl}phenol

Using 2-(1-{3-[3-(benzyloxy)phenyl]propyl}-1H-imidazol-2-yl)-1-ethanol (2.42 g) and 10% palladium carbon (0.24 g), the same reaction as Reference Example 11-(v) was carried out to yield the titled compound (1.69 g) as colorless crystals.

mp 111–113° C.

¹H-NMR (CDCl₃) δ: 2.07 (2H, quintet, J=6.9 Hz), 2.55 (2H, t, J=7.3 Hz), 2.73 (2H, t, J=5.9 Hz), 3.80 (2H, t, J=7.1 Hz), 4.00 (2H, t, J=5.9. Hz), 6.55–6.76 (3H, m), 6.86 (1H, d, J=1.4 Hz), 6.96 (1H, d, J=1.4 Hz), 7.15 (1H, t, J=7.8 Hz).

IR (KBr) cm⁻¹: 3500–3100, 3046, 2940, 2865, 2712, 2604, 1599, 1588, 1528, 1483, 1456, 1372, 1279, 1250, 1155, 1123, 1057.

Reference Example 15
3-{1-[4-(4-hydroxyphenyl)butyl]-1H-imidazol-2-yl}-1,2-propanediol

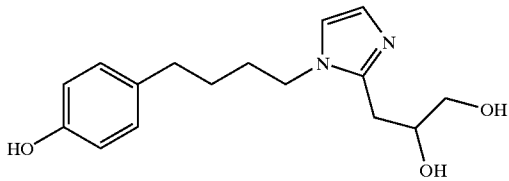

(i) 3-{1-[4-(4-benzyloxyphenyl)butyl]-1H-imidazol-2-yl}-1,2-propanediol

Using benzyl 4-(4-iodobutyl)phenyl ether (2.05 g), 2-(2,3-dihydroxypropyl)imidazole (1.0 g) and 65% oily sodium hydride (0.259 g), the same reaction as Reference Example 11-(iv) was carried out to yield the titled compound (1.23 g) as colorless crystals.

¹H-NMR (CDCl₃) δ: 1.52–1.83 (4H, m), 2.57 (2H, t, J=7.1 Hz), 2.78 (2H, d, J=5.2 Hz), 2.79 (1H, d, J=6.8 Hz), 3.62 (1H, dd, J=4.8 Hz, 11.2 Hz), 3.74 (1H, dd, J=4.8 Hz, 11.2 Hz), 3.82 (2H, t, J=7.1 Hz), 4.12–4.23 (1H, m), 5.04 (2H, s), 6.79 (1H, d, J=1.4 Hz), 6.90 (2H, d, J=8.6 Hz), 6.91 (1H, d, J=1.4 Hz), 7.05 (2H, d, J=8.6 Hz), 7.30–7.47 (5H, m).

IR (KBr): 3500–3200, 3065, 3030, 2932, 2861, 1611, 1582, 1510, 1495, 1454, 1379, 1296, 1275, 1240, 1177, 1150, 1123, 1080, 1026 cm⁻¹.

(ii) 3-{1-[4-(4-hydroxyphenyl)butyl]-1H-imidazol-2-yl}-1,2-propanediol

Using 3-{1-[4-(4-benzyloxyphenyl)butyl]-1H-imidazol-2-yl}-1,2-propanediol (1.22 g) and 10% palladium carbon (0.18 g), the same reaction as Reference Example 11-(v) was carried out to yield the titled compound (0.918 g) as colorless crystals.

¹H-NMR (CDCl₃+CD₃OD) δ: 1.50–1.80 (4H, m), 2.55 (2H, t, J=7.0 Hz), 2.75 (1H, d, J=7.2 Hz), 2.76 (1H, d, J=5.6 Hz), 3.49 (1H, dd, J=5.4 Hz, 11.6 Hz), 3.62 (1H, dd, J=4.2 Hz, 11.6 Hz), 3.84 (2H, t, J=7.0 Hz), 3.97–4.08 (1H, m), 6.75 (2H, d, J=8.6 Hz), 6.80 (1H, d, J=1.4 Hz), 6.89 (1H, d, J=1.4 Hz), 6.97 (2H, d, J=8.6 Hz).

IR (KBr): 3500–3100, 3011, 2936, 2859, 1613, 1595, 1516, 1489, 1456, 1372, 1360, 1252, 1171, 1150, 1125, 1101, 1030 cm⁻¹.

Reference Example 16

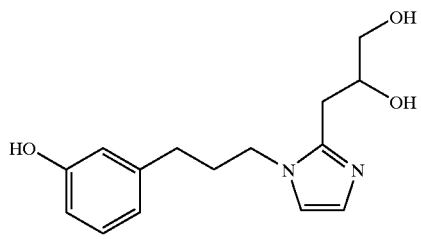

(i) 3-{1-[3-(3-benzyloxyphenyl)propyl]-1H-imidazol-2-yl}-1,2-propanediol

Using benzyl 3-(3-iodopropyl)phenyl ether (1.98 g), 2-(2,3-dihydroxypropyl)imidazole (1.0 g) and 65% oily sodium hydride (0.259 g), the same reaction as Reference Example 11-(iv) was carried out to yield the titled compound (1.31 g) as a colorless oily substance.

¹H-NMR (CDCl₃) δ: 2.05 (2H, quintet, J=7.3 Hz), 2.60 (2H, t, J=7.3 Hz), 2.73 (1H, d, J=4.8 Hz), 2.74 (1H, d, J=7.2 Hz), 3.61 (1H, dd, J=4.8 Hz, 11.2 Hz), 3.74 (1H, dd, J=4.8 Hz, 11.2 Hz), 3.82 (2H, t, J=7.3 Hz), 4.12–4.23 (1H, m), 5.06 (2H, s), 6.73–6.88 (3H, m), 6.81 (1H, d, J=1.2 Hz), 6.93 (1H, d, J=1.2 Hz), 7.23 (1H, t, J=8.4 Hz), 7.31–7.48 (5H, m).

IR (neat): 3500–3200, 3063, 3032, 2934, 2865, 1599, 1584, 1526, 1489, 1454, 1381, 1316, 1260, 1155, 1123, 1082, 1028 cm⁻¹.

(ii) 3-{1-[3-(3-hydroxyphenyl)propyl]-1H-imidazol-2-yl)-1,2-propanediol

Using 3-(1-[3-(3-benzyloxyphenyl)propyl]-1H-imidazol-2-yl}-1,2-propanediol (1.30 g) and 10% palladium carbon (0.195 g), the same reaction as Reference Example 11-(v) was carried out to yield the titled compound (0.979 g) as a colorless oily substance.

¹H-NMR (CDCl₃+CD₃OD) δ: 2.07 (2H, quintet, J=7.4 Hz), 2.58 (2H, t, J=7.3 Hz), 2.72 (1H, d, J=6.8 Hz), 2.72 (1H, d, J=5.8 Hz), 3.50 (1H, dd, J=5.4 Hz, 11.4 Hz), 3.61 (1H, d, J=4.2 Hz, 11.4 Hz), 3.85 (2H, t, J=7.3 Hz), 3.98–4.10 (1H, m), 6.60–6.74 (3H, m), 6.86 (1H, d, J=1.4 Hz), 6.92 (1H, d, J=1.4 Hz), 7.14 (1H, t, J=7.8 Hz).

IR (neat): 3500–3100, 3040, 2942, 2863, 1599, 1588, 1530, 1483, 1456, 1360, 1279, 1254, 1155, 1125, 1088, 1030 cm⁻¹.

Reference Example 17
2-[(E)-2-(2,4-difluorophenyl)ethenyl]-4-[[4-(4-iodobutyl)phenoxy]methyl]-1,3-oxazole

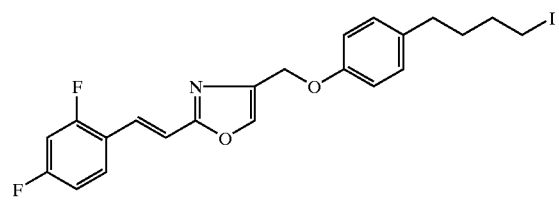

(i) 4-[4-[2-(E)-[2-(2,4-difluorophenyl)ethenyl]-1,3-oxazol-4-yl]methoxyphenyl]-1-butanol To a solution of 4-(4-hydroxyphenyl)-1-butanol (1.99 g) in DMF (20 ml), 60% oily sodium hydride (528 mg) was added under ice cooling, followed by stirring at room temperature for 30 minutes. Under ice cooling, (E)-4-chloromethyl-2-[2-(2,4-difluorophenyl)ethenyl]oxazole (3.37 g) was added, followed by stirring overnight at room temperature. After water and 1 N hydrochloric acid was added, the reaction mixture was extracted with ethyl acetate. After the extract was dried over magnesium sulfate, it was concentrated under reduced pressure; the residue was recrystallized from ethyl acetate-diethyl ether-hexane to yield the titled compound (3.71 g) as colorless crystals.

mp 75–76° C.

¹H-NMR (CDCl₃) δ: 1.5–1.7 (4H, m), 2.60 (2H, t, J=6.8 Hz), 3.66 (2H, t, J=6.0 Hz), 5.02 (2H, s), 6.8–6.9 (1H, m), 6.89 (2H, d, J=8.4 Hz), 6.98 (1H, d, J=17.0 Hz), 7.11 (2H, d, J=8.4 Hz), 7.5–7.6 (1H, m), 7.59 (1H, d, J=17.0 Hz), 7.66 (1H, s).

IR (KBr): 1613, 1514, 1493, 1431, 1279, 1246, 1140, 968, 856 cm⁻¹.

(ii) 2-[(E)-2-(2,4-difluorophenyl)ethenyl]-4-[[4-(4-iodobutyl)phenoxy]methyl]-1,3-oxazole To a solution of 4-[4-[2-(E)-[2-(2,4-difluorophenyl)ethenyl]-1,3-oxazol-4-yl]methoxyphenyl]-1-butanol (3.47 g) in THF (50 ml), triethylamine (1.37 ml) was added; under ice cooling, methanesulfonyl chloride (0.77 ml) was added, followed by stirring at room temperature for 30 minutes. After water was added, the reaction mixture was extracted with ethyl acetate; the extract was washed with saline, after which it was dried over magnesium sulfate. The solvent was distilled off; to the residue, acetone (100 ml) and sodium iodide (6.75 g) were added, followed by stirring at 40–50° C. for 2 hours. The reaction mixture was concentrated; water was added; the mixture was extracted with ethyl acetate. The extract was washed sequentially with aqueous sodium thiosulfate and saline and dried over magnesium sulfate, after which it was concentrated under reduced pressure. The precipitate was collected by filtration and washed with diethyl ether-hexane to yield the titled compound (3.55 g) as a pale-yellow powder.

$^1$H-NMR (CDCl$_3$) δ: 1.6–1.9 (4H, m), 2.5–2.7 (2H, m) 3.1–3.3 (2H, m), 5.02 (2H, s), 6.8–7.2 (6H, m), 7.5–7.75 (4H, m).

IR (KBr): 1615, 1514, 1493, 1431, 1279, 1246, 1140, 966, 856 cm$^{-1}$.

Reference Example 18
2-[(E)-2-(4-bromophenyl)ethenyl]-4-[[4-(4-iodobutyl)phenoxy]methyl]-1,3-oxazole

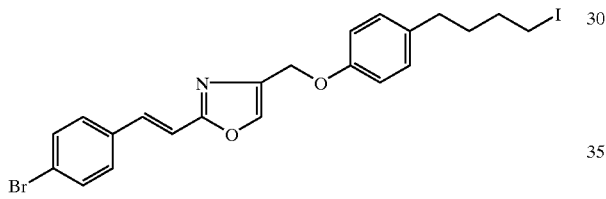

Using 4-(4-hydroxyphenyl)-1-butanol (4.99 g) and (E)-4-chloromethyl-2-[2-(4-bromophenyl)ethenyl]oxazole (7.43 g), the same reaction as Reference Example 17-(i) was carried out to yield 4-[4-[2-(E)-[2-(4-bromophenyl)ethenyl]-1,3-oxazol-4-yl]methoxyphenyl]-1-butanol (9.70 g). Using the compound obtained (4.28 g), the same reaction as Reference Example 17-(ii) was carried out to yield the titled compound (4.47 g) as a white powder.

$^1$H-NMR (CDCl$_3$) δ: 1.65–1.95 (4H, m), 2.58 (2H, t, J=7.2 Hz), 3.20 (2H, t, J=6.8 Hz), 5.02 (2H, s), 6.92 (1H, d, J=16.4 Hz), 6.92 (2H, d, J=8.6 Hz), 7.38 (2H, d, J=8.4 Hz), 7.47 (1H, d, J=16.4 Hz), 7.52 (2H, d, J=8.4 Hz), 7.66 (1H, s).

Example 1
[1-[4-[4-[[2-[(E)-2-(4-methylphenyl)ethenyl]-1,3-oxazol-4-yl]methoxy]phenyl]butyl]-1H-1,2,3-triazole

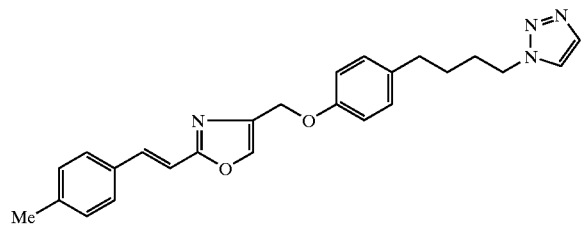

To a solution of 4-[4-(1H-1,2,3-triazol-1-yl)butyl]phenol (174 mg) in DMF (4 ml), 60% oily sodium hydride (35 mg) was added under ice cooling, followed by stirring at room temperature for 30 minutes. Under ice cooling, (E)-4-chloromethyl-2-[2-(4-methylphenyl)ethenyl]oxazole (206 mg) was added, followed by stirring at room temperature for 2 hours. After water was added to the reaction mixture, the precipitate was collected by filtration and washed with water. The precipitate was dissolved in a mixture of THF-ethyl acetate, and the solution was washed with water and saline, and dried over magnesium sulfate, after which it was concentrated under reduced pressure. The residue was recrystallized from ethyl acetate-hexane to yield the titled compound (281 mg) as colorless crystals.

mp 154–155° C.

$^1$H-NMR (CDCl$_3$) δ: 1.5–1.7 (2H, m), 1.85–2.05 (2H, m) 2.38 (3H, s), 2.60 (2H, t, J=7.5 Hz), 4.39 (2H, t, J=7.0 Hz), 5.01 (2H, s), 6.87 (2H, d, J=8.6 Hz), 6.9–7.0 (1H, m), 7.19 (2H, d, J=8.6 Hz), 7.19 (2H, d, J=8.0 Hz), 7.42 (2H, d, J=8.0 Hz), 7.5–7.7 (4H, m).

IR (KBr): 1640, 1607, 1530, 1514, 1464, 1339, 1256, 1211, 1053, 974, 810 cm$^{-1}$.

Anal. calcd for $C_{25}H_{26}N_4O_2$: C, 72.44; H, 6.32; N, 13.52. Found: C, 72.36; H, 6.49; N, 13.70.

Example 2
1-{4-[4-({2-[(E)-2-(4-fluorophenyl)ethenyl]-1,3-oxazol-4-yl}methoxy)phenyl]butyl}-1H-1,2,3-triazole

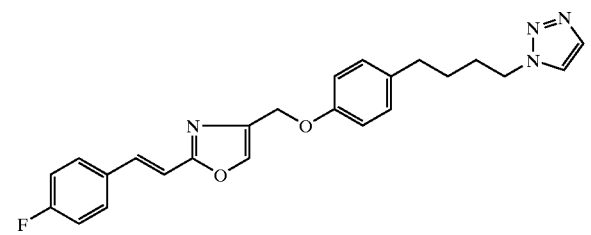

In an argon atmosphere, 4-[4-(1H-1,2,3-triazol-1-yl)butyl]phenol (218 mg) and 65% oily sodium hydride (39 mg) were dissolved in DMF (5 ml) added thereto. With stirring under ice cooling, 4-(chloromethyl)-2-[(E)-2-(4-fluorophenyl)ethenyl]-1,3-oxazole (250 mg) was added, followed by stirring at room temperature for 3 hours. After water was added, the reaction mixture was extracted with ethyl acetate. The extract was washed with water and saturated saline and dried over sodium sulfate, after which it was concentrated under reduced pressure. The residue was purified by silica gel column chromatography (eluent: chloroform-ethanol=24:1), after which it was recrystallized from ethyl acetate to yield the titled compound (368 mg) as colorless crystals.

mp 124–125° C.

$^1$H-NMR (CDCl$_3$) δ: 1.62 (2H, quintet, J=7.0 Hz), 1.94 (2H, quintet, J=7.5 Hz), 2.61 (2H, t, J=7.5 Hz), 4.40 (2H, t, J=7.0 Hz), 5.01 (2H, s), 6.86 (1H, d, J=16.0 Hz), 6.92 (2H, d, J=8.6 Hz), 7.08 (2H, d, J=8.6 Hz), 7.09 (2H, t, J=8.7 Hz), 7.46–7.57 (4H, m), 7.66 (1H, s), 7.70 (1H, d, J=1.0 Hz).

IR (KBr): 3420, 3160, 3120, 2940, 2924, 2865, 1644, 1599, 1584, 1532, 1512, 1466, 1435, 1400, 1337, 1302, 1248, 1229, 1211, 1177, 1161, 1113, 1076, 1049, 1030 cm$^{-1}$.

Anal calcd for $C_{24}H_{23}N_4O_2F$: C, 68.88; H, 5.55; N, 13.39. Found: C, 68.70; H, 5.55; N, 13.49.

Example 3

1-{3-[3-({2-[(E)-2-(4-fluorophenyl)ethenyl]-1,3-oxazol-4-yl}methoxy)phenyl]propyl}-1H-1,2,3-triazole

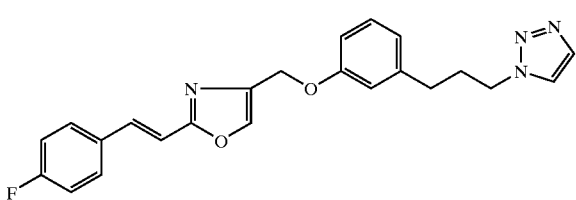

Using 3-[3-(1H-1,2,3-triazol-1-yl)propyl]phenol(208 mg), 65% oily sodium hydride (39 mg) and 4-(chloromethyl)-2-[(E)-2-(4-fluorophenyl)ethenyl]-1,3-oxazole (250 mg), the same reaction as Example 2 was carried out to yield the titled compound (366 mg).

mp 105–106° C.

$^1$H-NMR (CDCl$_3$) δ: 2.26 (2H, quintet, J=7.2 Hz), 2.64 (2H, t, J=7.5 Hz), 4.39 (2H, t, J=7.0 Hz), 5.03 (2H, s), 6.78–6.89 (3H, m), 6.86 (1H, d, J=16.2 Hz), 7.09 (2H, t, J=8.6 Hz), 7.25 (1H, t, J=7.8 Hz), 7.51 (1H, d, J=16.2 Hz), 7.47–7.54 (3H, m), 7.68 (1H, s), 7.72 (1H, s).

IR (KBr): 3110, 3050, 2955, 2870, 1642, 1601, 1586, 1532, 1507, 1489, 1460, 1453, 1337, 1310, 1273, 1240, 1213, 1177, 1159, 1113, 1097, 1080, 1065 cm$^{-1}$.

Anal calcd for C$_{23}$H$_{21}$N$_4$O$_2$F: C, 68.30; H, 5.23; N, 13.85. Found: C, 68.22; H, 5.04; N, 14.00.

Example 4

1-(4-{4-[(2-{(E)-2-[4-(trifluoromethyl)phenyl]ethenyl}-1,3-oxazol-4-yl)methoxy]phenyl}butyl)-1H-1,2,3-triazole

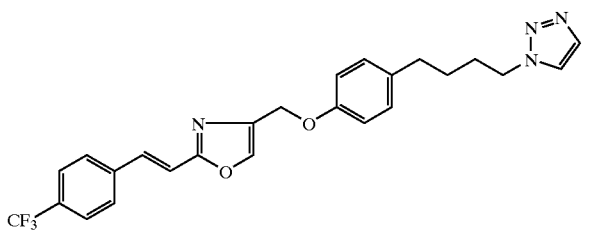

Using 4-[4-(1H-1,2,3-triazol-1-yl)butyl]phenol (152 mg), 65% oily sodium hydride (28 mg) and 4-(chloromethyl)-2-{(E)-2-[4-(trifluoromethyl)phenyl]ethenyl}-1,3-oxazole (212 mg), the same reaction as Example 2 was carried out to yield the titled compound (290 mg).

mp 160–161° C.

$^1$H-NMR (CDCl$_3$) δ: 1.62 (2H, quintet, J=7.0 Hz), 1.94 (2H, quintet, J=7.6 Hz), 2.61 (2H, t, J=7.4 Hz), 4.40 (2H, t, J=7.4 Hz), 5.02 (2H, s), 6.92 (2H, d, J=8.6 Hz), 7.02 (1H, d, J=16.6 Hz), 7.08 (2H, d, J=8.6 Hz), 7.50 (1H, s), 7.56 (1H, d, J=16.6 Hz), 7.64 (4H, s), 7.69 (1H, s), 7.71 (1H, s).

IR (KBr): 3120, 2936, 1615, 1584, 1512, 1464, 1414, 1327, 1248, 1159, 1125, 1069 cm$^{-1}$.

Anal calcd for C$_{25}$H$_{23}$N$_4$O$_2$F$_3$: C, 64.10; H, 4.95; N, 11.96. Found: C, 64.18; H, 5.12; N, 11.98.

Example 5

1-(3-{4-[(2-((E)-2-[4-(trifluoromethyl)phenyl]ethenyl)-1,3-oxazol-4-yl)methoxy]phenyl}propyl)-1H-1,2,3-triazole

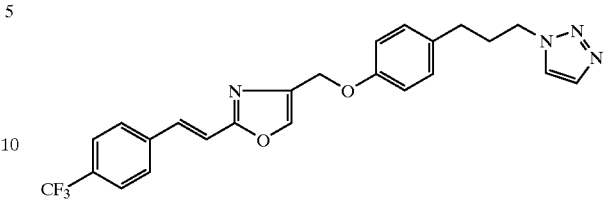

Using 4-[3-(1H-1,2,3-triazole1-yl)propyl]phenol (143 mg), 65% oily sodium hydride (28 mg) and 4-(chloromethyl)-2-{(E)-2-[4-(trifluoromethyl)phenyl]ethenyl}-1,3-oxazole (212 mg), the same reaction as Example 2 was carried out to yield the titled compound (232 mg).

mp 157–158° C.

$^1$H-NMR (CDCl$_3$) δ: 2.24 (2H, quintet, J=7.2 Hz), 2.61 (2H, t, J=7.3 Hz), 4.39 (2H, t, J=7.2 Hz), 5.03 (2H, s), 6.94 (2H, d, J=8.4 Hz), 7.02 (1H, d, J=16.4 Hz), 7.11 (2H, d, J=8.4 Hz), 7.52 (1H, s), 7.56 (1H, d, J=16.4 Hz), 7.64 (4H, s), 7.69 (1H, s), 7.72 (1H, s).

IR (KBr): 3129, 3100, 2934, 1613, 1584, 1547, 1510, 1449, 1416, 1337, 1329, 1291, 1238, 1179, 1140, 1109, 1071, 1009 cm$^{-1}$.

Anal calcd for C$_{24}$H$_{21}$N$_4$O$_2$F$_3$: C, 63.43; H, 4.66; N, 12.33. Found: C, 63.21; H, 4.73; N, 12.26.

Example 6

1-(3-{3-[(2-((E)-2-[4-(trifluoromethyl)phenyl]ethenyl}-1,3-oxazol-4-yl)methoxy]phenyl}propyl)-1H-1,2,3-triazole

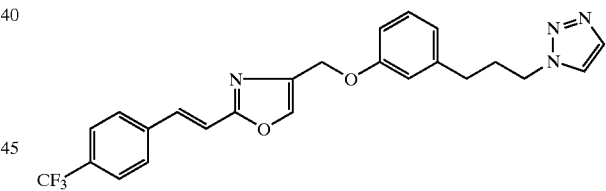

Using 3-[3-(1H-1,2,3-triazol-1-yl)propyl]phenol (123 mg), 65% oily sodium hydride (24 mg) and 4-(chloromethyl)-2-{(E)-2-[4-(trifluoromethyl)phenyl]ethenyl}-1,3-oxazole (183 mg), the same reaction as Example 2 was carried out to yield the titled compound (248 mg).

mp 115–116° C.

$^1$H-NMR (CDCl$_3$) δ: 2.26 (2H, quintet, J=7.2 Hz), 2.64 (2H, t, J=7.2 Hz), 4.39 (2H, t, J=7.2 Hz), 5.04 (2H, s), 6.77–6.91 (3H, m), 7.01 (1H, d, J=16.6 Hz), 7.25 (1H, t, J=8.4 Hz), 7.52 (1H, s), 7.56 (1H, d, J=16.6 Hz), 7.64 (4H, s), 7.71 (2H, s).

IR (KBr): 3140, 3050, 2940, 2860, 1610, 1599, 1586, 1487, 1451, 1415, 1327, 1262, 1169, 1125, 1113, 1069, 1017 cm$^{-1}$.

Anal calcd for C$_{24}$H$_{21}$N$_4$O$_2$F$_3$: C, 63.43; H, 4.66; N, 12.33. Found: C, 63.36; H, 4.73; N, 12.26.

Example 7

1-{4-[4-({2-[(E)-2-(2,4-difluorophenyl)ethenyl]-1,3-oxazol-4-yl}methoxy)phenyl]butyl}-1H-1,2,3-triazole

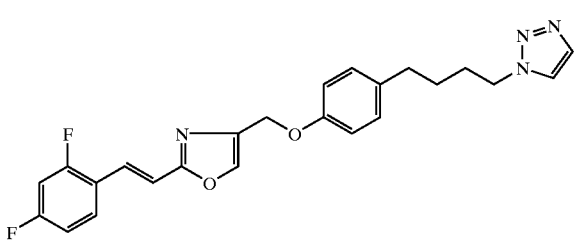

Using 4-[4-(1H-1,2,3-triazol-1-yl)butyl]phenol (152 mg), 65% oily sodium hydride (28 mg) and 4-(chloromethyl)-2-[(E)-2-(2,4-difluorophenyl)ethenyl]-1,3-oxazole (188 mg), the same reaction as Example 2 was carried out to yield the titled compound (254 mg).

mp 115–117° C.

$^1$H-NMR (CDCl$_3$) δ: 1.62 (2H, quintet, J=7.2 Hz), 1.94 (2H, quintet, J=7.5 Hz), 2.60 (2H, t, J=7.5 Hz), 4.39 (2H, t, J=7.1 Hz), 5.01 (2H, s), 6.81–6.98 (2H, m), 6.91 (2H, d, J=8.6 Hz), 6.98 (1H, d, J=16.2 Hz), 7.07 (2H, d, J=8.6 Hz), 7.47–7.53 (1H, m), 7.50 (1H, s), 7.59 (1H, d, J=16.2 Hz), 7.67 (1H, s), 7.70 (1H, IR (KBr): 3133, 2932, 2863, 1644, 1615, 1590, 1532, 1514, 1493, 1468, 1431, 1345, 1298, 1279, 1246, 1215, 1179, 1140, 1086, 1049, 1032 cm$^{-1}$.

Anal calcd for $C_{24}H_{22}N_4O_2F_2$: C, 66.05; H, 5.08; N, 12.84. Found: C, 66.03; H, 5.00; N, 13.03.

Example 8

1-{3-[3-({2-[(E)-2-(2,4-difluorophenyl)ethenyl]-1,3-oxazol-4-yl}methoxy)phenyl]propyl}-1H-1,2,3-triazole

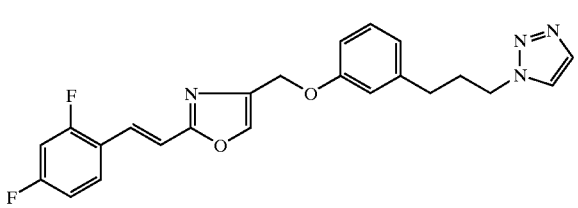

Using 3-[3-(1H-1,2,3-triazol-1-yl)propyl]phenol (143 mg), 65% oily sodium hydride (28 mg) and 4-(chloromethyl)-2-[(E)-2-(2,4-difluorophenyl)ethenyl]-1,3-oxazole (188 mg), the same reaction as Example 2 was carried out to yield the titled compound (257 mg).

mp 89–90° C.

$^1$H-NMR (CDCl$_3$) δ: 2.26 (2H, quintet, J=7.3 Hz), 2.64 (2H, t, J=7.4 Hz), 4.39 (2H, t, J=7.1 Hz), 5.03 (2H, s), 6.77–6.98 (5H, m), 6.98 (1H, d, J=16.8 Hz), 7.24 (1H, t, J=7.6 Hz), 7.47–7.60 (1H, m), 7.52 (1H, s), 7.59 (1H, d, J=16.8 Hz), 7.68 (1H, s), 7.71 (1H, s).

IR (KBr): 3127, 3071, 2934, 2868, 1644, 1615, 1599, 1534, 1495, 1453, 1433, 1354, 1273, 1215, 1159, 1142, 1090, 1028 cm$^{-1}$.

Anal calcd for $C_{23}H_{20}N_4O_2F_2$: C, 65.39; H, 4.77; N, 13.26. Found: C, 65.32; H, 4.56; N, 13.34.

Example 9

[1-[4-[4-[[2-[(E)-2-(2,6-difluorophenyl)ethenyl]-1,3-oxazol-4-yl]methoxy]phenyl]butyl]-1H-1,2,3-triazole

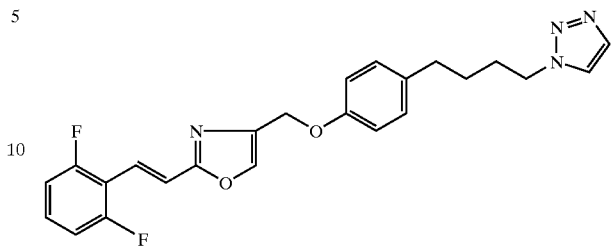

To a solution of 4-[4-(1H-1,2,3-triazol-1-yl)butyl]phenol (217 mg) in DMF (4 ml), 65% oily sodium hydride (41 mg) was added under ice cooling. After stirring at room temperature for 30 minutes, 4-(chloromethyl)-2-[(E)-2-(2,6-difluorophenyl) ethenyl]-1,3-oxazole (281 mg) was added under ice cooling, followed by overnight stirring at room temperature. Water was added under ice cooling; the precipitate was collected by filtration and washed with water, after which it was dissolved in THF-ethyl acetate. The reaction mixture was washed with water and saline and dried over magnesium sulfate, after which it was concentrated under reduced pressure. The residue was recrystallized from ethyl acetate-hexane to yield the titled compound (348 mg) as colorless crystals.

$^1$H-NMR (CDCl$_3$) δ: 1.5–1.7 (2H, m), 1.85–2.05 (2H, m) 2.60 (2H, t, J=7.4 Hz), 4.39 (2H, t, J=7.2 Hz), 5.02 (2H, s), 6.92 (2H, d, J=8.8 Hz), 6.94 (1H, d, J=17.4 Hz), 6.85–7.35 (3H, m), 7.07 (2H, d, J=8.8 Hz), 7.61 (1H, d, J=17.4 Hz), 7.45–7.7 (3H, m).

IR (KBr): 1620, 1586, 1514, 1464, 1244, 1024, 999, 968, 783 cm$^{-1}$.

Anal. calcd for $C_{24}H_{22}F_2N_4O_2$: C, 66.05; H, 5.08; N, 12.84. Found: C, 65.83; H, 5.06; N, 12.93.

Example 10

2-[1-[4-[4-[[2-[(E)-2-(4-methylphenyl)ethenyl]-1,3-oxazol-4-yl]methoxy]phenyl]butyl]-1H-imidazol-2-yl]-1-ethanol

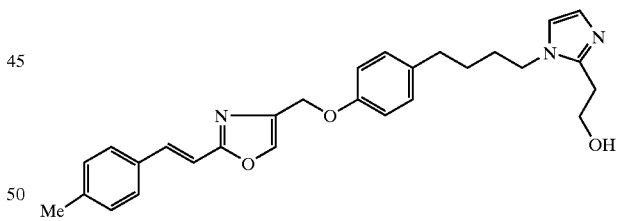

Using 4-[4-[2-(2-hydroxyethyl)-1H-imidazol-1-yl]butyl]phenol (260 mg) and (E)-4-chloromethyl-2-[2-(4-methylphenyl)ethenyl]oxazole(257 mg), the same reaction as Example 1 was carried out to yield the titled compound (331 mg) as colorless crystals.

mp 108–109° C.

$^1$H-NMR (CDCl$_3$) δ: 1.5–1.8 (4H, m), 2.38 (3H, s), 2.58 (2H, t, J=7.0 Hz), 2.79 (2H, t, J=5.6 Hz), 3.82 (2H, t, J=6.8 Hz), 4.03 (2H, t, J=5.6 Hz), 5.01 (2H, s), 6.8–6.85 (2H, m), 6.89 (1H, d, J=16.6 Hz), 6.92 (2H, d, J=8.6 Hz), 7.07 (2H, d, J=8.6 Hz), 7.19 (2H, d, J=7.8 Hz), 7.43 (2H, d, J=7.8 Hz), 7.51 (1H, d, J=16.6 Hz), 7.64 (1H, s).

IR (KBr): 1510, 1240, 1055, 806 cm$^{-1}$.

Anal. calcd for $C_{28}H_{31}N_3O_3$: C, 73.50; H, 6.83; N, 9.18. Found: C, 73.36; H, 6.66; N, 9.12.

Example 11

2-[1-[4-[4-[[2-[(E)-2-(3-methylphenyl)ethenyl]-1,3-oxazol-4-yl]methoxy]phenyl]butyl]-1H-imidazol-2-yl]-1-ethanol

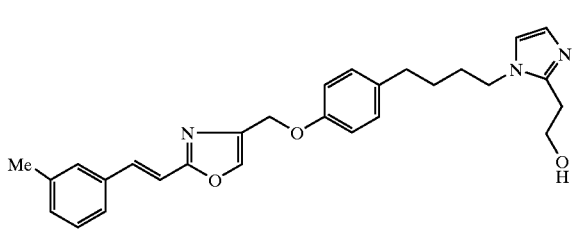

Using 4-[4-[2-(2-hydroxyethyl)-1H-imidazol-1-yl]butyl]phenol (260 mg) and (E)-4-chloromethyl-2-[2-(3-methylphenyl)ethenyl]oxazole (257 mg), the same reaction as Example 1 was carried out to yield the titled compound (290 mg) as colorless crystals.

mp 109–111° C.

$^1$H-NMR (CDCl$_3$) δ: 1.55–1.8 (4H, m), 2.38 (3H, s), 2.58 (2H, t, J=7.0 Hz), 2.78 (2H, t, J=5.6 Hz), 3.82 (2H, t, J=7.0 Hz), 4.03 (2H, t, J=5.6 Hz), 5.01 (2H, s), 6.80 (1H, d, J=1.4 Hz), 6.92 (1H, d, J=16.6 Hz), 6.92 (2H, d, J=8.8 Hz), 6.93 (1H, d, J=1.4 Hz), 7.07 (2H, d, J=8.8 Hz), 7.1–7.2 (1H, m), 7.2–7.4 (3H, m), 7.51 (1H, d, J=16.6 Hz), 7.65 (1H, s).

IR (KBr): 1514, 1460, 1250, 1051, 976, 828, 789 cm$^{-1}$.

Anal. calcd for C$_{28}$H$_{31}$N$_3$O$_3$.0.2H$_2$O: C, 72.92; H, 6.86; N, 9.11.

Found: C, 72.71; H, 6.74; N, 8.97.

Example 12

2-[1-[4-[4-[[2-[(E)-2-(2-methylphenyl)ethenyl]-1,3-oxazol-4-yl]methoxy]phenyl]butyl]-1H-imidazol-2-yl]-1-ethanol

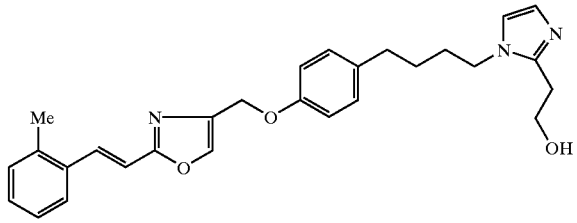

Using 4-[4-[2-(2-hydroxyethyl)-1H-imidazol-1-yl]butyl]phenol (153 mg) and (E)-4-chloromethyl-2-[2-(2-methylphenyl)ethenyl]oxazole (151 mg), the same reaction as Example 1 was carried out to yield the titled compound (167 mg) as colorless crystals.

mp 91–93° C. (ethyl acetate-hexane).

$^1$H-NMR(CDCl$_3$) δ: 1.5–1.8 (4H, m), 2.46 (3H, s), 2.59 (2H, t, J=7.0 Hz), 2.79 (2H, t, J=5.6 Hz), 3.82 (2H, t, J=7.0 Hz), 4.03 (2H, t, J=5.6 Hz), 5.02 (2H, s), 6.8–6.9 (3H, m), 6.92 (2H, d, J=8.6 Hz), 7.07 (2H, d, J=8.6 Hz), 7.2–7.3 (3H, m), 7.55–7.65 (1H, m), 7.66 (1H, s), 7.79 (1H, d, J=16.2 Hz).

IR (KBr): 1508, 1464, 1231, 1061, 1009, 862, 752 cm$^{-1}$.

Anal. calcd for C$_{28}$H$_{31}$N$_3$O$_3$.0.2H$_2$O: C, 72.92; H, 6.86; N, 9.11. Found: C, 72.98; H, 6.70; N, 9.23.

Example 13

2-[1-[4-[4-[[2-[(E)-2-(4-ethylphenyl)ethenyl]-1,3-oxazol-4-yl]methoxy]phenyl]butyl]-1H-imidazol-2-yl]-1-ethanol

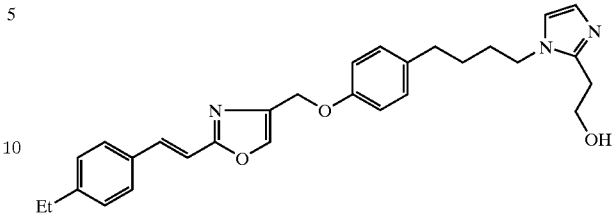

To a solution of 4-[4-[2-(2-hydroxyethyl)-1H-imidazol-1-yl]butyl]phenol (260 mg) in DMF (4 ml), 60% oily sodium hydride (44 mg) was added under ice cooling. After stirring at room temperature for 30 minutes, (E)-4-chloromethyl-2-[2-(4-ethylphenyl)ethenyl]oxazole (272 mg) was added under ice cooling. After stirring overnight at room temperature, water was added under ice cooling. The precipitate was collected by filtration and washed with water. The precipitate was dissolved in ethyl acetate and dried (magnesium sulfate), after which it was concentrated under reduced pressure. The residue was recrystallized from ethyl acetate-hexane to yield the titled compound (297 mg) as colorless crystals.

mp 94–95° C.

$^1$H-NMR (CDCl$_3$) δ: 1.25 (3H, t, J=7.4 Hz), 1.5–1.85 (4H, m), 2.59 (2H, t, J=7.0 Hz), 2.67 (2H, q, J=7.4 Hz), 2.79 (2H, t, J=5.4 Hz), 3.82 (2H, t, J=7.0 Hz), 4.04 (2H, t, J=5.4), 5.01 (2H, s), 6.8–7.0 (3H, m), 6.92 (2H, d, J=8.4 Hz), 7.07 (2H, d, J=8.4 Hz), 7.2–7.3 (2H, m), 7.4–7.5 (2H, m), 7.53 (1H, d, J=17.2 Hz), 7.65 (1H, s).

IR (KBr): 1508, 1462, 1231, 1181, 1061, 1007, 864, 833 cm$^{-1}$.

Anal. calcd for C$_{29}$H$_{33}$N$_3$O$_3$: C, 73.86; H, 7.05; N, 8.91. Found: C, 73.73; H, 6.79; N, 8.76.

Example 14

2-(1-(4-[4-({2-[(E)-2-(4-fluorophenyl)ethenyl]-1,3-oxazol-4-yl}methoxy)phenyl]butyl)-1H-imidazol-2-yl)-1-ethanol

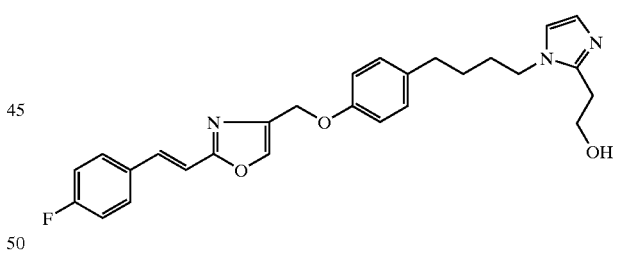

Using 4-[4-[2-(2-hydroxyethyl)-1H-imidazol-1-yl]butyl]phenol (391 mg), 65% oily sodium hydride (60 mg) and 4-(chloromethyl)-2-((E)-2-(4-fluorophenyl)ethenyl]-1,3-oxazole (375 mg), the same reaction as Example 2 was carried out to yield the titled compound (583 mg).

mp 130–132° C.

$^1$H-NMR (CDCl$_3$) δ: 1.56–1.84 (4H, m), 2.10–2.90 (1H, br), 2.58 (2H, t, J=7.1 Hz), 2.78 (2H, t, J=5.5 Hz), 3.82 (2H, t, J=7.1 Hz), 4.03 (2H, t, J=5.5 Hz), 5.01 (2H, s), 6.80–6.94 (5H, m), 7.04–7.13 (4H, m), 7.46–7.55 (3H, m), 7.65 (1H, s).

IR (KBr): 3150, 3113, 3048, 2936, 2861, 1642, 1599, 1582, 1532, 1512, 1464, 1422, 1399, 1375, 1337, 1302, 1277, 1246, 1229, 1209, 1177, 1159, 1148, 1105, 1051, 1001 cm$^{-1}$.

Anal calcd for C$_{27}$H$_{28}$N$_3$O$_3$F: C, 70.26; H, 6.11; N, 9.10. Found: C, 70.15; H, 6.06; N, 9.35.

Example 15
2-[1-[4-[4-[[2-[(E)-2-(4-chlorophenyl)ethenyl]-1,3-oxazol-4-yl]methoxy]phenyl]butyl]-1H-imidazol-2-yl]-1-ethanol

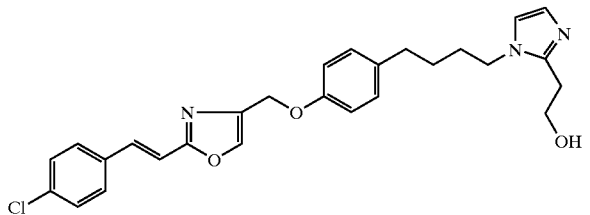

To a solution of 4-[4-[2-(2-hydroxyethyl)-1H-imidazol-1-yl]butyl]phenol (130 mg) in DMF (4 ml), 60% oily sodium hydride (22 mg) was added under ice cooling. After stirring at room temperature for 30 minutes, (E)-4-chloromethyl-2-[2-(4-chlorophenyl)ethenyl]oxazole (140 mg) was added under ice cooling. After stirring at 0° C. for 1 hour, then at room temperature overnight, water was added under ice cooling. The precipitate was collected by filtration, washed with water, and dissolved in a mixture of THF-ethyl acetate. This solution was dried over magnesium sulfate, after which it was concentrated under reduced pressure. The residue was recrystallized from methanol-ethyl acetate-diethyl ether to yield the titled compound (168 mg) as colorless crystals.

mp 127–128° C.

$^1$H-NMR (CDCl$_3$) δ: 1.5–1.8 (4H, m), 2.58 (2H, t, J=7.0 Hz), 2.78 (2H, t, J=5.4 Hz), 3.82 (2H, t, J=7.0 Hz), 4.03 (2H, t, J=5.4 Hz), 5.01 (2H, s), 6.8–7.0 (5H, m), 7.07 (2H, d, J=8.8 Hz), 7.35 (2H, d, J=8.4 Hz), 7.46 (2H, d, J=8.4 Hz), 7.4–7.55 (1H, m), 7.66 (1H, s).

IR (KBr): 1514, 1474, 1341, 1264, 1246, 1076, 966, 814 cm$^{-1}$.

Anal. calcd for C$_{27}$H$_{28}$ClN$_3$O$_3$: C, 67.85; H, 5.90; N, 8.79. Found: C, 67.85; H, 5.72; N, 9.09.

Example 16
2-[1-[4-[4-[[2-[(E)-2-(4-bromophenyl)ethenyl]-1,3-oxazol-4-yl]methoxy]phenyl]butyl]-1H-imidazol-2-yl]-1-ethanol

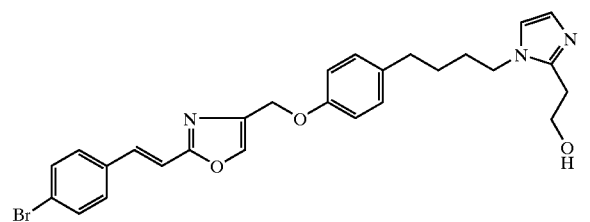

To a solution of 2-(1H-imidazol-2-yl)-ethanol (449 mg) in DMF (10 ml), 60% oily sodium hydride (176 mg) was added under ice cooling. After stirring at room temperature for 30 minutes, 4-[[4-(4-iodobutyl)phenoxy)methyl]-2-[(E)-2-(4-bromophenyl)ethenyl]-1,3-oxazole (2.15 g) was added under ice cooling. After stirring overnight at room temperature, water was added under ice cooling. The reaction mixture was extracted with a mixture of ethyl acetate-THF. The extract was dried over magnesium sulfate, after which it was concentrated under reduced pressure. The residue was recrystallized from ethyl acetate-hexane to yield the titled compound (2.09 g) as a light-yellow crystal.

mp 149–150° C.

$^1$H-NMR (CDCl$_3$) δ: 1.55–1.8 (4H, m), 2.58 (2H, t, J=7.0 Hz), 2.78 (2H, t, J=5.6 Hz), 3.82 (2H, t, J=7.0 Hz), 4.03 (2H, t, J=5.6 Hz), 5.01 (2H, s), 6.91 (2H, d, J=8.8 Hz), 6.92 (1H, d, J=16.3 Hz), 6.8–7.0 (2H, m), 7.07 (2H, d, J=8.8 Hz), 7.38 (2H, d, J=8.6 Hz), 7.47 (1H, d, J=16.3 Hz), 7.52 (2H, d, J=8.6 Hz), 7.66 (1H, s).

IR (KBr): 1514, 1487, 1254, 1055, 972, 826, 814 cm$^1$.

Anal. calcd for C$_{27}$H$_{28}$BrN$_3$O$_3$: C, 62.07; H, 5.40; N, 8.04. Found: C, 61.82; H, 5.26; N, 7.90.

Example 17
2-[1-[4-[4-[2-[(E)-2-(4-trifluoromethylphenyl)ethenyl]oxazol-4-yl]methoxyphenyl]butyl-1H-imidazol-2-yl]-1-ethanol

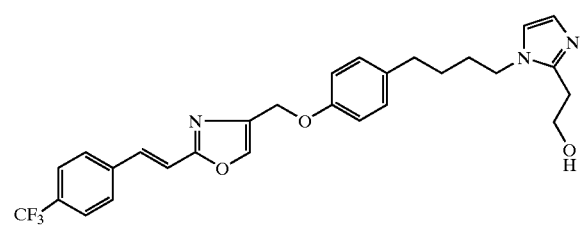

In an argon atmosphere, DMF (4 ml) was added to a mixture of 65% sodium hydride (40.6 mg) and 4-[4-[2-(2-hydroxyethyl)-1H-imidazol-1-yl]butyl]phenol (260 mg) at 0° C. After stirring at room temperature for 30 minutes, [2-[(E)-2-(4-trifluoromethylphenyl)ethenyl]oxazol-4-yl]methyl chloride (316 mg) was added at 0° C., followed by stirring at room temperature for 15 hours, After water was added to the reaction mixture, the precipitated crystal was collected by filtration, washed with water and isopropyl ether, after which it was recrystallized from acetone-hexane to yield the titled compound (393 mg) as pale-yellow needles.

$^1$H-NMR (CDCl$_3$) δ: 1.56–1.74 (4H, m), 2.59 (2H, t, J=6.6 Hz), 2.78 (2H, t, J=5.4 Hz), 3.82 (2H, t, J=6.8 Hz), 4.03 (2H, t, J=5.4 Hz), 5.02 (2H, d, J=1.2 Hz), 6.81 (1H, d, J=1.6 Hz), 6.90–6.95 (4H, m), 7.02 (2H, d, J=16.2 Hz), 7.52–7.69 (6H, m).

IR (KBr): 1512, 1323, 1244. 1175, 1132, 1113, 1067, 1055 cm$^{-1}$.

Example 18
2-[1-[3-[4-[2-[(E)-2-(4-trifluoromethylphenyl)ethenyl]oxazol-4-yl]methoxyphenyl]propyl]-1H-imidazol-2-yl]-1-ethanol

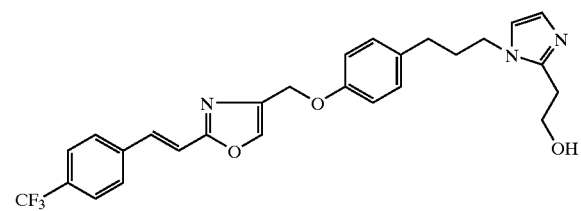

Using 65% sodium hydride (40.6 mg), 4-[3-[2-(hydroxyethyl)-1H-imidazol-1-yl]propyl]phenol (246 mg) and [2-[(E)-2-(4-trifluoromethylphenyl)ethenyl]oxazol-4-yl]methyl chloride (316 mg), the same reaction as Example 17 was carried out to yield the titled compound (330 mg) as colorless needles.

$^1$H-NMR (CDCl$_3$) δ: 2.01–2.08 (2H, m), 2.60 (2H, t, J=7.8 Hz), 2.74 (2H, t, J=5.8 Hz), 3.83 (2H, t, J=7.4 Hz), 4.03 (2H, t, J=5.8 Hz), 5.03 (2H, s), 6.84 (1H, d, J=1.2 Hz), 6.96–7.12 (6H, m), 7.52–7.70 (6H, m).

IR (KBr): 1512, 1327, 1246, 1173, 1125, 1069, 1017, 826 cm$^{-1}$.

Example 19
2-[1-[4-[4-[[2-[(E)-2-(2,4-difluorophenyl)ethenyl]-1,3-oxazol-4-yl]methoxy]phenyl]butyl]-1H-imidazol-2-yl]-1-ethanol

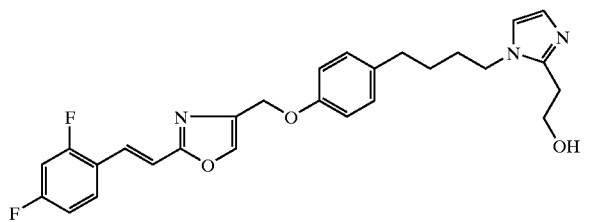

To a solution of 4-[4-[2-(2-hydroxyethyl)-1H-imidazol-1-yl ]butyl]phenol (260 mg) in DMF (4 ml), 60% oily sodium hydride (44 mg) was added under ice cooling. After stirring at room temperature for 30 minutes, (E)-4-chloromethyl-2-[2-(2,4-difluorophenyl) ethenyl]oxazole (281 mg) was added under ice cooling. After stirring at room temperature for 3 days, water was added under ice cooling. The precipitate was collected by filtration and washed with water. The precipitate was dissolved in a mixture of ethyl acetate-THF and dried over magnesium sulfate, after which it was concentrated under reduced pressure. The residue was recrystallized from ethyl acetate-hexane to yield the titled compound (275 mg) as pale-yellow crystals.

mp 93–95° C.

$^1$H-NMR (CDCl$_3$) δ: 1.55–1.85 (4H, m), 2.58 (2H, t, J=7.0 Hz), 2.78 (2H, t, J=5.4 Hz), 3.82 (2H, t, J=7.0 Hz), 4.03 (2H, t, J=5.4 Hz), 5.01 (2H, s), 6.8–7.0 (6H, m), 6.98 (1H, d, J=16.3 Hz), 7.07 (2H, d, J=8.8 Hz), 7.5–7.6 (1H, m), 7.59 (1H, d, J=16.3 Hz), 7.67 (1H, s).

IR (KBr): 1611, 1508, 1277, 1231, 1140, 1103, 1063, 970, 860 cm$^{-1}$.

Anal. calcd for C$_{27}$H$_{27}$F$_2$N$_3$O$_3$·0.1H$_2$O: C, 67.38; H, 5.70; N, 8.73. Found: C, 67.24; H, 5.74; N, 8.55.

Example 20
2-[1-[3-[4-[[2-[(E)-2-(2,4-difluorophenyl)ethenyl]-1,3-oxazol-4-yl]methoxy]phenyl]propyl]-1H-imidazol-2-yl]-1-ethanol

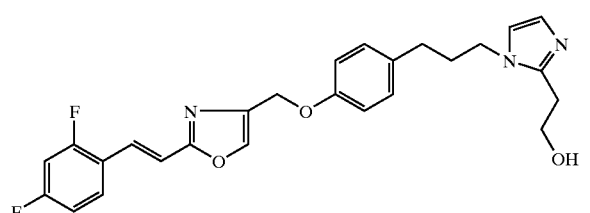

To a solution of 4-[4-[2-(2-hydroxyethyl)-1H-imidazol-1-yl ]propyl]phenol(246 mg) in DMF (4 ml), 60% oily sodium hydride (44 mg) was added under ice cooling. After stirring at room temperature for 30 minutes, (E)-4-chloromethyl-2-[2-(2,4-difluorophenyl) ethenyl]oxazole (281 mg) was added under ice cooling. After stirring overnight at room temperature, water was added under ice cooling. The precipitate was collected by filtration and washed with water. The precipitate was dissolved in ethyl acetate and dried over magnesium sulfate, after which it was concentrated under reduced pressure. The residue was recrystallized from ethyl acetate-diethyl ether-hexane to yield the titled compound (272 mg) as colorless crystals.

mp 94–96° C.

$^1$H-NMR (CDCl$_3$) δ: 1.95–2.15 (2H, m), 2.5–2.65 (2H, m), 2.65–2.8 (2H, m), 3.75–3.9 (2H, m), 3.95–4.1 (2H, m), 5.02 (2H, s), 6.8–7.15 (9H, m), 7.45–7.7 (3H, m).

IR(KBr): 1609, 1512, 1277, 1231, 1140, 1061, 1020, 974, 860 cm$^{-1}$.

Anal. calcd for C$_{26}$H$_{25}$F$_2$N$_3$O$_3$·0.4H$_2$O: C, 66.06; H, 5.50; N, 8.89. Found: C, 66.13; H, 5.38; N, 8.55.

Example 21
2-[1-[3-[4-[[2-[(E)-2-(2,6-difluorophenyl)ethenyl]-1,3-oxazol-4-yl]methoxy]phenyl]propyl]-1H-imidazol-2-yl]-1-ethanol

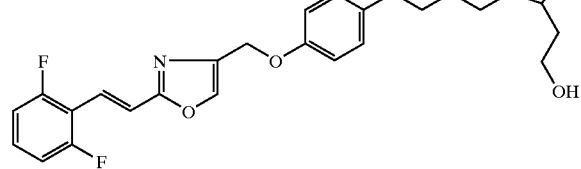

Using 2-(2-hydroxyethyl)-1-[4-(4-hydroxyphenyl)butyl]imidazole (260 mg), 60% oily sodium hydride (41 mg) and (E)-4-chloromethyl-2-[2-(2,6-difluorophenyl)ethenyl]oxazole (281 mg), the same reaction as Example 19 was carried out to yield the titled compound (359 mg) as colorless crystals.

mp 106–107° C.

$^1$H-NMR (CDCl$_3$) δ: 1.5–1.8 (4H, m), 2.58 (2H, t, J=7.0 Hz), 2.78 (2H, t, J=5.6 Hz), 3.82 (2H, t, J=7.0 Hz), 4.03 (2H, t, J=5.6 Hz), 5.02 (2H, s), 6.8–7.0 (6H, m), 7.07 (2H, d, J=8.4 Hz), 7.2–7.35 (2H, m), 7.61 (1H, d, J=16.8 Hz), 7.68 (1H, s).

IR (KBr): 1618, 1516, 1472, 1456, 1246, 1065, 1001, 974, 789 cm$^{-1}$.

Anal. calcd for C$_{27}$H$_{27}$F$_2$N$_3$O$_3$: C, 67.63; H, 5.68; N, 8.76. Found: C, 67.78; H, 5.57; N, 9.01.

Example 22
3-(1-{4-[4-({2-[(E)-2-(3-methylphenyl)ethenyl]-1,3-oxazol-4-yl}methoxy)phenyl]butyl}-1H-imidazol-2-yl)-1,2-propanediol

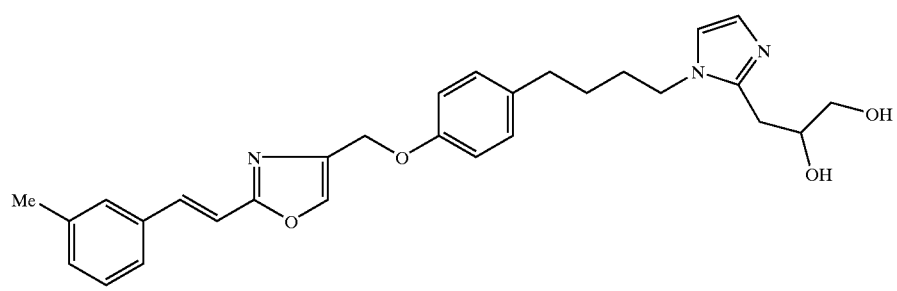

Using 3-{1-[4-(4-hydroxyphenyl)butyl]-1H-imidazol-2-yl}-1,2-propanediol (154 mg), 65% oily sodium hydride (21 mg) and 4-(chloromethyl)-2-[(E)-2-(3-methylphenyl)

ethenyl]-1,3-oxazole (131 mg), the same reaction as Example 2 was carried out to yield the titled compound (156 mg).

mp 102–104° C.

¹H-NMR (CDCl₃) δ: 1.52–1.82 (4H, m), 2.39 (3H, s), 2.59 (2H, t, J=7.0 Hz), 2.77 (1H, d, J=5.0 Hz), 2.78 (1H, d, J=6.8 Hz), 3.64 (1H, dd, J=4.8 Hz, 11.2 Hz), 3.76 (1H, dd, J=4.2 Hz, 11.2 Hz), 3.82 (2H, t, J=7.0 Hz), 4.12–4.24 (1H, m), 5.02 (2H, s), 6.80 (1H, d, J=1.4 Hz), 6.92 (1H, d, J=1.4 Hz), 6.93 (1H, d, J=16.2 Hz), 6.93 (1H, d, J=8.8 Hz), 7.08 (2H, d, J=8.8 Hz), 7.13–7.39 (4H, m), 7.52 (1H, d, J=16.2 Hz), 7.66 (1H, s).

IR (KBr): 3500–3200, 3112, 3029, 2934, 2865, 1645, 1609, 1584, 1510, 1491, 1462, 1379, 1350, 1242, 1177, 1150, 1123, 1100, 1026 cm⁻¹.

Anal calcd for $C_{29}H_{33}N_3O_4 \cdot 0.5H_2O$: C, 70.14; H, 6.90; N, 8.46. Found: C, 70.39; H, 6.63; N, 8.51.

Example 23

3-(1-{4-[4-({2-[(E)-2-(4-fluorophenyl)ethenyl]-1,3-oxazol-4-yl}methoxy)phenyl]butyl}-1H-imidazol-2-yl)-1,2-propanediol

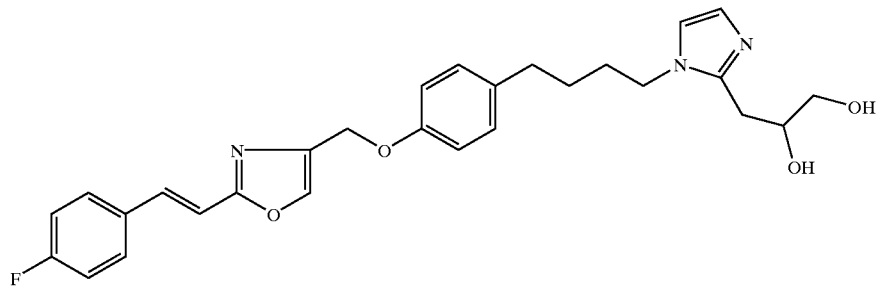

Using 3-{1-[4-(4-hydroxyphenyl)butyl]-1H-imidazol-2-yl}-1,2-propanediol (291 mg), 65% oily sodium hydride (39 mg) and 4-(chloromethyl)-2-[(E)-2-(4-fluorophenyl)ethenyl]-1,3-oxazole (250 mg), the same reaction as Example 2 was carried out to yield the titled compound (347 mg).

mp 114–116° C.

¹H-NMR (CDCl₃) δ: 1.52–1.83 (4H, m), 2.59 (2H, t, J=7.2 Hz), 2.76 (1H, d, J=5.2 Hz), 2.77 (1H, d, J=7.0 Hz), 3.64 (1H, dd, J=4.8 Hz, 11.4 Hz), 3.76 (1H, dd, J=4.2 Hz, 11.4 Hz), 3.82 (2H, t, J=6.8 Hz), 4.12–4.24 (1H, m), 5.01 (2H, s), 6.80 (1H, d, J=1.4 Hz), 6.86 (1H, d, J=16.8 Hz), 6.92 (1H, d, J=1.4 Hz), 6.93 (2H, d, J=8.8 Hz), 7.07 (2H, d, J=8.8 Hz), 7.09 (2H, d, J=8.7 Hz), 7.46–7.56 (3H, m), 7.66 (1H,

IR (KBr): 3500–3200, 3152, 3104, 3044, 2940, 2865, 1644, 1599, 1584, 1532, 1512, 1495, 1462, 1422, 1400, 1339, 1300, 1246, 1177, 1159, 1098, 1047 cm⁻¹.

Anal calcd for $C_{28}H_{30}N_3O_4F$: C, 68.42; H, 6.15; N, 8.55. Found: C, 68.16; H, 5.98; N, 8.46.

Example 24

3-[1-(4-(4-[(2-{(E)-2-[4-(trifluoromethyl)phenyl]ethenyl}-1,3-oxazol-4-yl)methoxy]phenyl}butyl)-1H-imidazol-2-yl]-1,2-propanediol

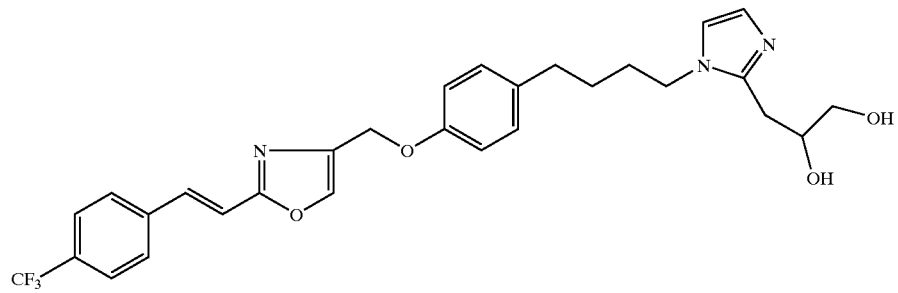

Using 3-{1-[4-(4-hydroxyphenyl)butyl]-1H-imidazol-2-yl}-1,2-propanediol (204 mg), 65% oily sodium hydride (28 mg) and 4-(chloromethyl)-2-{(E)-2-[4-(trifluoromethyl)phenyl]ethenyl}-1,3-oxazole (212 mg), the same reaction as Example 2 was carried out to yield the titled compound (285 mg).

mp 142–143° C.

¹H-NMR (CDCl₃) δ: 1.53–1.82 (4H, m), 2.59 (2H, t, J=7.1 Hz), 2.76 (1H, d, J=5.0 Hz), 2.77 (1H, d, J=7.0 Hz), 3.64 (1H, dd, J=4.8 Hz, 11.4 Hz), 3.76 (1H, dd, J=4.2 Hz, 11.4 Hz), 3.83 (2H, t, J=6.8 Hz), 4.12–4.24 (1H, m), 5.02 (2H, s), 6.81 (1H, d, J=1.4 Hz), 6.92 (1H, d, J=1.4 Hz), 6.93

(2H, d, J=8.8 Hz), 6.95 (1H, d, J=16.4 Hz), 7.08 (2H, d, J=8.8 Hz), 7.56 (1H, d, J=16.4 Hz), 7.64 (4H, s), 7.70 (1H, s).

IR (KBr): 3500–3200, 3148, 3071, 2936, 2867, 1642, 1615, 1582, 1510, 1491, 1466, 1416, 1397, 1323, 1246, 1173, 1138, 1117, 1067, 1046, 1017 cm$^{-1}$.

Anal calcd for $C_{29}H_{30}N_3O_4F_3$: C, 64.32; H, 5.58; N, 7.76. Found: C, 64.26; H, 5.70; N, 7.62

Example 25
3-[1-(3-{3-[(2-{(E)-2-[4-(trifluoromethyl)phenyl]ethenyl}-1,3-oxazol-4-yl)methoxy]phenyl}propyl)-1H-imidazol-2-yl]-1,2-propanediol

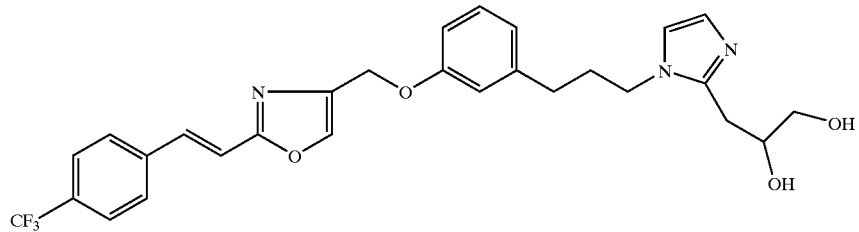

Using 3-{1-[3-(3-hydroxyphenyl)propyl]-1H-imidazol-2-yl}-1,2-propanediol (194 mg), 65% oily sodium hydride (28 mg) and 4-(chloromethyl)-2-{(E)-2-[4-(trifluoromethyl)phenyl]ethenyl}-1,3-oxazole (212 mg), the same reaction as Example 2 was carried out to yield the titled compound (255 mg).

mp 102–104° C.

$^1$H-NMR (CDCl$_3$) δ: 2.08 (2H, quintet, J=7.0 Hz), 2.62 (2H, t, J=7.4 Hz), 2.72 (1H, d, J=4.8 Hz), 2.73 (1H, d, J=7.6 Hz), 3.63 (1H, dd, J=4.8 Hz, 11.4 Hz), 3.74 (1H, dd, J=4.2 Hz, 11.4 Hz), 3.83 (2H, t, J=7.2 Hz), 4.13–4.24 (1H, m), 5.03 (2H, s), 6.77–6.91 (3H, m), 6.84 (1H, d, J=1.4 Hz), 6.94 (1H, d, J=1.4 Hz), 7.02 (1H, d, J=16.4 Hz), 7.25 (1H, t, J=7.8 Hz), 7.57 (1H, d, J=16.4 Hz), 7.64 (4H, s), 7.71 (1H, s).

IR (KBr): 3500–3200, 3108, 3056, 2932, 2867, 1613, 1599, 1586, 1534, 1489, 1451, 1416, 1325, 1260, 1167, 1125, 1069, 1030, 1017 cm$^{-1}$.

Anal calcd for $C_{28}H_{28}N_3O_4F_3$: C, 63.75; H, 5.35; N, 7.97. Found: C, 63.60; H, 5.32; N, 7.88.

Example 26
3-(1-{4-[4-({2-[(E)-2-(2,4-difluorophenyl)ethenyl]-1,3-oxazol-4-yl]methoxy)phenyl]butyl}-1H-imidazol-2-yl)-1,2-propanediol Using 3-{1-[4-(4-hydroxyphenyl)butyl]-1H-imidazol-2-yl}-1,2-propanediol(204 mg), 65% oily sodium hydride (28 mg) and 4-(chloromethyl)-2-[(E)-2-(2,4-difluorophenyl)ethenyl]-1,3-oxazole (188 mg), the same reaction as Example 2 was carried out to yield the titled compound (223 mg).

mp 126–128° C.

$^1$H-NMR (CDCl$_3$) δ: 1.52–1.81 (4H, m), 2.58 (2H, t, J=6.9 Hz), 2.77 (2H, d, J=5.4 Hz), 3.63 (1H, dd, J=4.8 Hz, 11.4 Hz), 3.75 (1H, dd, J=4.2 Hz, 11.4 Hz), 3.82 (2H, t, J=7.0 Hz), 4.10–4.24 (1H, m), 5.01 (2H, s), 6.76–7.02 (7H, m), 7.07 (2H, d, J=8.6 Hz), 7.48–7.51 (1H, m), 7.59 (1H, d, J=16.6 Hz), 7.67 (1H, s).

IR (KBr): 3500–3200, 3106, 3073, 3032, 2934, 2865, 1644, 1613, 1593, 1532, 1512, 1495, 1462, 1431, 1354, 1298, 1275, 1244, 1177, 1142, 1090, 1028 cm$^{-1}$.

Anal calcd for $C_{28}H_{29}N_3O_4F_2$: C, 66.00; H, 5.74; N, 8.25. Found: C, 65.89; H, 5.94; N, 8.37.

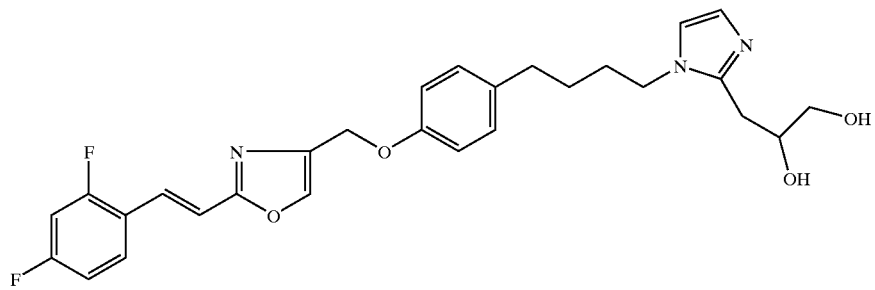

Example 27

3-(1-(3-[3-({2-[(E)-2-(2,4-difluorophenyl)ethenyl]-1,3-oxazol-4-yl}methoxy)phenyl]propyl}-1H-imidazol-2-yl)-1,2-propanediol

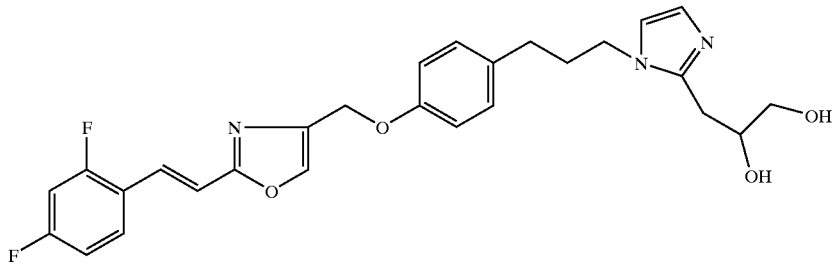

Using 3-{1-[3-(3-hydroxyphenyl)propyl]-1H-imidazol-2-yl}-1,2-propanediol (203 mg), 65% oily sodium hydride (29 mg) and 4-(chloromethyl)-2-[(E)-2-(2,4-difluorophenyl)ethenyl]-1,3-oxazole (197 mg), the same reaction as Example 2 was carried out to yield the titled compound (220 mg).

mp 92–94° C.

$^1$H-NMR (CDCl$_3$) δ: 2.08 (2H, quintet, J=7.2 Hz), 2.62 (2H, t, J=7.3 Hz), 2.73 (1H, d, J=5.0 Hz), 2.74 (1H, d, J=7.0 Hz), 3.63 (1H, dd, J=4.8 Hz, 11.2 Hz), 3.74 (1H, dd, J=4.2 Hz, 11.2 Hz), 3.83 (2H, t, J=7.4 Hz), 4.14–4.24 (1H, m), 5.02 (2H, s), 6.76–6.98 (5H, m), 6.84 (1H, d, J=1.4 Hz), 6.93 (1H, d, J=1.4 Hz), 6.98 (1H, d, J=16.4 Hz), 7.25 (1H, t, J=7.9 Hz), 7.48–7.61 (1H, m), 7.60 (1H, d, J=16.4 Hz), 7.69 (1H, s).

IR (KBr): 3500–3200, 3106, 3067, 3042, 2938, 2872, 1644, 1613, 1599, 1534, 1495, 1453, 1431, 1379, 1354, 1275, 1155, 1142, 1123, 1090, 1028 cm$^{-1}$.

Anal calcd for $C_{27}H_{27}N_3O_4F_2$: C, 65.44; H, 5.49; N, 8.48. Found: C, 65.39; H, 5.32; N, 8.62.

Example 28

3-[1-[4-[4-[[2-[(E)-2-(2,6-difluorophenyl)ethenyl]-1,3-oxazol-4-yl]methoxy]phenyl]butyl]-1H-imidazol-2-yl]-1,2-propanediol

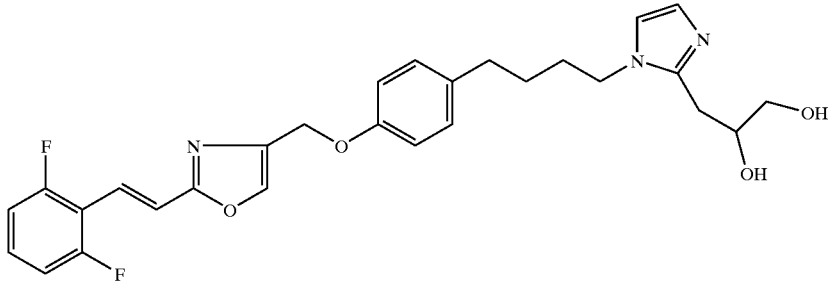

Using 3-{1-[3-(3-hydroxyphenyl)propyl]-1H-imidazol-2-yl}-1,2-propanediol (142 mg), 60% oily sodium hydride (40 mg) and 4-(chloromethyl)-2-[(E)-2-(2,6-difluorophenyl)ethenyl]-1,3-oxazole (495 mg), the same reaction as Example 2 was carried out to yield the titled compound (395 mg) as colorless crystals.

mp 123–125° C.

$^1$H-NMR (CDCl$_3$) δ: 1.5–1.8 (4H, m), 2.59 (2H, t, J=7.0), 2.7–2.8 (2H, m), 3.6–3.75 (2H, m), 3.83 (2H, t, J=7.0 Hz), 4.1–4.25 (1H, m), 5.03 (2H, s), 6.8–7.0 (4H, m), 6.92 (2H, d, J=8.6 Hz), 7.07 (2H, d, J=8.6 Hz), 7.2–7.3 (1H, m), 7.29 (1H, d, J=16.8 Hz), 7.61 (1H, d, J=16.8 Hz), 7.69 (1H, s).

IR (KBr): 1620, 1508, 1458, 1236, 1051, 1001, 789 cm$^{-1}$.

Anal. calcd for $C_{28}H_{29}F_2N_3O_4$: C, 66.00; H, 5.74; N, 8.25. Found: C, 65.71; H, 5.78; N, 8.09.

Example 29
(2R)-3-[[1-[4-[4-[[2-[(E)-2-(2,4-difluorophenyl)ethenyl]-1,3-oxazol-4-yl]methoxy]phenyl]butyl]-1H-imidazol-2-yl]-1,2-propanediol

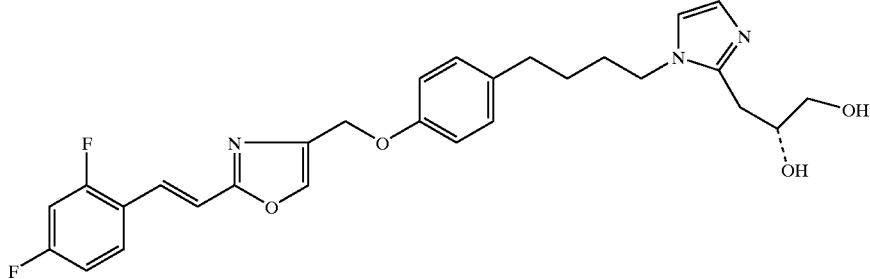

To a solution of (2R)-3-(1H-imidazol-2-yl)-1,2-propanediol (127 mg) in DMF (4 ml), 60% oily sodium hydride (37 mg) was added under ice cooling. After stirring at room temperature for 30 minutes, 4-[[4-(4-iodobutyl)phenoxy]methyl]-2-[(E)-2-(2,4-difluorophenyl)ethenyl]-1,3-oxazole (485 mg) was added under ice cooling. After stirring at room temperature for 3 hours, water was added under ice cooling. The reaction mixture was extracted with a mixture of THF-ethyl acetate and washed with water and saline and dried over magnesium sulfate, after which it was concentrated under reduced pressure. The residue was purified by silica gel column chromatography (eluent: ethyl acetate-methanol=10:1), after which it was recrystallized from ethyl acetate-hexane to yield the titled compound (262 mg) as colorless crystals.

mp 104–106° C.

$^1$H-NMR (CDCl$_3$) δ: 1.5–1.8 (4H, m), 2.59 (2H, t, J=7.0 Hz), 2.7–2.8 (2H, m), 3.55–3.75 (2H, m), 3.79 (2H, t, J=7.0 Hz), 4.1–4.2 (1H, m), 5.01 (2H, s), 6.8–7.1 (5H, m), 6.92 (2H, d, J=8.4 Hz), 7.07 (2H, d, J=8.4 Hz), 7.5–7.6 (1H, m), 7.59 (1H, d, J=16.2 Hz), 7.67 (1H, s).

IR (KBr): 1507, 1472, 1273, 1235, 1140, 1092, 966, 858 cm$^{-1}$.

Anal. calcd for C$_{28}$H$_{29}$F$_2$N$_3$O$_4$: C, 66.00; H, 5.74; N, 8.25. Found: C, 65.69; H, 5.82; N, 8.06.

$[α]^{22}_D$=+4.2° (c=1.0, methanol)

Example 30
(2S)-3-[[1-[4-[4-[[2-[(E)-2-(2,4-difluorophenyl)ethenyl]-1,3-oxazol-4-yl]methoxy]phenyl]butyl]-1H-imidazol-2-yl]-1,2-propanediol Using (2S)-3-(1H-imidazol-2-yl)-1,2-propanediol, 60% oily sodium hydride (50 mg) and 4-[[4-(4-iodobutyl)phenoxy]methyl]-2-[(E)-2-(2,4-difluorophenyl)ethenyl]-1,3-oxazole (415 mg), the same reaction as Example 29 was carried out to yield the titled compound (219 mg) as colorless crystals.

mp 106–108° C.

$^1$H-NMR (CDCl$_3$) δ: 1.5–1.8 (4H, m), 2.58 (2H, t, J=6.8 Hz), 2.7–2.8 (2H, m), 3.6–3.75 (2H, m), 3.82 (2H, t, J=7.0 Hz), 4.1–4.2 (1H, m), 5.01 (2H, s), 6.8–7.1 (5H, m), 6.89 (2H, d, J=8.4 Hz), 7.07 (2H, d, J=8.4 Hz), 7.5–7.6 (1H, m), 7.59 (1H, d, J=16.4 Hz), 7.67 (1H, s).

IR (KBr): 1615, 1512, 1497, 1273, 1246, 1229, 1140, 1094, 1046, 966, 847 cm$^{-1}$.

Anal. calcd for C$_{28}$H$_{29}$F$_2$N$_3$O$_4$: C, 66.00; H, 5.74; N, 8.25. Found: C, 65.75; H, 5.60; N, 8.12.

$[α]^{22}_D$=−3.5° (c=1.0, methanol).

Preparation Example 1

Amount per Tablet

| | |
|---|---|
| (1) Compound obtained in Example 4 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 4, 60.0 mg of lactose, and 35.0 mg of corn starch was granulated through a 1 mm-mesh sieve using 0.03 ml of a 10% by weight aqueous solution of gelatin (3.0 mg of gelatin), after which the granules were dried at 40° C. and filtered again. The granules obtained were mixed with 2.0 mg of magnesium stearate and compressed. The core tablets

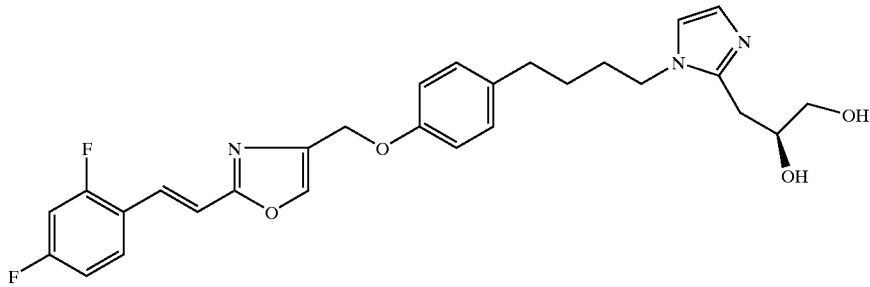

obtained were coated with a sugar coat comprising a suspension of sucrose, titanium dioxide, talc, and gum arabic and polished with beeswax to yield sugar-coated tablets.

Preparation Example 2

Dose per Tablet

| | |
|---|---|
| (1) Compound obtained in Example 4 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 4 and 3.0 mg of magnesium stearate were granulated using 0.07 ml of an aqueous solution of solubilized starch (7.0 mg of solubilized starch), after which these granules were dried and mixed with 70.0 mg of lactose and 50.0 mg of corn starch. This mixture was compressed to yield tablets.

In the following Test Examples, Compound Numbers indicate corresponding Example Numbers (e.g., the compound of Example 2 is indicated by Compound 2).

Test Example 1
Suppression of Receptor Tyrosine-Phosphorylation in Human Breast Cancer Cells Cells of human breast cancer cell line MCF-7 were suspended at 300,000 cells/0.5 mL, sown were into a 24-well plate, and cultured at 37° C. in the presence of 5% carbon dioxide. On the following day, 250 µl of a solution of the test compound times was added. After 2 hours, 250 µl of a heregulin solution, prepared to a final concentration of 0.8 µg/ml, was added. After 5 minutes, the a buffer solution for cell lysis was added to stop the reaction and yield a cell-lysed solution. After this cell-lysed solution was subjected to this protein was SDS-polyacrylamide gel electrophoresis to separate the protein, in the gel was transferred to a nylon filter. The protein in the gel was blotted onto a nylon filter. This filter was reacted with an anti-phosphotyrosine antibody; the portion containing phosphotyrosine on the filter was luminated using the ECL method to photosensitize an X-ray film. The amount of film photosensitization was determined using an image analyzer. Taking as 100% the amount of phosphorylation of the HER2 tyrosine inof the heregulin group, the ratio of the amount of phosphorylation of the HER2 tyrosine in each group receiving a solution of the test compound at each concentration was determined, and the test compound concentration required to achieve 50% suppression by the test compound of the amount of phosphorylation of HER2 tyrosine ($IC_{50}$ value) was calculated. The results are shown in Table 1. This finding showed that the compound of the present invention potently inhibits the phosphorylation reaction of the tyrosine residue of the receptor protein caused by activation of the receptor tyrosine kinase due to growth factor stimulation upon stimulation of human breast cancer cells by the growth factor heregulin.

TABLE 1

| Example number (compound number) | Inhibition of intracellular HER2 phosphorylation MCF-7 ($IC_{50}$: µM) |
|---|---|
| 2 | 1.9 |
| 3 | 0.18 |
| 4 | 0.10 |
| 6 | 1.2 |
| 11 | 1.1 |
| 20 | 1.5 |

TABLE 1-continued

| Example number (compound number) | Inhibition of intracellular HER2 phosphorylation MCF-7 ($IC_{50}$: µM) |
|---|---|
| 22 | 1.9 |
| 26 | 0.92 |

Test Example 2
Inhibitory Action on Breast Cancer Proliferation (in vitro)

Cells of human breast cancer cell line BT-474 (1,000 cells/100 µl) were sown to a 96-well microwellplate and cultured at 37° C. in the presence of 5% carbon dioxide. On the following day, 100 µl of a solution of each test compound, previously diluted 2-fold with a heregulin solution prepared to a final concentration of 0.04 µg/ml, was added, and the cells were cultured for 5 days. After the culture medium containing the test compound was removed, the cells were washed and fixed with 5% trichloroacetic acid, after which a 0.4% (w/v) SRB solution (dissolved in 1% acetic acid) was added to stain the cells (Skehan et al., Journal of the National Cancer Institute, Vol. 82, pp. 1107–1112, 1990). After the pigment solution was removed and the plate was washed with a 1% acetic acid solution, 100 µl of an extractant (10 mM Tris solution) was added to dissolve the pigment; absorbance was measured at an absorption wavelength of 550 nm to quantify the amount of cells as protein content. Taking as 100% the absorbance for the control group, which received no test compound solution, the ratio of the absorbance for each treatment group was determined, and the compound concentration required to achieve 50% suppression of the residual cell content relative to the control ($IC_{50}$ value) was calculated. The results are shown in Table 2.

The compound of the present invention was thus shown to potently suppress the proliferation of cells of the human breast cancer cell line BT-474.

TABLE 2

| Example number (compound number) | Cell growth inhibition BT-474 ($IC_{50}$: µM) |
|---|---|
| 2 | <0.05 |
| 3 | <0.05 |
| 4 | <0.05 |
| 6 | <0.05 |
| 11 | <0.05 |
| 19 | 0.017 |
| 20 | <0.05 |
| 22 | <0.05 |
| 26 | <0.05 |

Test Example 3
Inhibitory Action on Breast Cancer Cell Proliferation (in vivo)

5,000,000 cells of human breast cancer cell line BT-474 were suspended in Matrigel solution and transplanted subcutaneously atto a female BALB/c nude mouse (6 weeks of age) (Freedman et al., Proceedings of the National Academy of Science, USA, Vol. 87, pp. 6698–6702, 1990). Immediately after transplantation and at 7 days after transplantation, 50 µL of estradiol dipropionate (5 mg/mL solution) was administered intramuscularly into a hind legthe. At 14 days after transplantation, tumor diameter was measured, and 5 mice per group, uniformized with respect to tumor size, were used for the experiment. The compound of the present invention (4, 6, 14, 17, 19, 20, 23, 24, 26) in a 5% gum arabic suspension (physiological saline) was administered orally at a dose of 30 mg/kg twice daily for 10 days. On the day of administration initiation and the day after administration completion, tumor diameter was measured, and tumor volume was calculated using the equation shown below.

Tumor volume=maximum diameter×minimum diameter×minimum diameter×(½)

The ratio of the value obtained by subtracting the tumor volume on the day of administration initiation from the tumor volume on the day after administration completion in the control group, which received an gum arabic solution, and to that the value obtained by subtracting the tumor volume at the day of administration initiation from the tumor volume at the day of administration completion in each drug administration group was obtained as the proliferation rate. The results are shown in Table 3.

The compound of the present invention suppressed the growth of human breast cancer cells transplanted to nude mice. Mice were weighed during the test period; no body weight loss due to administration of the compound of the present invention was observed.

TABLE 3

| Example No. (Compound No.) | Proliferation rate (%) |
|---|---|
| 4 | 5 |
| 6 | 28 |
| 23 | 27 |
| 24 | 28 |
| 26 | 15 |

Industrial Applicability

Since Compound (I) of the present invention or a salt thereof possesses tyrosine kinase-inhibiting activity and is of low toxicity, it can be used to prevent or treat tyrosine kinase-dependent diseases in mammals. Tyrosine kinase-dependent diseases include diseases characterized by increased cell proliferation due to abnormal tyrosine kinase enzyme activity. Furthermore, Compound (I) of the present invention or a salt thereof specifically inhibits tyrosine kinase and is therefore also useful as a therapeutic agent for suppressing the growth of HER2-expressing cancer, or a preventive agent for preventing the transition of hormone-dependent cancer to hormone-independent cancer.

What is claimed is:

1. A compound which is 1-(4-{4-[(2-{(E)-2-[4-(trifluoromethyl)phenyl]ethenyl}-1,3-oxazol-4-yl)methoxy]phenyl}butyl)-1H-1,2,3-triazole, a pro drug thereof or a salt thereof.

2. A method for producing the compound as claimed in claim 1 or a salt thereof, comprising reacting 4-[4-(1H-1,2,3-triazol-1-yl)butyl]phenol, or a salt thereof, with 4-(chloromethyl)-2-{(E)-2-[4-(trifluoromethyl)phenyl]ethenyl}-1,3-oxazole or a salt thereof.

3. The compound as claimed in claim 1 or a salt thereof, which is in the form of a pro-drug.

4. A pharmaceutical composition comprising the compound as claimed in claim 1 or a salt thereof or a pro-drug thereof together with a pharmaceutically acceptable carrier.

5. A pharmaceutical composition which comprises the compound as claimed in claim 1 or a salt thereof or a pro-drug thereof and another anti-cancer agent.

6. A pharmaceutical composition which comprises the compound as claimed in claim 1 or a salt thereof or a pro-drug thereof and a hormonal therapeutic agent.

7. The pharmaceutical composition as claimed in claim 6, wherein the hormonal therapeutic agent is an LH-RH modulator.

8. The pharmaceutical composition as claimed in claim 7, wherein the LH-RH modulator is an LH-RH antagonist.

9. The pharmaceutical composition as claimed in claim 8, wherein the LH-RH antagonist is leuprorelin or a salt thereof.

10. A method for inhibiting tyrosine-kinase, which comprises administering an effective amount of the compound as claimed in claim 1 or a salt thereof or a pro-drug thereof to a mammal.

11. A method for treating cancer, which comprises administering an effective amount of the compound as claimed in claim 1 or a salt thereof or a pro-drug thereof to a mammal.

12. A method for treating cancer, which comprises (1) administering an effective amount of the compound as claimed in claim 1 or a salt thereof or a pro-drug thereof to a mammal, in combination with (2) 1 to 3 members selected from the group consisting (i) administering an effective amount of another anti-cancer agent to the mammal, (ii) administering an effective amount of a hormonal therapeutic agent to the mammal, and (iii) performing a non-drug therapy on the mammal.

13. The method as claimed in claim 12, wherein the non-drug therapy is surgery, hypertensive chemotherapy, genetherapy, thermotherapy, cryotherapy, laser cauterization and/or radiotherapy.

14. A method for treating cancer, which comprises administering in combination an effective amount of the compound as claimed in claim 1 or a salt thereof or a pro-drug thereof and an effective amount of another anti-cancer agent to a mammal.

15. A method for treating cancer, which comprises administering in combination an effective amount of the compound as claimed in claim 1 or a salt thereof or a pro-drug thereof and an effective amount of a hormonal therapeutic agent to a mammal.

16. The method claimed in claim 15, wherein the hormonal therapeutic agent is an LH-RH modulator.

17. The method as claimed in claim 16, wherein the LH-RH modulator is an LH-RH antagonist.

18. The method as claimed in claim 17, wherein the LH-RH antagonist is leuprorelin or a salt thereof.

19. A method for treating cancer, which comprises administering an effective amount of the compound as claimed in claim 1 or a salt thereof or a pro-drug thereof to a mammal before surgery, hypertensive chemotherapy, genetherapy, thermotherapy, cryotherapy, laser cauterization and/or radiotherapy.

20. A method for treating cancer, which comprises administering an effective amount of the compound as claimed in claim 1 or a salt thereof or a pro-drug thereof to a mammal after surgery, hypertensive chemotherapy, genetherapy, thermotherapy, cryotherapy, laser cauterization and/or radiotherapy.

21. A method for treating cancer, which comprises administering in combination an effective amount of the compound as claimed in claim 1 or a salt thereof or a pro-drug thereof and an effective amount of another anti-cancer agent to a mammal before surgery, hypertensive chemotherapy, genetherapy, thermotherapy, cryotherapy, laser cauterization and/or radiotherapy.

22. A method for treating cancer, which comprises administering in combination an effective amount of the compound as claimed in claim 1 or a salt thereof or a pro-drug thereof and an effective amount of a hormonal therapeutic agent to a mammal before surgery, hypertensive chemotherapy, genetherapy, thermotherapy, cryotherapy, laser cauterization and/or radiotherapy.

23. The method as claimed in claim 22, wherein the hormonal therapeutic agent is an LH-RH modulator.

24. The method as claimed in claim 23 wherein the LH-RH modulator is an LH-RH antagonist.

25. The method as claimed in claim 24 wherein the LH-RH antagonist is leuprorelin or a salt thereof.

26. A method for treating cancer, which comprises administering in combination an effective amount of the compound as claimed in claim 1 or a salt thereof or a pro-drug thereof and an effective amount of another anti-cancer agent to a mammal after surgery, hypertensive chemotherapy, genetherapy, thermotherapy, cryotherapy, laser cauterization and/or radiotherapy.

27. A method for treating cancer, which comprises administering in combination an effective amount of the compound as claimed in claim 1 or a salt thereof or a pro-drug thereof and an effective amount of a hormonal therapeutic agent to a mammal after surgery, hypertensive chemotherapy, genetherapy, thermotherapy, cryotherapy, laser cauterization and/or radiotherapy.

28. The method as claimed in claim 27, wherein the hormonal therapeutic agent is an LH-RH modulator.

29. The method as claimed in claim 28, wherein the LH-RH modulator is an LH-RH antagonist.

30. The method as claimed in claim 29, wherein the LH-RH antagonist is leuprorelin or a salt thereof.

* * * * *